United States Patent
Sahin et al.

(10) Patent No.: US 10,370,433 B2
(45) Date of Patent: Aug. 6, 2019

(54) COMPOSITIONS AND METHODS FOR DIAGNOSIS AND TREATMENT OF CANCER

(71) Applicant: BIONTECH AG, Mainz (DE)

(72) Inventors: Ugur Sahin, Mainz (DE); Joycelyn Wüstehube-Lausch, Worms (DE); Markus Fiedler, Halle an der Saale (DE); Matin Daneschdar, Budenheim (DE); Hans-Ulrich Schmoldt, Klein-Winternheim (DE)

(73) Assignee: Biontech AG, Mainz (DE)

( * ) Notice: Subject to any disclaimer, the term of this patent is extended or adjusted under 35 U.S.C. 154(b) by 0 days.

(21) Appl. No.: 15/552,215

(22) PCT Filed: Mar. 15, 2016

(86) PCT No.: PCT/EP2016/055601
§ 371 (c)(1),
(2) Date: Aug. 18, 2017

(87) PCT Pub. No.: WO2016/146639
PCT Pub. Date: Sep. 22, 2016

(65) Prior Publication Data
US 2018/0037632 A1 Feb. 8, 2018

Related U.S. Application Data

(63) Continuation-in-part of application No. PCT/EP2015/055560, filed on Mar. 17, 2015.

(51) Int. Cl.
*C07K 14/81* (2006.01)
*C07K 14/00* (2006.01)
*C07K 5/10* (2006.01)

(52) U.S. Cl.
CPC .... *C07K 14/811* (2013.01); *C12Y 304/21026* (2013.01)

(58) Field of Classification Search
CPC ...... C07K 14/811; C07K 14/81; C07K 14/00; C07K 5/10

USPC ....... 530/300, 324, 325, 326, 327, 328, 329, 530/330
See application file for complete search history.

(56) References Cited

U.S. PATENT DOCUMENTS

| | | | |
|---|---|---|---|
| 6,884,770 B1* | 4/2005 | Galdes | A61K 31/00 435/69.5 |
| 6,951,839 B1* | 10/2005 | Crompton | A61K 38/1709 424/130.1 |
| 8,278,262 B2* | 10/2012 | Kolmar | A61K 38/56 435/7.21 |
| 2009/0130692 A1* | 5/2009 | Kolmar | A61K 38/56 435/7.21 |

FOREIGN PATENT DOCUMENTS

| WO | WO 2006/042282 | 4/2006 |
|---|---|---|
| WO | WO 2014/057284 | 4/2014 |

OTHER PUBLICATIONS

A0A0A9HRK7 from UniProt, pp. 1-3. Integrated into UniProtKB/TrEMBL on Mar. 4, 2015.*
International Preliminary Report on Patentability for PCT/EP2016/055601 dated Sep. 28, 2017, 8 pages.
Glotzbach et al; "Combinatorial Optimization of Cystine-Knot Peptides towards High-Affinity Inhibitors of Human Matriptase-1," PLoS One, vol. 8, No. 10, Oct. 11, 2013, p. e76956.

* cited by examiner

*Primary Examiner* — Julie Ha
(74) *Attorney, Agent, or Firm* — McDonnell Boehnen Hulbert & Berghoff LLP

(57) ABSTRACT

The present invention relates to the diagnosis and treatment of cancerous diseases, in particular cancerous diseases expressing Seprase (Fap-alpha; fibroblast activation protein alpha). More particularly, the invention concerns peptides targeting Seprase.

Figure 1:
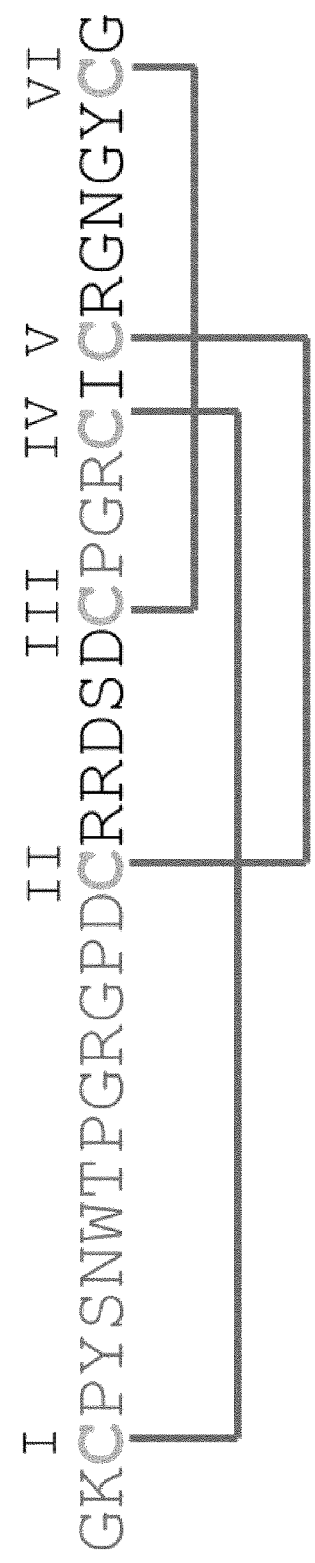

16 Claims, 33 Drawing Sheets
Specification includes a Sequence Listing.

A

| | | Apparenter K_D [nM] | Error | R2 Value | Relative Bindung im Vergleich zu Trx-MC-FA-010 [%] |
|---|---|---|---|---|---|
| | Trx-MC-FA-010 | 15,16 | 0,83 | 0,9982 | 100 |
| G | Trx-MC-FA-011 | 20,33 | 1,17 | 0,9981 | 74,55 |
| K | Trx-MC-FA-012 | 9,49 | 0,54 | 0,9981 | 159,67 |
| P | Trx-MC-FA-013 | 44,92 | 3,04 | 0,9976 | 33,74 |
| Y | Trx-MC-FA-014 | keine Bindung | | | 0 |
| S | Trx-MC-FA-015 | 16,2 | 1,02 | 0,9976 | 93,56 |
| N | Trx-MC-FA-016 | 113,29 | 11,54 | 0,9969 | 13,38 |
| W | Trx-MC-FA-017 | keine Bindung | | | 0 |
| T | Trx-MC-FA-018 | 50,61 | 3,63 | 0,9974 | 29,95 |
| P | Trx-MC-FA-019 | 78,68 | 7,6 | 0,9962 | 19,26 |
| G | Trx-MC-FA-0110 | keine Bindung | | | 0 |
| R | Trx-MC-FA-0111 | keine Bindung | | | 0 |
| G | Trx-MC-FA-0112 | 217,28 | 64,43 | 0,9863 | 6,98 |
| P | Trx-MC-FA-0113 | keine Bindung | | | 0 |
| D | Trx-MC-FA-0114 | 25,61 | 1,76 | 0,9973 | 59,19 |
| R | Trx-MC-FA-0115 | 18,78 | 1,17 | 0,9977 | 80,72 |
| | Trx-MC-Myc-010 | keine Bindung | | | 0 |

B

Figure 4

B

| Curve | ka (1/Ms) | kd (1/s) | KD (M) | Rmax (RU) | Conc (M) | tc | Flow (ul/min) | kt (RU/Ms) | RI (RU) | Chi² (RU²) | U-value |
|---|---|---|---|---|---|---|---|---|---|---|---|
| Cycle:5 37 nM | 2,684E+5 | 0,1507 | 5,615E-7 | 316,6 | 3,700E-8 | 6,730E+11 | | | | 9,42 | 1 |
| Cycle:6 111,11 nM | | | | | 1,111E-7 | | 30,00 | 2,091E+12 | -6,159 | | |
| Cycle:7 333,33 nM | | | | | 3,333E-7 | | 30,00 | 2,091E+12 | -20,64 | | |
| Cycle:8 1000 nM | | | | | 1,000E-6 | | 30,00 | 2,091E+12 | -34,78 | | |
| Cycle:9 3000 nM | | | | | 3,000E-6 | | 30,00 | 2,091E+12 | 22,77 | | |
| | | | | | | | 30,00 | 2,091E+12 | 20,39 | | |

Seprase (grün)
DPP-IV (türkis/grau)
Auf Sequenzebene 52 % Identität und 71 % Ähnlichkeit.

SEQUENCE LISTING

```
<160> NUMBER OF SEQ ID NOS: 96

<210> SEQ ID NO 1
<211> LENGTH: 2283
<212> TYPE: DNA
<213> ORGANISM: Homo sapiens

<400> SEQUENCE: 1
atgaagactt gggtaaaaat cgtatttgga gttgccacct ctgctgtgct tgccttattg      60
gtgatgtgca ttgtcttacg cccttcaaga gttcataact ctgaagaaaa tacaatgaga     120
gcactcacac tgaaggatat tttaaatgga acattttctt ataaaacatt ttttccaaac     180
tggatttcag gacaagaata tcttcatcaa tctgcagata caatatagt actttataat      240 attgaaacag gacaatcata taccattttg agtaatagaa ccatgaaaag tgtgaatgct     300
tcaaattacg gcttatcacc tgatcggcaa tttgtatatc tagaaagtga ttattcaaag     360
ctttggagat actcttacac agcaacatat tacatctatg accttagcaa tggagaattt     420
gtaagaggaa atgagcttcc tcgtccaatt cagtatttat gctggtcgcc tgttgggagt     480
aaattagcat atgtctatca aaacaatatc tatttgaaac aaagaccagg agatccacct     540
tttcaaataa catttaatgg aagagaaaat aaaatattta atggaatccc agactgggtt     600
tatgaagagg aaatgcttgc tacaaaatat gctctctggt ggtctcctaa tggaaaattt     660
ttggcatatg cggaatttaa tgatacggat ataccagtta ttgcctattc ctattatggc     720
gatgaacaat atcctagaac aataaatatt ccataccaa aggctggagc taagaatccc     780
gttgttcgga tatttattat cgataccact taccctgcgt atgtaggtcc ccaggaagtg     840
cctgttccag caatgatagc ctcaagtgat tattatttca gttggctcac gtgggttact     900
gatgaacgag tatgtttgca gtggctaaaa agagtccaga atgtttcggt cctgtctata     960
tgtgacttca gggaagactg gcagacatgg gattgtccaa agacccagga gcatatagaa    1020
gaaagcagaa ctggatgggc tggtggattc tttgtttcaa caccagtttt cagctatgat    1080
gccatttcgt actacaaaat atttagtgac aaggatggct acaaacatat tcactatatc    1140
aaagacactg tggaaaatgc tattcaaatt acaagtggca gtgggaggc cataaatata    1200 ttcagagtaa cacaggattc actgttttat tctagcaatg aatttgaaga ataccctgga    1260
agaagaaaca tctacagaat tagcattgga agctatccte caagcaagaa gtgtgttact    1320 tgccataaa ggaaagaaag gtgccaatat tacacagcaa gtttcagcga ctacgccaag    1380
tactatgcac ttgtctgcta cggcccaggc atccccattt ccaccttca tgatggacgc    1440
```

| | |
|---|---|
| actgatcaag aaattaaaat cctggaagaa aacaaggaat tggaaaatgc tttgaaaaat | 1500 |
| atccagctgc ctaaagagga aattaagaaa cttgaagtag atgaaattac tttatggtac | 1560 |
| aagatgattc ttcctcctca atttgacaga tcaaagaagt atcccttgct aattcaagtg | 1620 |
| tatggtggtc cctgcagtca gagtgtaagg tctgtatttg ctgttaattg gatatcttat | 1680 |
| cttgcaagta aggaagggat ggtcattgcc ttggtggatg gtcgaggaac agctttccaa | 1740 |
| ggtgacaaac tcctctatgc agtgtatcga aagctgggtg tttatgaagt tgaagaccag | 1800 |
| attacagctg tcagaaaatt catagaaatg ggtttcattg atgaaaaaag aatagccata | 1860 |
| tggggctggt cctatggagg atacgtttca tcactggccc ttgcatctgg aactggtctt | 1920 |
| ttcaaatgtg gtatagcagt ggctccagtc tccagctggg aatattacgc gtctgtctac | 1980 |
| acagagagat tcatgggtct cccaacaaag gatgataatc ttgagcacta taagaattca | 2040 |
| actgtgatgg caagagcaga atatttcaga aatgtagact atcttctcat ccacggaaca | 2100 |
| gcagatgata atgtgcactt tcaaaactca gcacagattc taaagctct ggttaatgca | 2160 |
| caagtggatt tccaggcaat gtggtactct gaccagaacc acggcttatc cggcctgtcc | 2220 |
| acgaaccact tatacaccca catgacccac ttcctaaagc agtgtttctc tttgtcagac | 2280 |
| taa | 2283 |

<210> SEQ ID NO 2
<211> LENGTH: 2286
<212> TYPE: DNA
<213> ORGANISM: Mus musculus

<400> SEQUENCE: 2

| | |
|---|---|
| atgaagacat ggctgaaaac tgtctttgga gttaccaccc tggctgcgct tgctttagtg | 60 |
| gtgatatgca ttgtcttacg tccctcaaga gtttacaaac ctgaaggaaa cacaaagaga | 120 |
| gctcttacct tgaaggatat tttaaatgga acattctcat ataaaacata tttttcccaac | 180 |
| tggatttcag aacaagaata tcttcatcaa tctgaggatg ataacatagt attttataat | 240 |
| attgaaacaa gagaatcata tatcattttg agtaatagca ccatgaaaag tgtgaatgct | 300 |
| acagattatg gtttgtcacc tgatcggcaa tttgtgtatc tagaaagtga ttattcaaag | 360 |
| ctctggcgat attcatacac agcgacatac tacatctacg accttcagaa tggggaattt | 420 |
| gtaagaggat acgagctccc tcgtccaatt cagtatctat gctggtcgcc tgttgggagt | 480 |
| aaattagcat atgtatatca aaacaatatt tatttgaaac aaagaccagg agatccacct | 540 |
| tttcaaataa cttatactgg aagagaaaat agaatattta tggaatacc agactgggtt | 600 |
| tatgaagagg aaatgcttgc cacaaaatat gctctttggt ggtctccaga tggaaaattt | 660 |
| ttggcatatg tagaatttaa tgattcagat ataccaatta ttgcctattc ttattatggt | 720 |
| gatggacagt atcctagaac tataaatatt ccatatccaa aggctggggc taagaatccg | 780 |
| gttgttcgtg tttttattgt tgacaccacc taccctcacc acgtgggccc aatgaaagtg | 840 |
| ccagttccag aaatgatagc ctcaagtgac tattatttca gctggctcac atgggtgtcc | 900 |
| agtgaacgag tatgcttgca gtggctaaaa agagtgcaga atgtctcagt cctgtctata | 960 |
| tgtgatttca gggaagactg gcatgcatgg gaatgtccaa gaaccaggga gcatgtagaa | 1020 |
| gaaagcagaa caggatgggc tggtggattc tttgtttcga caccagcttt tagccaggat | 1080 |
| gccacttctt actacaaaat atttagcgac aaggatggtt acaaacatat tcactacatc | 1140 |
| aaagacactg tggaaaatgc tattcaaatt acaagtggca agtgggaggc catatatata | 1200 |

-continued

```
ttccgcgtaa cacaggattc actgttttat tctagcaatg aatttgaagg ttaccctgga     1260
agaagaaaca tctacagaat tagcattgga aactctcctc cgagcaagaa gtgtgttact     1320
tgccatctaa ggaagaaag gtgccaatat tacacagcaa gtttcagcta caaagccaag      1380
tactatgcac tcgtctgcta tggccctggc ctccccattt ccaccctcca tgatggccgc     1440
acagaccaag aaatacaagt attagaagaa acaaagaac tggaaaattc tctgagaaat      1500
atccagctgc ctaaagtgga gattaagaag ctcaaagacg ggggactgac tttctggtac     1560
aagatgattc tgcctcctca gtttgacaga tcaaagaagt acccctttgct aattcaagtg    1620 tatggtggtc cttgcagcca gagtgttaag tctgtgtttg ctgttaattg gataacttat     1680
ctcgcaagta aggaggggat agtcattgcc ctggtagatg gtcggggcac tgctttccaa     1740
ggtgacaaat tcctgcatgc cgtgtatcga aaactgggtg tatatgaagt tgaggaccag     1800
ctcacagctg tcagaaaatt catagaaatg ggtttcattg atgaagaaag aatagccata     1860
tggggctggt cctacggagg ttatgtttca tccctggccc ttgcatctgg aactggtctt     1920
ttcaaatgtg gcatagcagt ggctccagtc tccagctggg aatattacgc atctatctac     1980
tcagagagat tcatgggcct cccaacaaag gacgacaatc tcgaacacta taaaaattca     2040
actgtgatgg caagagcaga atatttcaga aatgtagact atcttctcat ccacggaaca     2100
gcagatgata atgtgcactt tcagaactca gcacagattg ctaaagcttt ggttaatgca     2160
caagtggatt tccaggcgat gtggtactct gaccagaacc atggtatatc atctgggcgc     2220
tcccagaatc atttatatac ccacatgacg cacttcctca agcaatgctt ttctttatca     2280
gactga                                                                2286
```

<210> SEQ ID NO 3
<211> LENGTH: 760
<212> TYPE: PRT
<213> ORGANISM: Homo sapiens

<400> SEQUENCE: 3

```
Met Lys Thr Trp Val Lys Ile Val Phe Gly Val Ala Thr Ser Ala Val
1               5                   10                  15

Leu Ala Leu Leu Val Met Cys Ile Val Leu Arg Pro Ser Arg Val His
                20                  25                  30

Asn Ser Glu Glu Asn Thr Met Arg Ala Leu Thr Leu Lys Asp Ile Leu
            35                  40                  45

Asn Gly Thr Phe Ser Tyr Lys Thr Phe Phe Pro Asn Trp Ile Ser Gly
        50                  55                  60

Gln Glu Tyr Leu His Gln Ser Ala Asp Asn Asn Ile Val Leu Tyr Asn
65                  70                  75                  80

Ile Glu Thr Gly Gln Ser Tyr Thr Ile Leu Ser Asn Arg Thr Met Lys
                85                  90                  95

Ser Val Asn Ala Ser Asn Tyr Gly Leu Ser Pro Asp Arg Gln Phe Val
            100                 105                 110

Tyr Leu Glu Ser Asp Tyr Ser Lys Leu Trp Arg Tyr Ser Tyr Thr Ala
        115                 120                 125

Thr Tyr Tyr Ile Tyr Asp Leu Ser Asn Gly Glu Phe Val Arg Gly Asn
    130                 135                 140

Glu Leu Pro Arg Pro Ile Gln Tyr Leu Cys Trp Ser Pro Val Gly Ser
145                 150                 155                 160

Lys Leu Ala Tyr Val Tyr Gln Asn Asn Ile Tyr Leu Lys Gln Arg Pro
                165                 170                 175
```

```
Gly Asp Pro Pro Phe Gln Ile Thr Phe Asn Gly Arg Glu Asn Lys Ile
                180                 185                 190

Phe Asn Gly Ile Pro Asp Trp Val Tyr Glu Glu Met Leu Ala Thr
            195                 200                 205

Lys Tyr Ala Leu Trp Trp Ser Pro Asn Gly Lys Phe Leu Ala Tyr Ala
            210                 215                 220

Glu Phe Asn Asp Thr Asp Ile Pro Val Ile Ala Tyr Ser Tyr Tyr Gly
225                 230                 235                 240

Asp Glu Gln Tyr Pro Arg Thr Ile Asn Ile Pro Tyr Pro Lys Ala Gly
            245                 250                 255

Ala Lys Asn Pro Val Val Arg Ile Phe Ile Ile Asp Thr Thr Tyr Pro
            260                 265                 270

Ala Tyr Val Gly Pro Gln Glu Val Pro Val Pro Ala Met Ile Ala Ser
            275                 280                 285

Ser Asp Tyr Tyr Phe Ser Trp Leu Thr Trp Val Thr Asp Glu Arg Val
            290                 295                 300

Cys Leu Gln Trp Leu Lys Arg Val Gln Asn Val Ser Val Leu Ser Ile
305                 310                 315                 320

Cys Asp Phe Arg Glu Asp Trp Gln Thr Trp Asp Cys Pro Lys Thr Gln
            325                 330                 335

Glu His Ile Glu Glu Ser Arg Thr Gly Trp Ala Gly Gly Phe Phe Val
            340                 345                 350

Ser Thr Pro Val Phe Ser Tyr Asp Ala Ile Ser Tyr Lys Ile Phe
            355                 360                 365

Ser Asp Lys Asp Gly Tyr Lys His Ile His Tyr Ile Lys Asp Thr Val
370                 375                 380

Glu Asn Ala Ile Gln Ile Thr Ser Gly Lys Trp Glu Ala Ile Asn Ile
385                 390                 395                 400

Phe Arg Val Thr Gln Asp Ser Leu Phe Tyr Ser Ser Asn Glu Phe Glu
            405                 410                 415

Glu Tyr Pro Gly Arg Arg Asn Ile Tyr Arg Ile Ser Ile Gly Ser Tyr
            420                 425                 430

Pro Pro Ser Lys Lys Cys Val Thr Cys His Leu Arg Lys Glu Arg Cys
            435                 440                 445

Gln Tyr Tyr Thr Ala Ser Phe Ser Asp Tyr Ala Lys Tyr Tyr Ala Leu
            450                 455                 460

Val Cys Tyr Gly Pro Gly Ile Pro Ile Ser Thr Leu His Asp Gly Arg
465                 470                 475                 480

Thr Asp Gln Glu Ile Lys Ile Leu Glu Glu Asn Lys Glu Leu Glu Asn
            485                 490                 495

Ala Leu Lys Asn Ile Gln Leu Pro Lys Glu Glu Ile Lys Lys Leu Glu
            500                 505                 510

Val Asp Glu Ile Thr Leu Trp Tyr Lys Met Ile Leu Pro Pro Gln Phe
            515                 520                 525

Asp Arg Ser Lys Lys Tyr Pro Leu Leu Ile Gln Val Tyr Gly Gly Pro
            530                 535                 540

Cys Ser Gln Ser Val Arg Ser Val Phe Ala Val Asn Trp Ile Ser Tyr
545                 550                 555                 560

Leu Ala Ser Lys Glu Gly Met Val Ile Ala Leu Val Asp Gly Arg Gly
            565                 570                 575

Thr Ala Phe Gln Gly Asp Lys Leu Leu Tyr Ala Val Tyr Arg Lys Leu
            580                 585                 590

Gly Val Tyr Glu Val Glu Asp Gln Ile Thr Ala Val Arg Lys Phe Ile
```

```
                    595                 600                 605
Glu Met Gly Phe Ile Asp Glu Lys Arg Ile Ala Ile Trp Gly Trp Ser
    610                 615                 620
Tyr Gly Gly Tyr Val Ser Ser Leu Ala Leu Ala Ser Gly Thr Gly Leu
625                 630                 635                 640
Phe Lys Cys Gly Ile Ala Val Ala Pro Val Ser Ser Trp Glu Tyr Tyr
                    645                 650                 655
Ala Ser Val Tyr Thr Glu Arg Phe Met Gly Leu Pro Thr Lys Asp Asp
                660                 665                 670
Asn Leu Glu His Tyr Lys Asn Ser Thr Val Met Ala Arg Ala Glu Tyr
                675                 680                 685
Phe Arg Asn Val Asp Tyr Leu Leu Ile His Gly Thr Ala Asp Asp Asn
690                 695                 700
Val His Phe Gln Asn Ser Ala Gln Ile Ala Lys Ala Leu Val Asn Ala
705                 710                 715                 720
Gln Val Asp Phe Gln Ala Met Trp Tyr Ser Asp Gln Asn His Gly Leu
                725                 730                 735
Ser Gly Leu Ser Thr Asn His Leu Tyr Thr His Met Thr His Phe Leu
                740                 745                 750
Lys Gln Cys Phe Ser Leu Ser Asp
                755                 760

<210> SEQ ID NO 4
<211> LENGTH: 761
<212> TYPE: PRT
<213> ORGANISM: Mus musculus

<400> SEQUENCE: 4

Met Lys Thr Trp Leu Lys Thr Val Phe Gly Val Thr Thr Leu Ala Ala
1               5                   10                  15
Leu Ala Leu Val Val Ile Cys Ile Val Leu Arg Pro Ser Arg Val Tyr
                20                  25                  30
Lys Pro Glu Gly Asn Thr Lys Arg Ala Leu Thr Leu Lys Asp Ile Leu
            35                  40                  45
Asn Gly Thr Phe Ser Tyr Lys Thr Tyr Phe Pro Asn Trp Ile Ser Glu
        50                  55                  60
Gln Glu Tyr Leu His Gln Ser Glu Asp Asp Asn Ile Val Phe Tyr Asn
65                  70                  75                  80
Ile Glu Thr Arg Glu Ser Tyr Ile Ile Leu Ser Asn Ser Thr Met Lys
                85                  90                  95
Ser Val Asn Ala Thr Asp Tyr Gly Leu Ser Pro Asp Arg Gln Phe Val
                100                 105                 110
Tyr Leu Glu Ser Asp Tyr Ser Lys Leu Trp Arg Tyr Ser Tyr Thr Ala
            115                 120                 125
Thr Tyr Tyr Ile Tyr Asp Leu Gln Asn Gly Glu Phe Val Arg Gly Tyr
        130                 135                 140
Glu Leu Pro Arg Pro Ile Gln Tyr Leu Cys Trp Ser Pro Val Gly Ser
145                 150                 155                 160
Lys Leu Ala Tyr Val Tyr Gln Asn Asn Ile Tyr Leu Lys Gln Arg Pro
                165                 170                 175
Gly Asp Pro Pro Phe Gln Ile Thr Tyr Thr Gly Arg Glu Asn Arg Ile
                180                 185                 190
Phe Asn Gly Ile Pro Asp Trp Val Tyr Glu Glu Glu Met Leu Ala Thr
            195                 200                 205
```

-continued

Lys Tyr Ala Leu Trp Trp Ser Pro Asp Gly Lys Phe Leu Ala Tyr Val
    210                 215                 220

Glu Phe Asn Asp Ser Asp Ile Pro Ile Ile Ala Tyr Ser Tyr Tyr Gly
225                 230                 235                 240

Asp Gly Gln Tyr Pro Arg Thr Ile Asn Ile Pro Tyr Pro Lys Ala Gly
                245                 250                 255

Ala Lys Asn Pro Val Val Arg Val Phe Ile Val Asp Thr Thr Tyr Pro
            260                 265                 270

His His Val Gly Pro Met Glu Val Pro Val Pro Glu Met Ile Ala Ser
        275                 280                 285

Ser Asp Tyr Tyr Phe Ser Trp Leu Thr Trp Val Ser Ser Glu Arg Val
290                 295                 300

Cys Leu Gln Trp Leu Lys Arg Val Gln Asn Val Ser Val Leu Ser Ile
305                 310                 315                 320

Cys Asp Phe Arg Glu Asp Trp His Ala Trp Glu Cys Pro Lys Asn Gln
                325                 330                 335

Glu His Val Glu Glu Ser Arg Thr Gly Trp Ala Gly Phe Phe Val
            340                 345                 350

Ser Thr Pro Ala Phe Ser Gln Asp Ala Thr Ser Tyr Tyr Lys Ile Phe
        355                 360                 365

Ser Asp Lys Asp Gly Tyr Lys His Ile His Tyr Ile Lys Asp Thr Val
370                 375                 380

Glu Asn Ala Ile Gln Ile Thr Ser Gly Lys Trp Glu Ala Ile Tyr Ile
385                 390                 395                 400

Phe Arg Val Thr Gln Asp Ser Leu Phe Tyr Ser Ser Asn Glu Phe Glu
                405                 410                 415

Gly Tyr Pro Gly Arg Arg Asn Ile Tyr Arg Ile Ser Ile Gly Asn Ser
            420                 425                 430

Pro Pro Ser Lys Lys Cys Val Thr Cys His Leu Arg Lys Glu Arg Cys
        435                 440                 445

Gln Tyr Tyr Thr Ala Ser Phe Ser Tyr Lys Ala Lys Tyr Tyr Ala Leu
450                 455                 460

Val Cys Tyr Gly Pro Gly Leu Pro Ile Ser Thr Leu His Asp Gly Arg
465                 470                 475                 480

Thr Asp Gln Glu Ile Gln Val Leu Glu Glu Asn Lys Glu Leu Glu Asn
                485                 490                 495

Ser Leu Arg Asn Ile Gln Leu Pro Lys Val Glu Ile Lys Lys Leu Lys
            500                 505                 510

Asp Gly Gly Leu Thr Phe Trp Tyr Lys Met Ile Leu Pro Pro Gln Phe
        515                 520                 525

Asp Arg Ser Lys Lys Tyr Pro Leu Leu Ile Gln Val Tyr Gly Gly Pro
530                 535                 540

Cys Ser Gln Ser Val Lys Ser Val Phe Ala Val Asn Trp Ile Thr Tyr
545                 550                 555                 560

Leu Ala Ser Lys Glu Gly Ile Val Ile Ala Leu Val Asp Gly Arg Gly
                565                 570                 575

Thr Ala Phe Gln Gly Asp Lys Phe Leu His Ala Val Tyr Arg Lys Leu
            580                 585                 590

Gly Val Tyr Glu Val Glu Asp Gln Leu Thr Ala Val Arg Lys Phe Ile
        595                 600                 605

Glu Met Gly Phe Ile Asp Glu Glu Arg Ile Ala Ile Trp Gly Trp Ser
610                 615                 620

Tyr Gly Gly Tyr Val Ser Ser Leu Ala Leu Ala Ser Gly Thr Gly Leu

```
                625                 630                 635                 640

Phe Lys Cys Gly Ile Ala Val Ala Pro Val Ser Ser Trp Glu Tyr Tyr
                        645                 650                 655

Ala Ser Ile Tyr Ser Glu Arg Phe Met Gly Leu Pro Thr Lys Asp Asp
                    660                 665                 670

Asn Leu Glu His Tyr Lys Asn Ser Thr Val Met Ala Arg Ala Glu Tyr
                675                 680                 685

Phe Arg Asn Val Asp Tyr Leu Leu Ile His Gly Thr Ala Asp Asp Asn
            690                 695                 700

Val His Phe Gln Asn Ser Ala Gln Ile Ala Lys Ala Leu Val Asn Ala
        705                 710                 715                 720

Gln Val Asp Phe Gln Ala Met Trp Tyr Ser Asp Gln Asn His Gly Ile
                        725                 730                 735

Ser Ser Gly Arg Ser Gln Asn His Leu Tyr Thr His Met Thr His Phe
                    740                 745                 750

Leu Lys Gln Cys Phe Ser Leu Ser Asp
                755                 760

<210> SEQ ID NO 5
<211> LENGTH: 4
<212> TYPE: PRT
<213> ORGANISM: Artificial Sequence
<220> FEATURE:
<223> OTHER INFORMATION: Seprase binding peptide

<400> SEQUENCE: 5

Gly Arg Gly Pro
1

<210> SEQ ID NO 6
<211> LENGTH: 10
<212> TYPE: PRT
<213> ORGANISM: Artificial Sequence
<220> FEATURE:
<223> OTHER INFORMATION: Seprase binding peptide
<220> FEATURE:
<221> NAME/KEY: MISC_FEATURE
<222> LOCATION: (2)..(2)
<223> OTHER INFORMATION: Any amino acid, preferably an amino acid
      selected from the group consisting of Ser, Ala and Cys, more
      preferably an amino acid selected from the group consisting of Ser
      and Ala, more preferably Ser
<220> FEATURE:
<221> NAME/KEY: MISC_FEATURE
<222> LOCATION: (3)..(3)
<223> OTHER INFORMATION: Any amino acid, preferably an amino acid
      selected from the group consisting of Asn, Ala and Asp, more
      preferably an amino acid selected from the group consisting of Asn
      and Ala, more preferably Asn
<220> FEATURE:
<221> NAME/KEY: MISC_FEATURE
<222> LOCATION: (5)..(5)
<223> OTHER INFORMATION: any amino acid, preferably an amino acid
      selected from the group consisting of Thr, Ala and Val, more
      preferably an amino acid selected from the group consisting of Thr
      and Ala, more preferably Thr
<220> FEATURE:
<221> NAME/KEY: MISC_FEATURE
<222> LOCATION: (6)..(6)
<223> OTHER INFORMATION: Any amino acid, preferably an amino acid
      selected from the group consisting of Pro and Ala, more preferably
      Pro

<400> SEQUENCE: 6

Tyr Xaa Xaa Trp Xaa Xaa Gly Arg Gly Pro
1               5                   10
```

```
<210> SEQ ID NO 7
<211> LENGTH: 10
<212> TYPE: PRT
<213> ORGANISM: Artificial Sequence
<220> FEATURE:
<223> OTHER INFORMATION: Seprase binding peptide
<220> FEATURE:
<221> NAME/KEY: MISC_FEATURE
<222> LOCATION: (2)..(2)
<223> OTHER INFORMATION: Any amino acid, preferably an amino acid
      selected from the group consisting of Ser, Ala and Cys, more
      preferably an amino acid selected from the group consisting of Ser
      and Ala, more preferably Ser

<400> SEQUENCE: 7

Tyr Xaa Asn Trp Thr Pro Gly Arg Gly Pro
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Seprase binding peptide

<400> SEQUENCE: 8

Tyr Ser Asn Trp Thr Pro Gly Arg Gly Pro
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Seprase binding peptide
<220> FEATURE:
<221> NAME/KEY: MISC_FEATURE
<222> LOCATION: (1)..(1)
<223> OTHER INFORMATION: Any amino acid, preferably an amino acid
      selected from the group consisting of Pro and Ala, more preferably
      Pro
<220> FEATURE:
<221> NAME/KEY: MISC_FEATURE
<222> LOCATION: (3)..(3)
<223> OTHER INFORMATION: Any amino acid, preferably an amino acid
      selected from the group consisting of Ser, Ala and Cys, more
      preferably an amino acid selected from the group consisting of Ser
      and Ala, more preferably Ser
<220> FEATURE:
<221> NAME/KEY: MISC_FEATURE
<222> LOCATION: (4)..(4)
<223> OTHER INFORMATION: Any amino acid, preferably an amino acid
      selected from the group consisting of Asn, Ala and Asp, more
      preferably an amino acid selected from the group consisting of Asn
      and Ala, more preferably Asn
<220> FEATURE:
<221> NAME/KEY: MISC_FEATURE
<222> LOCATION: (6)..(6)
<223> OTHER INFORMATION: Any amino acid, preferably an amino acid
      selected from the group consisting of Thr, Ala and Val, more
      preferably an amino acid selected from the group consisting of Thr
      and Ala, more preferably Thr
<220> FEATURE:
<221> NAME/KEY: MISC_FEATURE
<222> LOCATION: (7)..(7)
<223> OTHER INFORMATION: Any amino acid, preferably an amino acid
      selected from the group consisting of Pro and Ala, more preferably
      Pro

<400> SEQUENCE: 9

Xaa Tyr Xaa Xaa Trp Xaa Xaa Gly Arg Gly Pro
1               5                   10
```

```
<210> SEQ ID NO 10
<211> LENGTH: 11
<212> TYPE: PRT
<213> ORGANISM: Artificial Sequence
<220> FEATURE:
<223> OTHER INFORMATION: Seprase binding peptide
<220> FEATURE:
<221> NAME/KEY: MISC_FEATURE
<222> LOCATION: (3)..(3)
<223> OTHER INFORMATION: Any amino acid, preferably an amino acid
      selected from the group consisting of Ser, Ala and Cys, more
      preferably an amino acid selected from the group consisting of Ser
      and Ala, more preferably Ser

<400> SEQUENCE: 10

Pro Tyr Xaa Asn Trp Thr Pro Gly Arg Gly Pro
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Seprase binding peptide

<400> SEQUENCE: 11

Pro Tyr Ser Asn Trp Thr Pro Gly Arg Gly Pro
1               5                   10

<210> SEQ ID NO 12
<211> LENGTH: 15
<212> TYPE: PRT
<213> ORGANISM: Artificial Sequence
<220> FEATURE:
<223> OTHER INFORMATION: Seprase binding peptide
<220> FEATURE:
<221> NAME/KEY: MISC_FEATURE
<222> LOCATION: (1)..(1)
<223> OTHER INFORMATION: Any amino acid, preferably an amino acid
      selected from the group consisting of Gly and Ala, more preferably
      Gly
<220> FEATURE:
<221> NAME/KEY: MISC_FEATURE
<222> LOCATION: (2)..(2)
<223> OTHER INFORMATION: Any amino acid, preferably an amino acid
      selected from the group consisting of Lys and Ala
<220> FEATURE:
<221> NAME/KEY: MISC_FEATURE
<222> LOCATION: (4)..(4)
<223> OTHER INFORMATION: Any amino acid, preferably an amino acid
      selected from the group consisting of Pro and Ala, more preferably
      Pro
<220> FEATURE:
<221> NAME/KEY: MISC_FEATURE
<222> LOCATION: (6)..(6)
<223> OTHER INFORMATION: Any amino acid, preferably an amino acid
      selected from the group consisting of Ser, Ala and Cys, more
      preferably an amino acid selected from the group consisting of Ser
      and Ala, more preferably Ser
<220> FEATURE:
<221> NAME/KEY: MISC_FEATURE
<222> LOCATION: (7)..(7)
<223> OTHER INFORMATION: Any amino acid, preferably an amino acid
      selected from the group consisting of Asn, Ala and Asp, more
      preferably an amino acid selected from the group consisting of Asn
      and Ala, more preferably Asn
<220> FEATURE:
<221> NAME/KEY: MISC_FEATURE
<222> LOCATION: (9)..(9)
<223> OTHER INFORMATION: Any amino acid, preferably an amino acid
      selected from the group consisting of Thr, Ala and Val, more
      preferably an amino acid selected from the group consisting of Thr
      and Ala, more preferably Thr
<220> FEATURE:
```

```
<221> NAME/KEY: MISC_FEATURE
<222> LOCATION: (10)..(10)
<223> OTHER INFORMATION: Any amino acid, preferably an amino acid
      selected from the group consisting of Pro and Ala, more preferably
      Pro
<220> FEATURE:
<221> NAME/KEY: MISC_FEATURE
<222> LOCATION: (15)..(15)
<223> OTHER INFORMATION: Any amino acid, preferably an amino acid
      selected from the group consisting of Asp, Ala and Asn, more
      preferably an amino acid selected from the group consisting of Asp
      and Ala, more preferably Asp

<400> SEQUENCE: 12

Xaa Xaa Cys Xaa Tyr Xaa Xaa Trp Xaa Xaa Gly Arg Gly Pro Xaa
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Seprase binding peptide
<220> FEATURE:
<221> NAME/KEY: MISC_FEATURE
<222> LOCATION: (1)..(1)
<223> OTHER INFORMATION: Any amino acid, preferably an amino acid
      selected from the group consisting of Gly and Ala, more preferably
      Gly
<220> FEATURE:
<221> NAME/KEY: MISC_FEATURE
<222> LOCATION: (2)..(2)
<223> OTHER INFORMATION: Any amino acid, preferably an amino acid
      selected from the group consisting of Lys and Ala
<220> FEATURE:
<221> NAME/KEY: MISC_FEATURE
<222> LOCATION: (6)..(6)
<223> OTHER INFORMATION: Any amino acid, preferably an amino acid
      selected from the group consisting of Ser, Ala and Cys, more
      preferably an amino acid selected from the group consisting of Ser
      and Ala, more preferably Ser
<220> FEATURE:
<221> NAME/KEY: MISC_FEATURE
<222> LOCATION: (15)..(15)
<223> OTHER INFORMATION: Any amino acid, preferably an amino acid
      selected from the group consisting of Asp, Ala and Asn, more
      preferably an amino acid selected from the group consisting of Asp
      and Ala, more preferably Asp

<400> SEQUENCE: 13

Xaa Xaa Cys Pro Tyr Xaa Asn Trp Thr Pro Gly Arg Gly Pro Xaa
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Seprase binding peptide

<400> SEQUENCE: 14

Gly Lys Cys Pro Tyr Ser Asn Trp Thr Pro Gly Arg Gly Pro Asp
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Seprase binding peptide

<400> SEQUENCE: 15
```

Gly Ala Cys Pro Tyr Ser Asn Trp Thr Pro Gly Arg Gly Pro Asp
1               5                   10                  15

<210> SEQ ID NO 16
<211> LENGTH: 18
<212> TYPE: PRT
<213> ORGANISM: Artificial Sequence
<220> FEATURE:
<223> OTHER INFORMATION: Seprase binding peptide
<220> FEATURE:
<221> NAME/KEY: MISC_FEATURE
<222> LOCATION: (1)..(1)
<223> OTHER INFORMATION: Independently from each other any amino acid
<220> FEATURE:
<221> NAME/KEY: REPEAT
<222> LOCATION: (1)..(1)
<223> OTHER INFORMATION: Repeated 0 to 4, preferably 1 or 2 times
<220> FEATURE:
<221> NAME/KEY: REPEAT
<222> LOCATION: (3)..(3)
<223> OTHER INFORMATION: Repeated 3 to 10, preferably 6, 7 or 8 times
<220> FEATURE:
<221> NAME/KEY: MISC_FEATURE
<222> LOCATION: (3)..(3)
<223> OTHER INFORMATION: Independently from each other any amino acid
<220> FEATURE:
<221> NAME/KEY: REPEAT
<222> LOCATION: (8)..(8)
<223> OTHER INFORMATION: Repeated 0 to 4, preferably 1 or 2 times
<220> FEATURE:
<221> NAME/KEY: MISC_FEATURE
<222> LOCATION: (8)..(8)
<223> OTHER INFORMATION: Independently from each other any amino acid
<220> FEATURE:
<221> NAME/KEY: REPEAT
<222> LOCATION: (10)..(10)
<223> OTHER INFORMATION: Repeated 3 to 7, preferably 4, 5 or 6 times
<220> FEATURE:
<221> NAME/KEY: MISC_FEATURE
<222> LOCATION: (10)..(10)
<223> OTHER INFORMATION: Independently from each other any amino acid
<220> FEATURE:
<221> NAME/KEY: REPEAT
<222> LOCATION: (12)..(12)
<223> OTHER INFORMATION: Repeated 2 to 6, preferably 2, 3 or 4 times
<220> FEATURE:
<221> NAME/KEY: MISC_FEATURE
<222> LOCATION: (12)..(12)
<223> OTHER INFORMATION: Independently from each other any amino acid
<220> FEATURE:
<221> NAME/KEY: REPEAT
<222> LOCATION: (14)..(14)
<223> OTHER INFORMATION: Repeated 1 to 3, preferably 1 or 2 times
<220> FEATURE:
<221> NAME/KEY: MISC_FEATURE
<222> LOCATION: (14)..(14)
<223> OTHER INFORMATION: Independently from each other any amino acid
<220> FEATURE:
<221> NAME/KEY: REPEAT
<222> LOCATION: (16)..(16)
<223> OTHER INFORMATION: Repeated 3 to 7, preferably 4, 5 or 6 times
<220> FEATURE:
<221> NAME/KEY: MISC_FEATURE
<222> LOCATION: (16)..(16)
<223> OTHER INFORMATION: Independently from each other any amino acid
<220> FEATURE:
<221> NAME/KEY: REPEAT
<222> LOCATION: (18)..(18)
<223> OTHER INFORMATION: Repeated 0 to 4, preferably 1 or 2 times
<220> FEATURE:
<221> NAME/KEY: MISC_FEATURE
<222> LOCATION: (18)..(18)
<223> OTHER INFORMATION: Independently from each other any amino acid

<400> SEQUENCE: 16

Xaa Cys Xaa Gly Arg Gly Pro Xaa Cys Xaa Cys Xaa Cys Xaa Cys Xaa
1               5                   10                  15

Cys Xaa

<210> SEQ ID NO 17
<211> LENGTH: 32
<212> TYPE: PRT
<213> ORGANISM: Artificial Sequence
<220> FEATURE:
<223> OTHER INFORMATION: Seprase binding peptide
<220> FEATURE:
<221> NAME/KEY: MISC_FEATURE
<222> LOCATION: (2)..(2)
<223> OTHER INFORMATION: Any amino acid, preferably an amino acid
      selected from the group consisting of Pro and Ala, more preferably
      Pro
<220> FEATURE:
<221> NAME/KEY: MISC_FEATURE
<222> LOCATION: (4)..(4)
<223> OTHER INFORMATION: Any amino acid, preferably an amino acid
      selected from the group consisting of Ser, Ala and Cys, more
      preferably an amino acid selected from the group consisting of Ser
      and Ala, more preferably Ser
<220> FEATURE:
<221> NAME/KEY: MISC_FEATURE
<222> LOCATION: (5)..(5)
<223> OTHER INFORMATION: Any amino acid, preferably an amino acid
      selected from the group consisting of Asn, Ala and Asp, more
      preferably an amino acid selected from the group consisting of Asn
      and Ala, more preferably Asn
<220> FEATURE:
<221> NAME/KEY: MISC_FEATURE
<222> LOCATION: (7)..(7)
<223> OTHER INFORMATION: Any amino acid, preferably an amino acid
      selected from the group consisting of Thr, Ala and Val, more
      preferably an amino acid selected from the group consisting of Thr
      and Ala, more preferably Thr
<220> FEATURE:
<221> NAME/KEY: MISC_FEATURE
<222> LOCATION: (8)..(8)
<223> OTHER INFORMATION: Any amino acid, preferably an amino acid
      selected from the group consisting of Pro and Ala, more preferably
      Pro
<220> FEATURE:
<221> NAME/KEY: MISC_FEATURE
<222> LOCATION: (13)..(13)
<223> OTHER INFORMATION: Any amino acid, preferably an amino acid
      selected from the group consisting of Asp, Ala and Asn, more
      preferably an amino acid selected from the group consisting of Asp
      and Ala, more preferably Asp
<220> FEATURE:
<221> NAME/KEY: MISC_FEATURE
<222> LOCATION: (23)..(23)
<223> OTHER INFORMATION: Any amino acid, preferably an amino acid
      selected from the group consisting of Arg and Ala, more preferably
      Arg

<400> SEQUENCE: 17

Cys Xaa Tyr Xaa Xaa Trp Xaa Xaa Gly Arg Gly Pro Xaa Cys Arg Arg
1               5                   10                  15

Asp Ser Asp Cys Pro Gly Xaa Cys Ile Cys Arg Gly Asn Gly Tyr Cys
            20                  25                  30

<210> SEQ ID NO 18
<211> LENGTH: 32
<212> TYPE: PRT
<213> ORGANISM: Artificial Sequence
<220> FEATURE:
<223> OTHER INFORMATION: Seprase binding peptide
<220> FEATURE:
<221> NAME/KEY: MISC_FEATURE
<222> LOCATION: (4)..(4)
<223> OTHER INFORMATION: Any amino acid, preferably an amino acid
      selected from the group consisting of Ser, Ala and Cys, more
      preferably an amino acid selected from the group consisting of Ser
      and Ala, more preferably Ser -continued

```
<220> FEATURE:
<221> NAME/KEY: MISC_FEATURE
<222> LOCATION: (13)..(13)
<223> OTHER INFORMATION: Any amino acid, preferably an amino acid
      selected from the group consisting of Asp, Ala and Asn, more
      preferably an amino acid selected from the group consisting of Asp
      and Ala, more preferably Asp
<220> FEATURE:
<221> NAME/KEY: MISC_FEATURE
<222> LOCATION: (23)..(23)
<223> OTHER INFORMATION: Any amino acid, preferably an amino acid
      selected from the group consisting of Arg and Ala, more preferably
      Arg

<400> SEQUENCE: 18

Cys Pro Tyr Xaa Asn Trp Thr Pro Gly Arg Gly Pro Xaa Cys Arg Arg
1               5                   10                  15

Asp Ser Asp Cys Pro Gly Xaa Cys Ile Cys Arg Gly Asn Gly Tyr Cys
            20                  25                  30

<210> SEQ ID NO 19
<211> LENGTH: 32
<212> TYPE: PRT
<213> ORGANISM: Artificial Sequence
<220> FEATURE:
<223> OTHER INFORMATION: Seprase binding peptide

<400> SEQUENCE: 19

Cys Pro Tyr Ser Asn Trp Thr Pro Gly Arg Gly Pro Asp Cys Arg Arg
1               5                   10                  15

Asp Ser Asp Cys Pro Gly Arg Cys Ile Cys Arg Gly Asn Gly Tyr Cys
            20                  25                  30

<210> SEQ ID NO 20
<211> LENGTH: 35
<212> TYPE: PRT
<213> ORGANISM: Artificial Sequence
<220> FEATURE:
<223> OTHER INFORMATION: Seprase binding peptide
<220> FEATURE:
<221> NAME/KEY: MISC_FEATURE
<222> LOCATION: (1)..(1)
<223> OTHER INFORMATION: Any amino acid, preferably an amino acid
      selected from the group consisting of Gly and Ala, more preferably
      Gly
<220> FEATURE:
<221> NAME/KEY: MISC_FEATURE
<222> LOCATION: (2)..(2)
<223> OTHER INFORMATION: Any amino acid, preferably an amino acid
      selected from the group consisting of Lys and Ala
<220> FEATURE:
<221> NAME/KEY: MISC_FEATURE
<222> LOCATION: (4)..(4)
<223> OTHER INFORMATION: Any amino acid, preferably an amino acid
      selected from the group consisting of Pro and Ala, more preferably
      Pro
<220> FEATURE:
<221> NAME/KEY: MISC_FEATURE
<222> LOCATION: (6)..(6)
<223> OTHER INFORMATION: Any amino acid, preferably an amino acid
      selected from the group consisting of Ser, Ala and Cys, more
      preferably an amino acid selected from the group consisting of Ser
      and Ala, more preferably Ser
<220> FEATURE:
<221> NAME/KEY: MISC_FEATURE
<222> LOCATION: (7)..(7)
<223> OTHER INFORMATION: Any amino acid, preferably an amino acid
      selected from the group consisting of Asn, Ala and Asp, more
      preferably an amino acid selected from the group consisting of Asn
      and Ala, more preferably Asn
<220> FEATURE:
<221> NAME/KEY: MISC_FEATURE
<222> LOCATION: (9)..(9)
```

```
<223> OTHER INFORMATION: Any amino acid, preferably an amino acid
      selected from the group consisting of Thr, Ala and Val, more
      preferably an amino acid selected from the group consisting of Thr
      and Ala, more preferably Thr
<220> FEATURE:
<221> NAME/KEY: MISC_FEATURE
<222> LOCATION: (10)..(10)
<223> OTHER INFORMATION: Any amino acid, preferably an amino acid
      selected from the group consisting of Pro and Ala, more preferably
      Pro
<220> FEATURE:
<221> NAME/KEY: MISC_FEATURE
<222> LOCATION: (15)..(15)
<223> OTHER INFORMATION: Any amino acid, preferably an amino acid
      selected from the group consisting of Asp, Ala and Asn, more
      preferably an amino acid selected from the group consisting of Asp
      and Ala, more preferably Asp
<220> FEATURE:
<221> NAME/KEY: MISC_FEATURE
<222> LOCATION: (25)..(25)
<223> OTHER INFORMATION: Any amino acid, preferably an amino acid
      selected from the group consisting of Arg and Ala, more preferably
      Arg

<400> SEQUENCE: 20

Xaa Xaa Cys Xaa Tyr Xaa Xaa Trp Xaa Xaa Gly Arg Gly Pro Xaa Cys
1               5                   10                  15

Arg Arg Asp Ser Asp Cys Pro Gly Xaa Cys Ile Cys Arg Gly Asn Gly
            20                  25                  30

Tyr Cys Gly
        35

<210> SEQ ID NO 21
<211> LENGTH: 35
<212> TYPE: PRT
<213> ORGANISM: Artificial Sequence
<220> FEATURE:
<223> OTHER INFORMATION: Seprase binding peptide
<220> FEATURE:
<221> NAME/KEY: MISC_FEATURE
<222> LOCATION: (1)..(1)
<223> OTHER INFORMATION: Any amino acid, preferably an amino acid
      selected from the group consisting of Gly and Ala, more preferably
      Gly
<220> FEATURE:
<221> NAME/KEY: MISC_FEATURE
<222> LOCATION: (2)..(2)
<223> OTHER INFORMATION: Any amino acid, preferably an amino acid
      selected from the group consisting of Lys and Ala
<220> FEATURE:
<221> NAME/KEY: MISC_FEATURE
<222> LOCATION: (6)..(6)
<223> OTHER INFORMATION: Any amino acid, preferably an amino acid
      selected from the group consisting of Ser, Ala and Cys, more
      preferably an amino acid selected from the group consisting of Ser
      and Ala, more preferably Ser
<220> FEATURE:
<221> NAME/KEY: MISC_FEATURE
<222> LOCATION: (15)..(15)
<223> OTHER INFORMATION: Any amino acid, preferably an amino acid
      selected from the group consisting of Asp, Ala and Asn, more
      preferably an amino acid selected from the group consisting of Asp
      and Ala, more preferably Asp
<220> FEATURE:
<221> NAME/KEY: MISC_FEATURE
<222> LOCATION: (25)..(25)
<223> OTHER INFORMATION: Any amino acid, preferably an amino acid
      selected from the group consisting of Arg and Ala, more preferably
      Arg

<400> SEQUENCE: 21

Xaa Xaa Cys Pro Tyr Xaa Asn Trp Thr Pro Gly Arg Gly Pro Xaa Cys
1               5                   10                  15
```

```
Arg Arg Asp Ser Asp Cys Pro Gly Xaa Cys Ile Cys Arg Gly Asn Gly
            20                  25                  30

Tyr Cys Gly
        35

<210> SEQ ID NO 22
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 22

Gly Lys Cys Pro Tyr Ser Asn Trp Thr Pro Gly Arg Gly Pro Asp Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 23
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 23

Gly Ala Cys Pro Tyr Ser Asn Trp Thr Pro Gly Arg Gly Pro Asp Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 24
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 24

Gly Ala Cys Pro Tyr Arg Asn Trp Met Thr Gly Arg Gly Pro Leu Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 25
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 25

Gly Ala Cys Met Tyr Met Asn Trp Thr Pro Gly Arg Gly Pro Asp Cys
1               5                   10                  15

Arg Arg Asp Ser Asp Cys Pro Gly Arg Cys Ile Cys Arg Gly Asn Gly
            20                  25                  30
```

-continued

Tyr Cys Gly
        35

<210> SEQ ID NO 26
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 26

Gly Ala Cys Pro Tyr Ala Ser Trp Ala Asp Gly Arg Gly Pro His Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 27
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 27

Gly Ala Cys Val Tyr Gln His Trp Gln Pro Gly Arg Gly Pro Ser Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 28
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 28

Gly Ala Cys Pro Tyr Ser Arg Trp Ala Val Gly Arg Gly Pro Ser Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 29
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 29

Gly Ala Cys Pro Tyr Thr Arg Trp Gln Pro Gly Arg Gly Pro Ser Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 30
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 30

Gly Ala Cys Pro Tyr Ser Asn Trp Ala Val Gly Arg Gly Pro Ser Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 31
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 31

Gly Ala Cys Pro Tyr Ser Arg Trp Ala Val Gly Arg Gly Pro Asp Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 32
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 32

Gly Ala Cys Pro Tyr Thr Asn Trp Arg Pro Gly Arg Gly Pro Ala Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 33
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 33

Gly Ala Cys Pro Tyr Ser Asn Trp Ala Val Gly Arg Gly Pro Ala Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 34
<211> LENGTH: 35

```
<212> TYPE: PRT
<213> ORGANISM: Artificial Sequence
<220> FEATURE:
<223> OTHER INFORMATION: Seprase binding peptide

<400> SEQUENCE: 34

Gly Ala Cys Pro Tyr Ser Arg Trp Met Pro Gly Arg Gly Pro Ser Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 35
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 35

Gly Ala Cys Pro Tyr Ala Asn Trp Ala Val Gly Arg Gly Pro Asn Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 36
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 36

Gly Ala Cys Pro Tyr Thr Tyr Trp His Pro Gly Arg Gly Pro Gly Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 37
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 37

Gly Ala Cys Pro Tyr Ser Asn Trp Arg Pro Gly Arg Gly Pro Glu Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 38
<211> LENGTH: 35
<212> TYPE: PRT
<213> ORGANISM: Artificial Sequence
<220> FEATURE:
```

<223> OTHER INFORMATION: Seprase binding peptide

<400> SEQUENCE: 38

Gly Ala Cys Pro Tyr Ala Asn Trp Met Val Gly Arg Gly Pro Ser Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 39
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 39

Gly Ala Cys Pro Tyr Thr Arg Trp Ala Val Gly Arg Gly Pro Asp Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 40
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 40

Gly Ala Cys Val Tyr His Thr Trp Met Pro Gly Arg Gly Pro Val Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 41
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 41

Gly Ala Cys Pro Tyr Ala Arg Trp Ala Ala Gly Arg Gly Pro Ala Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 42
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 42

```
Gly Ala Cys Pro Tyr Ser Thr Trp Gln Val Gly Arg Gly Pro Ser Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 43
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 43

Gly Ala Cys Pro Tyr Thr Arg Trp Thr Val Gly Arg Gly Pro Ser Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 44
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 44

Gly Ala Cys Gln Tyr Gly Leu Trp Glu Val Gly Arg Gly Pro Asp Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 45
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 45

Gly Ala Cys Pro Tyr Thr Asn Trp Gln Pro Gly Arg Gly Pro Ala Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 46
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 46

Gly Ala Cys Pro Tyr Thr Asn Trp His Pro Gly Arg Gly Pro Ala Cys
1               5                   10                  15
```

Arg Arg Asp Ser Asp Cys Pro Gly Arg Cys Ile Cys Arg Gly Asn Gly
            20                  25                  30

Tyr Cys Gly
        35

<210> SEQ ID NO 47
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 47

Gly Ala Cys Met Tyr Trp Gly Trp Glu Pro Gly Arg Gly Pro His Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 48
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 48

Gly Ala Cys Phe Tyr Ile Glu Trp Gln Val Gly Arg Gly Pro Ala Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 49
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 49

Gly Ala Cys Pro Tyr Ala Arg Trp Val Val Gly Arg Gly Pro Ser Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 50
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 50

Gly Ala Cys Ala Tyr Ala Asn Trp Gln Val Gly Arg Gly Pro Ser Cys
1               5                   10                  15

Arg Arg Asp Ser Asp Cys Pro Gly Arg Cys Ile Cys Arg Gly Asn Gly
            20                  25                  30

-continued

Tyr Cys Gly
        35

<210> SEQ ID NO 51
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 51

Gly Ala Cys Pro Tyr Ala Arg Trp Val Leu Gly Arg Gly Pro Asp Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 52
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 52

Gly Ala Cys Pro Tyr Thr Asn Trp His Pro Gly Arg Gly Pro Asp Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 53
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 53

Gly Ala Cys Pro Tyr Thr Tyr Trp His Ala Gly Arg Gly Pro Ser Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 54
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 54

Gly Ala Cys Pro Tyr Ser Thr Trp Ala Val Gly Arg Gly Pro Ala Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 55
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 55

Gly Ala Cys Pro Tyr Arg Asn Trp Ala Val Gly Arg Gly Pro Ser Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 56
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 56

Gly Ala Cys Pro Tyr Ala Thr Trp Gln Pro Gly Arg Gly Pro Ser Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 57
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 57

Gly Ala Cys Pro Tyr Ala Arg Trp Asn Val Gly Arg Gly Pro Ser Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 58
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 58

Gly Ala Cys Pro Tyr Ala Asn Trp Thr Ile Gly Arg Gly Pro Ala Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 59

```
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 59

Gly Ala Cys Pro Tyr Ala Arg Trp His Val Gly Arg Gly Pro Ser Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 60
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 60

Gly Ala Cys Ala Tyr Ser Asn Trp Ala Val Gly Arg Gly Pro Ser Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 61
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 61

Gly Ala Cys Pro Tyr Ser Thr Trp Ala Val Gly Arg Gly Pro Asp Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 62
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 62

Gly Ala Cys Pro Tyr Thr Asn Trp Ala Val Gly Arg Gly Pro Ser Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 63
<211> LENGTH: 35
<212> TYPE: PRT
<213> ORGANISM: Artificial Sequence
```

<220> FEATURE:
<223> OTHER INFORMATION: Seprase binding peptide

<400> SEQUENCE: 63

Gly Ala Cys Pro Tyr Ala Asn Trp Ala Val Gly Arg Gly Pro His Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 64
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 64

Gly Ala Cys Pro Tyr Arg Asn Trp Gln Pro Gly Arg Gly Pro Thr Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 65
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 65

Gly Ala Cys Pro Tyr Ser Asn Trp Thr Val Gly Arg Gly Pro Glu Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 66
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 66

Gly Ala Cys Pro Tyr His Thr Trp Ala Val Gly Arg Gly Pro Gly Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 67
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 67

Gly Ala Cys Pro Tyr Arg Asn Trp Ser Pro Gly Arg Gly Pro His Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 68
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 68

Gly Ala Cys Pro Tyr Thr Phe Trp Arg Val Gly Arg Gly Pro Ala Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 69
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 69

Gly Ala Cys Pro Tyr Ser Asn Trp Thr Val Gly Arg Gly Pro Ala Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 70
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 70

Gly Ala Cys Val Tyr Trp Gln Trp Ile Ala Gly Arg Gly Pro Val Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 71
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 71

Gly Ala Cys Trp Tyr Asp Pro Trp Trp Leu Gly Arg Gly Pro Val Cys

```
                1               5                  10                  15
Arg Arg Asp Ser Asp Cys Pro Gly Arg Cys Ile Cys Arg Gly Asn Gly
                20                  25                  30

Tyr Cys Gly
        35

<210> SEQ ID NO 72
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 72

Gly Ala Cys Met Tyr Asp Thr Trp Ala Gln Gly Arg Gly Pro Asn Cys
1               5                  10                  15

Arg Arg Asp Ser Asp Cys Pro Gly Arg Cys Ile Cys Arg Gly Asn Gly
                20                  25                  30

Tyr Cys Gly
        35

<210> SEQ ID NO 73
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 73

Gly Ala Cys Leu Tyr Glu Val Trp Pro Leu Gly Arg Gly Pro Gln Cys
1               5                  10                  15

Arg Arg Asp Ser Asp Cys Pro Gly Arg Cys Ile Cys Arg Gly Asn Gly
                20                  25                  30

Tyr Cys Gly
        35

<210> SEQ ID NO 74
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 74

Gly Ala Cys Ala Tyr Ser Asn Trp Gln Pro Gly Arg Gly Pro His Cys
1               5                  10                  15

Arg Arg Asp Ser Asp Cys Pro Gly Arg Cys Ile Cys Arg Gly Asn Gly
                20                  25                  30

Tyr Cys Gly
        35

<210> SEQ ID NO 75
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 75

Gly Ala Cys Glu Tyr His Val Trp Met Gly Gly Arg Gly Pro His Cys
1               5                  10                  15

Arg Arg Asp Ser Asp Cys Pro Gly Arg Cys Ile Cys Arg Gly Asn Gly
```

```
                20                  25                  30

Tyr Cys Gly
        35

<210> SEQ ID NO 76
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 76

Gly Ala Cys Ala Tyr Ser Ser Trp Ser Ala Gly Arg Gly Pro Met Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 77
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 77

Gly Ala Cys Pro Tyr Val Asn Trp Ala Ala Gly Arg Gly Pro Val Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 78
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 78

Gly Ala Cys Pro Tyr Ala Val Trp Ala Ser Gly Arg Gly Pro Ser Cys
1               5                   10                  15

Arg Arg Asp Ser Asp Cys Pro Gly Arg Cys Ile Cys Arg Gly Asn Gly
            20                  25                  30

Tyr Cys Gly
        35

<210> SEQ ID NO 79
<211> LENGTH: 35
<212> TYPE: PRT
<213> ORGANISM: Artificial Sequence
<220> FEATURE:
<223> OTHER INFORMATION: Seprase binding peptide

<400> SEQUENCE: 79

Gly Ala Cys Glu Tyr Ser Ala Trp Leu Ala Gly Arg Gly Pro Glu Cys
1               5                   10                  15

Arg Arg Asp Ser Asp Cys Pro Gly Arg Cys Ile Cys Arg Gly Asn Gly
            20                  25                  30

Tyr Cys Gly
```

<210> SEQ ID NO 80
<211> LENGTH: 32
<212> TYPE: DNA
<213> ORGANISM: Artificial Sequence
<220> FEATURE:
<223> OTHER INFORMATION: Oligonucleotide

<400> SEQUENCE: 80
gcgcaagctt gctgcggccc tcccgggtgc ac                                32

<210> SEQ ID NO 81
<211> LENGTH: 35
<212> TYPE: DNA
<213> ORGANISM: Artificial Sequence
<220> FEATURE:
<223> OTHER INFORMATION: Oligonucleotide

<400> SEQUENCE: 81
gcgcagcggc cgcgtcggac agggagaagc actgc                             35

<210> SEQ ID NO 82
<211> LENGTH: 5
<212> TYPE: PRT
<213> ORGANISM: Artificial Sequence
<220> FEATURE:
<223> OTHER INFORMATION: Serine protease motif
<220> FEATURE:
<221> NAME/KEY: MISC_FEATURE
<222> LOCATION: (2)..(2)
<223> OTHER INFORMATION: Any amino acid
<220> FEATURE:
<221> NAME/KEY: MISC_FEATURE
<222> LOCATION: (4)..(4)
<223> OTHER INFORMATION: Any amino acid

<400> SEQUENCE: 82

Gly Xaa Ser Xaa Gly
1               5

<210> SEQ ID NO 83
<211> LENGTH: 5
<212> TYPE: PRT
<213> ORGANISM: Artificial Sequence
<220> FEATURE:
<223> OTHER INFORMATION: Serine protease motif

<400> SEQUENCE: 83

Gly Trp Ser Tyr Gly
1               5

<210> SEQ ID NO 84
<211> LENGTH: 4
<212> TYPE: PRT
<213> ORGANISM: Artificial Sequence
<220> FEATURE:
<223> OTHER INFORMATION: Linker

<400> SEQUENCE: 84

Gly Phe Leu Gly
1

<210> SEQ ID NO 85
<211> LENGTH: 14
<212> TYPE: PRT
<213> ORGANISM: Artificial Sequence
<220> FEATURE:

-continued

```
<223> OTHER INFORMATION: Seprase binding peptide
<220> FEATURE:
<221> NAME/KEY: MISC_FEATURE
<222> LOCATION: (2)..(2)
<223> OTHER INFORMATION: Any amino acid, preferably an amino acid
      selected from the group consisting of Pro and Ala, more preferably
      Pro
<220> FEATURE:
<221> NAME/KEY: MISC_FEATURE
<222> LOCATION: (4)..(4)
<223> OTHER INFORMATION: Any amino acid, preferably an amino acid
      selected from the group consisting of Ser, Ala and Cys, more
      preferably an amino acid selected from the group consisting of Ser
      and Ala, more preferably Ser
<220> FEATURE:
<221> NAME/KEY: MISC_FEATURE
<222> LOCATION: (5)..(5)
<223> OTHER INFORMATION: Any amino acid, preferably an amino acid
      selected from the group consisting of Asn, Ala and Asp, more
      preferably an amino acid selected from the group consisting of Asn
      and Ala, more preferably Asn
<220> FEATURE:
<221> NAME/KEY: MISC_FEATURE
<222> LOCATION: (7)..(7)
<223> OTHER INFORMATION: Any amino acid, preferably an amino acid
      selected from the group consisting of Thr, Ala and Val, more
      preferably an amino acid selected from the group consisting of Thr
      and Ala, more preferably Thr
<220> FEATURE:
<221> NAME/KEY: MISC_FEATURE
<222> LOCATION: (8)..(8)
<223> OTHER INFORMATION: Any amino acid, preferably an amino acid
      selected from the group consisting of Pro and Ala, more preferably
      Pro
<220> FEATURE:
<221> NAME/KEY: MISC_FEATURE
<222> LOCATION: (13)..(13)
<223> OTHER INFORMATION: Any amino acid, preferably an amino acid
      selected from the group consisting of Asp, Ala and Asn, more
      preferably an amino acid selected from the group consisting of Asp
      and Ala, more preferably Asp

<400> SEQUENCE: 85

Cys Xaa Tyr Xaa Xaa Trp Xaa Xaa Gly Arg Gly Pro Xaa Cys
1               5                   10

<210> SEQ ID NO 86
<211> LENGTH: 14
<212> TYPE: PRT
<213> ORGANISM: Artificial Sequence
<220> FEATURE:
<223> OTHER INFORMATION: Seprase binding peptide
<220> FEATURE:
<221> NAME/KEY: MISC_FEATURE
<222> LOCATION: (4)..(4)
<223> OTHER INFORMATION: Any amino acid, preferably an amino acid
      selected from the group consisting of Ser, Ala and Cys, more
      preferably an amino acid selected from the group consisting of Ser
      and Ala, more preferably Ser
<220> FEATURE:
<221> NAME/KEY: MISC_FEATURE
<222> LOCATION: (13)..(13)
<223> OTHER INFORMATION: Any amino acid, preferably an amino acid
      selected from the group consisting of Asp, Ala and Asn, more
      preferably an amino acid selected from the group consisting of Asp
      and Ala, more preferably Asp

<400> SEQUENCE: 86

Cys Pro Tyr Xaa Asn Trp Thr Pro Gly Arg Gly Pro Xaa Cys
1               5                   10

<210> SEQ ID NO 87
<211> LENGTH: 14
<212> TYPE: PRT
<213> ORGANISM: Artificial Sequence
```

<220> FEATURE:
<223> OTHER INFORMATION: Seprase binding peptide

<400> SEQUENCE: 87

Cys Pro Tyr Ser Asn Trp Thr Pro Gly Arg Gly Pro Asp Cys
1               5                   10

<210> SEQ ID NO 88
<211> LENGTH: 37
<212> TYPE: PRT
<213> ORGANISM: Artificial Sequence
<220> FEATURE:
<223> OTHER INFORMATION: Seprase binding peptide

<400> SEQUENCE: 88

Gly Ser Gly Ala Cys Pro Tyr Ser Asn Trp Thr Pro Gly Arg Gly Pro
1               5                   10                  15

Asp Cys Ser Gln Asp Ser Asp Cys Leu Ala Gly Cys Val Cys Gly Pro
            20                  25                  30

Asn Gly Phe Cys Gly
        35

<210> SEQ ID NO 89
<211> LENGTH: 37
<212> TYPE: PRT
<213> ORGANISM: Artificial Sequence
<220> FEATURE:
<223> OTHER INFORMATION: Seprase binding peptide

<400> SEQUENCE: 89

Gly Ser Gly Ala Cys Pro Tyr Ser Asn Trp Thr Pro Gly Arg Gly Pro
1               5                   10                  15

Asp Cys Ser Ser Asp Ser Asp Cys Pro Gly Ala Cys Ile Cys Leu Glu
            20                  25                  30

Asn Gly Phe Cys Gly
        35

<210> SEQ ID NO 90
<211> LENGTH: 37
<212> TYPE: PRT
<213> ORGANISM: Artificial Sequence
<220> FEATURE:
<223> OTHER INFORMATION: Seprase binding peptide

<400> SEQUENCE: 90

Gly Ser Gly Ala Cys Pro Tyr Ser Arg Trp Met Pro Gly Arg Gly Pro
1               5                   10                  15

Ser Cys Arg Arg Asp Ser Asp Cys Pro Gly Arg Cys Ile Cys Arg Gly
            20                  25                  30

Asn Gly Tyr Cys Gly
        35

<210> SEQ ID NO 91
<211> LENGTH: 37
<212> TYPE: PRT
<213> ORGANISM: Artificial Sequence
<220> FEATURE:
<223> OTHER INFORMATION: Seprase binding peptide

<400> SEQUENCE: 91

Gly Ser Gly Ala Cys Pro Tyr Thr Asn Trp Arg Pro Gly Arg Gly Pro
1               5                   10                  15

Ala Cys Arg Arg Asp Ser Asp Cys Pro Gly Arg Cys Ile Cys Arg Gly

-continued

```
                 20                  25                  30

Asn Gly Tyr Cys Gly
        35

<210> SEQ ID NO 92
<211> LENGTH: 37
<212> TYPE: PRT
<213> ORGANISM: Artificial Sequence
<220> FEATURE:
<223> OTHER INFORMATION: Seprase binding peptide

<400> SEQUENCE: 92

Gly Ser Gly Ala Cys Pro Tyr Thr Arg Trp Ala Val Gly Arg Gly Pro
1               5                   10                  15

Asp Cys Arg Arg Asp Ser Asp Cys Pro Gly Arg Cys Ile Cys Arg Gly
            20                  25                  30

Asn Gly Tyr Cys Gly
        35

<210> SEQ ID NO 93
<211> LENGTH: 37
<212> TYPE: PRT
<213> ORGANISM: Artificial Sequence
<220> FEATURE:
<223> OTHER INFORMATION: Seprase binding peptide

<400> SEQUENCE: 93

Gly Ser Gly Ala Cys Pro Tyr Thr Arg Trp Gln Pro Gly Arg Gly Pro
1               5                   10                  15

Ser Cys Arg Arg Asp Ser Asp Cys Pro Gly Arg Cys Ile Cys Arg Gly
            20                  25                  30

Asn Gly Tyr Cys Gly
        35

<210> SEQ ID NO 94
<211> LENGTH: 37
<212> TYPE: PRT
<213> ORGANISM: Artificial Sequence
<220> FEATURE:
<223> OTHER INFORMATION: Seprase binding peptide

<400> SEQUENCE: 94

Gly Ser Gly Ala Cys Pro Tyr Ser Arg Trp Ala Val Gly Arg Gly Pro
1               5                   10                  15

Asp Cys Arg Arg Asp Ser Asp Cys Pro Gly Arg Cys Ile Cys Arg Gly
            20                  25                  30

Asn Gly Tyr Cys Gly
        35

<210> SEQ ID NO 95
<211> LENGTH: 37
<212> TYPE: PRT
<213> ORGANISM: Artificial Sequence
<220> FEATURE:
<223> OTHER INFORMATION: Seprase binding peptide

<400> SEQUENCE: 95

Gly Ser Gly Ala Cys Pro Tyr Ser Asn Trp Ala Val Gly Arg Gly Pro
1               5                   10                  15

Ser Cys Arg Arg Asp Ser Asp Cys Pro Gly Arg Cys Ile Cys Arg Gly
            20                  25                  30

Asn Gly Tyr Cys Gly
```

```
<210> SEQ ID NO 96
<211> LENGTH: 37
<212> TYPE: PRT
<213> ORGANISM: Artificial Sequence
<220> FEATURE:
<223> OTHER INFORMATION: Seprase binding peptide

<400> SEQUENCE: 96

Gly Ser Gly Ala Cys Pro Tyr Thr Asn Trp His Pro Gly Arg Gly Pro
1               5                   10                  15

Ala Cys Arg Arg Asp Ser Asp Cys Pro Gly Arg Cys Ile Cys Arg Gly
            20                  25                  30

Asn Gly Tyr Cys Gly
        35
```

COMPOSITIONS AND METHODS FOR DIAGNOSIS AND TREATMENT OF CANCER

REFERENCE TO RELATED APPLICATION(S)

This application is a U.S. national phase under 35 U.S.C. § 371 of International Patent Application no. PCT/EP2016/055601, filed Mar. 15, 2016, which claims the benefit International Patent Application no. PCT/EP2015/055560, filed Mar. 17, 2015.

TECHNICAL FIELD OF THE INVENTION

The present invention relates to the diagnosis and treatment of cancerous diseases, in particular cancerous diseases expressing Seprase (Fap-alpha; fibroblast activation protein alpha), such as breast cancer, pulmonary or lung cancer, e.g. non-small cell lung carcinoma (NSCLC), colorectal cancer, colon cancer, esophagus cancer, head and neck cancer, stomach cancer, bile duct cancer, pancreas cancer, kidney cancer, cervix cancer, ovary cancer, bladder cancer, endometrium cancer or prostate cancer. More particularly, the invention concerns peptides targeting Seprase.

BACKGROUND OF THE INVENTION

Cancer is one of the leading causes of death worldwide, surpassing heart disease. 8.2 million people of the global population died from cancer in 2012 (WHO). Classical anti-cancer therapies for example, radiotherapy, chemotherapy and conventional surgical procedures, often suffer from poor selectivity and, thus, from severe toxic side effects to healthy tissue. Novel forms of treatment consist in the targeted delivery of bioactive molecules (drugs, cytokines, radionuclides, etc.) to the tumor environment by means of binding molecules specific to tumor-associated antigens. This will allow the selective direction of drugs towards target-positive tumor tissue and effectively kill malignant cells without harming healthy cells. This goes along with the development of so-called companion diagnostics enabling the determination of target positive tumors within a patient in order to in advance guarantee a rationally tailored strategy for individual cancer therapy. In this, the application of target specific imaging techniques has become an important diagnostic step revealing an impressive advancement during the last decades. Imaging techniques can provide critical information about presence and quantity of tumor-associated proteins, localization, early detection, distribution, patient stratification, and treatment monitoring (Stern, Case et al. 2013).

A crucial step towards tailored personalized anticancer therapies is the identification of selectively tumor-associated marker proteins. The serine protease Seprase (Fap-alpha; fibroblast activation protein alpha) is selectively overexpressed in cancer-associated fibroblast (CAFs) in more than 90% of human primary epithelial tumors such as breast, lung and colorectal cancers with little to no expression in normal fibroblasts or other normal tissues (Rui Liu 2012), making it an attractive target for cancer therapy and diagnosis. Seprase is a 170 kDa type II transmembrane cell surface protein belonging to the post-proline dipeptidyl aminopeptidase family. It is anchored in the plasma membrane by a short transmembrane domain, intracellularly exposing an amino terminal sequence, whereas a catalytic domain with a carboxyl-terminus remains in the extracellular space (Goldstein, Ghersi et al. 1997, Pineiro-Sanchez, Goldstein et al. 1997). The exact role of Seprase in tumor growth and invasion, the molecular mechanism(s) the enzyme is involved in as well as its natural ligands or substrates remain largely unknown.

Being Seprase a selective marker for tumor tissue a number of potential therapeutic strategies targeting said protein can be envisioned. The use of Seprase binding molecules in a number of different cancer models in vivo has shown that it is possible to efficiently impair tumor progression in a preclinical approach (Loeffler, Kruger et al. 2006, Ostermann, Garin-Chesa et al. 2008, Liao, Luo et al. 2009, Kraman, Bambrough et al. 2010, Wen, Wang et al. 2010). In contrast to that, targeting Seprase in a clinical setup of human cancer patients using the monoclonal antibody F19, its humanized version Sibrotuzumab (Welt, Divgi et al. 1994, Hofheinz, al-Batran et al. 2003, Scott, Wiseman et al. 2003), or the Seprase enzyme-inhibitor Talabostat (Narra, Mullins et al. 2007, Eager, Cunningham et al. 2009, Eager, Cunningham et al. 2009), has demonstrated only modest clinical efficacy. Interestingly, no significant toxicities were reported in the preclinical studies targeting Seprase (Welt, Divgi et al. 1994, Lee, Fassnacht et al. 2005, Loeffler, Kruger et al. 2006, Ostermann, Garin-Chesa et al. 2008, Liao, Luo et al. 2009, Santos, Jung et al. 2009, Kraman, Bambrough et al. 2010, Wen, Wang et al. 2010) although an expression also by multipotent bone marrow stem cells (BMSCs) is currently discussed. In summary, the favorable biodistribution of the Seprase-specific antibodies and the selective uptake in sites of metastatic disease in patient reported so far (Welt, Divgi et al. 1994, Scott, Wiseman et al. 2003) qualify Seprase as an attractive candidate for tumor targeting approaches. Due to the fact that it remains unknown if Seprase acts as a tumor suppressor (Wesley, Albino et al. 1999, Ramirez-Montagut, Blachere et al. 2004) or promotes tumor growth (Cheng, Dunbrack et al. 2002, Goodman, Rozypal et al. 2003, Huang, Wang et al. 2004) it might be favorable to develop highly selective ligands to Seprase for imaging techniques having no impact on function but providing information about localization, early detection, distribution, patient stratification, and treatment monitoring (Stem, Case et al. 2013).

For targeting of poorly vascularized tumors, the large size of antibodies and even their fragments might slow the rate of tissue penetration and by this hamper efficient delivery. Moreover, because of the extended blood circulation of antibodies they seem not optimal for diagnostic use especially in the context of imaging concepts. In addition to the foresaid, the molecular architecture of antibodies, with complex glycosylation pattern and disulfide bridges, requires complex cost-intensive manufacturing and complicates further functionalization e.g. by means of an imaging tracer. To overcome these limitations, as an alternative to antibodies so-called protein scaffolds have emerged during the last decades: Scaffolds provide a robust structural framework to precisely engineer interaction molecules tailored for the tight and specific recognition of a given target (Weidle, Auer et al. 2013). Most of them fold properly under non-reducing conditions and can be expressed in bacteria without the need for denaturation and refolding. Even chemical synthesis is an option for the production of some of the formats. Finally, they are well-suited for further functionalization (labelling, oligomerization, fusion with other peptides, etc.) to generate multi-functional binding molecules. Among the different scaffold-based approaches cystine-knot miniproteins ("knottins") have shown great potential for the development of targeted diagnostics and therapeutics agents. For example, Cochran and co-workers generated radiolabeled miniproteins, 18F-FP-2.5D and 18F-FP-2.5F, for integrin-specific PET imaging of U87MG tumors, marked by good contrast, fast tumor targeting, rapid clearance from the body and relatively low uptake in normal tissues (Kimura, Cheng et al. 2009, Kimura, Levin et al. 2009, Kimura, Miao et al. 2010, Kimura, Jones et al. 2011, Liu, Liu et al. 2011). Miniproteins are small, 30-50 amino acid polypeptides containing three disulfide bonds that form the eponymous knotted structure (Kolmar 2009, Moore and Cochran 2012). The pseudoknot cystine topology is responsible for an extraordinary thermal, proteolytic and chemical stability, which is desirable for in vivo biomedical applications (Kolmar 2011). For example, without losing structural and functional integrity, miniproteins can be boiled in alkaline or acidic environment (Weidle, Auer et al. 2013). The disulfide-constrained loop regions tolerate broad sequence diversity, providing a robust molecular framework for engineering proteins that recognize a variety of biomedical targets.

There is a need in the art for Seprase binding molecules which are useful in diagnostic and therapeutic approaches for tumors expressing Seprase.

Seprase binding agents such as Seprase binding peptides are described herein which show high specificity and selectivity for human Seprase. The Seprase binding agents described herein are excellent tools for diagnostic applications, particularly for tumor imaging, and therapeutic applications by efficient targeting of the tumor microenvironment.

DESCRIPTION OF INVENTION

Summary of the Invention

According to the invention, an open-chain variant of the knottin-type trypsin inhibitor II from *Momordica cochinchinensis* (oMCoTI-II) was used as a molecular scaffold for engineering a Seprase specific binding protein for tumor targeting applications. To this end, a combinatorial phage library was utilized for the selection of oMCoTI-II variants specifically interacting with the extracellular domain of recombinant human Seprase. One of the identified knottin peptides (miniproteins) showing binding to the predefined target, MC-FA-010 (aa: GKCPYSNWTPGRGP-DCRRDSDCPGRCICRGNGYCG), was characterized in more detail. It shows specific complexing of human Seprase, whereas related proteins such as the closely related homologue DPP-IV is not recognized. Binding is mainly dependent on two aliphatic residues and a GRGP motive in the first loop of MC-FA-010 which could be shown by alanine scanning mutagenesis. Furthermore, the Seprase specific miniprotein is cross-reactive with the murine homologue as determined by flow cytometry and whole-cell-ELISA using target positive CHO-K1 cell lines. Specific targeting of Seprase expressed by cancer-associated-fibroblasts (CAFs) could be shown by Immunofluorescence staining of CT26 tumor sections. In vivo targeting of neoplastic tissue could be demonstrated in Fox n1 (nu) mice bearing target positive CHO-K1 tumors.

The present invention generally provides compounds useful for the treatment and/or diagnosis of cancer diseases by targeting Seprase. These compounds provide for the selective detection of cells expressing Seprase and/or eradication of cells expressing Seprase and/or of cells that are associated with cells expressing Seprase thereby minimizing adverse effects to normal cells not expressing Seprase.

The present invention provides a Seprase binding peptide which comprises the amino acid sequence Gly Arg Gly Pro.

In a first embodiment, the Seprase binding peptide of the invention comprises the amino acid sequence:

Tyr Xaa1 Xaa2 Trp Xaa3 Xaa4 Gly Arg Gly Pro wherein
Xaa1 is any amino acid, preferably an amino acid selected from the group consisting of Ser, Ala and Cys, more preferably an amino acid selected from the group consisting of Ser and Ala, more preferably Ser,
Xaa2 is any amino acid, preferably an amino acid selected from the group consisting of Asn, Ala and Asp, more preferably an amino acid selected from the group consisting of Asn and Ala, more preferably Asn,
Xaa3 is any amino acid, preferably an amino acid selected from the group consisting of Thr, Ala and Val, more preferably an amino acid selected from the group consisting of Thr and Ala, more preferably Thr,
Xaa4 is any amino acid, preferably an amino acid selected from the group consisting of Pro and Ala, more preferably Pro.

In a preferred embodiment, the Seprase binding peptide comprises the amino acid sequence:

Tyr Xaa1 Asn Trp Thr Pro Gly Arg Gly Pro wherein
Xaa1 is any amino acid, preferably an amino acid selected from the group consisting of Ser, Ala and Cys, more preferably an amino acid selected from the group consisting of Ser and Ala, more preferably Ser.

In a preferred embodiment, the Seprase binding peptide comprises the amino acid sequence:

Tyr Ser Asn Trp Thr Pro Gly Arg Gly Pro.

In a second embodiment, the Seprase binding peptide of the invention comprises the amino acid sequence:

Xaa1 Tyr Xaa2 Xaa3 Trp Xaa4 Xaa5 Gly Arg Gly Pro wherein
Xaa1 is any amino acid, preferably an amino acid selected from the group consisting of Pro and Ala, more preferably Pro
Xaa2 is any amino acid, preferably an amino acid selected from the group consisting of Ser, Ala and Cys, more preferably an amino acid selected from the group consisting of Ser and Ala, more preferably Ser,
Xaa3 is any amino acid, preferably an amino acid selected from the group consisting of Asn, Ala and Asp, more preferably an amino acid selected from the group consisting of Asn and Ala, more preferably Asn,
Xaa4 is any amino acid, preferably an amino acid selected from the group consisting of Thr, Ala and Val, more preferably an amino acid selected from the group consisting of Thr and Ala, more preferably Thr,
Xaa5 is any amino acid, preferably an amino acid selected from the group consisting of Pro and Ala, more preferably Pro.

In a preferred embodiment, the Seprase binding peptide comprises the amino acid sequence:

Pro Tyr Xaa1 Asn Trp Thr Pro Gly Arg Gly Pro wherein

Xaa1 is any amino acid, preferably an amino acid selected from the group consisting of Ser, Ala and Cys, more preferably an amino acid selected from the group consisting of Ser and Ala, more In a preferred embodiment, the Seprase binding peptide comprises the amino acid sequence:

Cys Pro Tyr Ser Asn Trp Thr Pro Gly Arg Gly Pro Asp Cys.

In a further embodiment, the Seprase binding peptide of the invention comprises the amino acid sequence:

(Xaa)n1 Cys (Xaa)n2 Gly Arg Gly Pro (Xaa)n3 Cys (Xaa)n4 Cys (Xaa)n5 Cys (Xaa)n6 Cys (Xaa)n7 Cys (Xaa)n8 wherein
the Cys residues form a cysteine knot structure,
Xaa is independently from each other any amino acid and n1, n2, n3, n4, n5, n6, n7, and n8 are the respective numbers of amino acids,
wherein the nature of the amino acids Xaa and/or the number of amino acids n1, n2, n3, n4, n5, n6, n7 and n8 are such that a cysteine knot structure can form between the Cys residues,
wherein preferably
n1 is 0 to 4, preferably 1 or 2,
n2 is 3 to 10, preferably 6, 7 or 8,
n3 is 0 to 4, preferably 1 or 2,
n4 is 3 to 7, preferably 4, 5 or 6,
n5 is 2 to 6, preferably 2, 3 or 4,
n6 is 1 to 3, preferably 1 or 2,
n7 is 3 to 7, preferably 4, 5 or 6, and
n8 is 0 to 4, preferably 1 or 2.

In a further embodiment, the Seprase binding peptide of the invention comprises the amino acid sequence:

Cys Xaa1 Tyr Xaa2 Xaa3 Trp Xaa4 Xaa5 Gly Arg Gly Pro Xaa6 Cys Arg Arg Asp Ser Asp Cys Pro Gly Xaa7 Cys Ile Cys Arg Gly Asn Gly Tyr Cys wherein
Xaa1 is any amino acid, preferably an amino acid selected from the group consisting of Pro and Ala, more preferably Pro,
Xaa2 is any amino acid, preferably an amino acid selected from the group consisting of Ser, Ala and Cys, more preferably an amino acid selected from the group consisting of Ser and Ala, more preferably Ser,
Xaa3 is any amino acid, preferably an amino acid selected from the group consisting of Asn, Ala and Asp, more preferably an amino acid selected from the group consisting of Asn and Ala, more preferably Asn,
Xaa4 is any amino acid, preferably an amino acid selected from the group consisting of Thr, Ala and Val, more preferably an amino acid selected from the group consisting of Thr and Ala, more preferably Thr,
Xaa5 is any amino acid, preferably an amino acid selected from the group consisting of Pro and Ala, more preferably Pro,
Xaa6 is any amino acid, preferably an amino acid selected from the group consisting of Asp, Ala and Asn, more preferably an amino acid selected from the group consisting of Asp and Ala, more preferably Asp, Xaa7 is any amino acid, preferably an amino acid selected from the group consisting of Arg and Ala, more preferably Arg.

In a preferred embodiment, the Seprase binding peptide comprises the amino acid sequence:

Cys Pro Tyr Xaa1 Asn Trp Thr Pro Gly Arg Gly Pro Xaa2 Cys Arg Arg Asp Ser Asp Cys Pro Gly Xaa3 Cys Ile Cys Arg Gly Asn Gly Tyr Cys wherein
Xaa1 is any amino acid, preferably an amino acid selected from the group consisting of Ser, Ala and Cys, more preferably an amino acid selected from the group consisting of Ser and Ala, more preferably Ser,
Xaa2 is any amino acid, preferably an amino acid selected from the group consisting of Asp, Ala and Asn, more preferably an amino acid selected from the group consisting of Asp and Ala, more preferably Asp,
Xaa3 is any amino acid, preferably an amino acid selected from the group consisting of Arg and Ala, more preferably Arg.

In a preferred embodiment, the Seprase binding peptide comprises the amino acid sequence:

Cys Pro Tyr Ser Asn Trp Thr Pro Gly Arg Gly Pro Asp Cys Arg Arg Asp Ser Asp Cys Pro Gly Arg Cys Ile Cys Arg Gly Asn Gly Tyr Cys.

In a further embodiment, the Seprase binding peptide of the invention comprises the amino acid sequence:

Xaa1 Xaa2 Cys Xaa3 Tyr Xaa4 Xaa5 Trp Xaa6 Xaa7 Gly Arg Gly Pro Xaa8 Cys Arg Arg Asp Ser Asp Cys Pro Gly Xaa9 Cys Ile Cys Arg Gly Asn Gly Tyr Cys Gly wherein
Xaa1 is any amino acid, preferably an amino acid selected from the group consisting of Gly and Ala, more preferably Gly,
Xaa2 is any amino acid, preferably an amino acid selected from the group consisting of Lys and Ala,
Xaa3 is any amino acid, preferably an amino acid selected from the group consisting of Pro and Ala, more preferably Pro,
Xaa4 is any amino acid, preferably an amino acid selected from the group consisting of Ser, Ala and Cys, more preferably an amino acid selected from the group consisting of Ser and Ala, more preferably Ser,
Xaa5 is any amino acid, preferably an amino acid selected from the group consisting of Asn, Ala and Asp, more preferably an amino acid selected from the group consisting of Asn and Ala, more preferably Asn,
Xaa6 is any amino acid, preferably an amino acid selected from the group consisting of Thr, Ala and Val, more preferably an amino acid selected from the group consisting of Thr and Ala, more preferably Thr,
Xaa7 is any amino acid, preferably an amino acid selected from the group consisting of Pro and Ala, more preferably Pro,
Xaa8 is any amino acid, preferably an amino acid selected from the group consisting of Asp, Ala and Asn, more preferably an amino acid selected from the group consisting of Asp and Ala, more preferably Asp, Xaa9 is any amino acid, preferably an amino acid selected from the group consisting of Arg and Ala, more preferably Arg.

In a preferred embodiment, the Seprase binding peptide comprises the amino acid sequence:

Xaa1 Xaa2 Cys Pro Tyr Xaa3 Asn Trp Thr Pro Gly Arg

Gly Pro Xaa4 Cys Arg Arg Asp Ser Asp Cys Pro Gly

Xaa5 Cys Ile Cys Arg Gly Asn Gly Tyr Cys Gly wherein

Xaa1 is any amino acid, preferably an amino acid selected from the group consisting of Gly and Ala, more preferably Gly, Xaa2 is any amino acid, preferably an amino acid selected from the group consisting of Lys and Ala, Xaa3 is any amino acid, preferably an amino acid selected from the group consisting of Ser, Ala and Cys, more preferably an amino acid selected from the group consisting of Ser and Ala, more preferably Ser, Xaa4 is any amino acid, preferably an amino acid selected from the group consisting of Asp, Ala and Asn, more preferably an amino acid selected from the group consisting of Asp and Ala, more preferably Asp, Xaa5 is any amino acid, preferably an amino acid selected from the group consisting of Arg and Ala, more preferably Arg.

In a preferred embodiment, the Seprase binding peptide comprises the amino acid sequence:

Gly Lys Cys Pro Tyr Ser Asn Trp Thr Pro Gly Arg

Gly Pro Asp Cys Arg Arg Asp Ser Asp Cys Pro Gly

Arg Cys Ile Cys Arg Gly Asn Gly Tyr Cys Gly.

In a preferred embodiment, the Seprase binding peptide comprises the amino acid sequence:

Gly Ala Cys Pro Tyr Ser Asn Trp Thr Pro Gly Arg

Gly Pro Asp Cys Arg Arg Asp Ser Asp Cys Pro Gly

Arg Cys Ile Cys Arg Gly Asn Gly Tyr Cys Gly.

In one embodiment, the Seprase binding peptide comprises an amino acid sequence shown below in Table 1, Table 2 or Table 4. In one embodiment, the Seprase binding peptide comprises an amino acid sequence shown in SEQ ID NO: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 85, 86, 87, 88, 89, 90, 91, 92, 93, 94, 95, or 96 of the sequence listing.

In one embodiment, the Seprase binding peptide of the invention forms or is part of a scaffold. The term "scaffold" relates to a structure conferring rigidity to the Seprase binding peptide or amino acid sequence described herein.

In one embodiment, the Seprase binding peptide of the invention is stabilized by a covalent modification. In one embodiment, said covalent modification is cyclization. In one embodiment, said cyclization is via one or more disulfide bridges.

In one embodiment, the Seprase binding peptide of the invention forms and/or is part of a cystine knot structure, preferably inhibitor cystine knot structure. In one embodiment, the cystine knot structure is based on the open chain trypsin inhibitor II from *Momordica cochinchinensis* (MCoTI-II), trypsin inhibitor EETI-II of *Ecballium elaterium* and an optimized MCoTI-II scaffold.

The amino acid sequence Gly Arg Gly Pro and/or the amino acid sequence in the Seprase binding peptide of the first or second embodiment of the invention is preferably part of a cystine knot structure wherein the amino acid sequence is located within the first loop (i.e. between the first cysteine and the second cysteine) of the cystine knot structure.

In one embodiment, the Seprase binding peptide of the invention further comprises at least one fusion partner. In one embodiment, the fusion partner comprises a heterologous amino acid sequence.

The invention also provides a Seprase binding agent comprising one or more such as 2, 3, 4, 5, 6 or more Seprase binding peptides as described herein, wherein the Seprase binding peptides may be identical or different. The present invention also provides a Seprase binding agent comprising the Seprase binding peptide of the invention covalently and/or non-covalently, preferably covalently associated with at least one further moiety.

In one embodiment of the Seprase binding peptide of the invention or the Seprase binding agent of the invention the fusion partner or further moiety comprises a carrier protein, label, reporter, or tag. In one embodiment, the reporter is a reporter for an immunological assay, wherein the reporter preferably is selected from the group consisting of alkaline phosphatase, horseradish peroxidase, or a fluorescent molecule. In one embodiment, the fusion partner or further moiety is selected from the group consisting of a His6-cassette, thioredoxin, a S-tag, biotin or a combination thereof.

In one embodiment, the Seprase binding agent of the invention comprises at least two subunits which are covalently and/or non-covalently associated, each of said subunits comprising a Seprase binding peptide of the invention, wherein the Seprase binding peptides may be identical or different.

According to the invention, in one embodiment, non-covalent association is via a compound comprising streptavidin. According to the invention, in one embodiment, covalent association is via peptidic and/or non-peptidic linkers.

Thus, in one embodiment, the Seprase binding peptide of the invention is present in oligomeric or multimeric form. In this embodiment, two or more Seprase binding peptides of the invention which may be identical or different may be linked or coupled by covalent or non-covalent bonding, such as through biotin/streptavidin. Thus, Seprase binding peptides of the invention may form dimers, trimers, tetramers etc.

In one embodiment, the Seprase binding agent of the invention comprises at least four subunits which are non-covalently associated.

In one embodiment, the Seprase binding agent of the invention comprises at least three subunits which are covalently associated.

In one embodiment, the Seprase binding agent of the invention comprises the Seprase binding peptide of the invention or the Seprase binding agent of the invention covalently and/or non-covalently, preferably covalently associated with at least one detectable label or reporter and/or at least one therapeutic effector moiety.

In one embodiment, the Seprase binding peptide of the invention or the Seprase binding agent of the invention binds to an extracellular domain of Seprase.

In one embodiment of the Seprase binding peptide of the invention or the Seprase binding agent of the invention said Seprase is expressed by cells.

In one embodiment, the Seprase binding peptide of the invention or the Seprase binding agent of the invention does not bind to DPP IV.

In one embodiment of the invention, binding is a specific binding.

The present invention also provides a recombinant nucleic acid which encodes a Seprase binding peptide of the invention. In one embodiment, the recombinant nucleic acid is in the form of a vector or in the form of RNA.

The present invention also provides a host cell comprising a recombinant nucleic acid of the invention.

Another object of the invention is to provide means and methods for diagnosis, detection or monitoring, i.e. determining the regression, progression, course and/or onset, of a cancer disease.

The present invention provides a test kit comprising the Seprase binding peptide of the invention or the Seprase binding agent of the invention. In one embodiment, the test kit further comprises at least one additional reagent for performing an immunoassay and/or instructions for use of the kit for performing an immunoassay. In one embodiment, the test kit of the invention is a diagnostic test kit.

Diagnostic test kits of the invention may be useful in the methods for diagnosis, detection or monitoring of cancer of the invention. These kits may include informative pamphlets, for example, pamphlets informing one how to use reagents to practice a method disclosed herein.

The present invention provides an assay device comprising the Seprase binding peptide of the invention or the Seprase binding agent of the invention. In one embodiment, the assay device is an enzyme-linked immunosorbent assay device. In one embodiment of the assay device of the invention, the Seprase binding peptide or Seprase binding agent is releasably or non-releasably immobilised on a solid support.

The present invention provides a method for assaying for the presence and/or amount of Seprase in a sample comprising using the Seprase binding peptide of the invention or the Seprase binding agent of the invention.

The present invention provides a method for diagnosis, detection or monitoring of cancer in a patient comprising assaying for the presence and/or amount of Seprase in said patient using the Seprase binding peptide of the invention or the Seprase binding agent of the invention In a particular aspect, the invention relates to a method for detection, i.e. determining the position or site, of a cancer disease, e.g. a particular tissue or organ. In one embodiment, said method comprises administering a Seprase binding compound of the invention which is coupled to a detectable label to a patient.

Labelling of a tissue or organ in said patient may indicate the presence of or risk for a cancer disease in said tissue or organ.

In one embodiment, the tissue or organ is a tissue or organ wherein the cells when the tissue or organ is free of cancer do not substantially express Seprase.

In one embodiment of the methods of the invention, said assaying is performed on a biological sample isolated from said patient.

In one embodiment, the biological sample is isolated from a patient having a cancer disease, being suspected of having or falling ill with a cancer disease or having a potential for a cancer disease. In one embodiment, the biological sample is from a tissue or organ wherein the cells when the tissue or organ is free of cancer do not substantially express Seprase.

Typically, the level of Seprase in a biological sample is compared to a reference level, wherein a deviation from said reference level is indicative of the presence and/or stage of a cancer disease in a patient. The reference level may be a level as determined in a control sample (e.g., from a healthy tissue or subject) or a median level from healthy subjects. A "deviation" from said reference level designates any significant change, such as an increase or decrease by at least 10%, 20%, or 30%, preferably by at least 40% or 50%, or even more. The presence of Seprase and/or a quantity of Seprase which is increased compared to a reference level, e.g. compared to a patient without a cancer disease, may indicate the presence of or risk for (i.e. a potential for a development of) a cancer disease in said patient.

In one embodiment, a biological sample and/or a control/reference sample is from a tissue or organ corresponding to the tissue or organ which is to be diagnosed, detected or monitored with respect to affection by a cancer disease; e.g. the cancer disease which is to be diagnosed, detected or monitored is brain cancer and the biological sample and/or control/reference sample is brain tissue.

In one embodiment, the biological sample and/or a control/reference sample is from a tissue or organ wherein the cells when the tissue or organ is free of cancer do not substantially express Seprase. The indication of the presence of or risk for a cancer disease in a patient by the methods of the invention may indicate that the cancer disease is in said tissue or organ or that said tissue or organ is at risk for said cancer disease.

The methods for diagnosis, detection or monitoring allow quantitative and/or qualitative evaluations, e.g., absolute and/or relative measure of target molecules, e.g. expression levels of Seprase.

Means for accomplishing said assaying for the presence and/or amount of Seprase are described herein and will be apparent to the skilled person. Typically, the assaying in the methods of the invention involves the use of labeled ligands which specifically bind to Separase, e.g. a compound of the invention that specifically binds to Seprase directly or indirectly bound to a label that provides for detection, e.g. indicator enzymes, radiolabels, fluorophores, or paramagnetic particles.

In one embodiment of the methods of the invention, the presence of Seprase or an amount of Seprase which is higher compared to a reference without cancer indicates that the patient has cancer.

The methods of monitoring according to the invention preferably comprise assaying for the presence and/or amount of Seprase in a first sample at a first point in time and in a further sample at a second point in time, wherein the regression, progression, course and/or onset of a cancer disease may be determined by comparing the two samples.

A quantity of Seprase which is decreased in a biological sample compared to a biological sample taken earlier from a patient may indicate a regression, a positive course, e.g. a successful treatment, or a reduced risk for an onset of a cancer disease in said patient.

A quantity of Seprase which is increased in a biological sample compared to a biological sample taken earlier from a patient may indicate a progression, a negative course, e.g.

an unsuccessful treatment, recurrence or metastatic behaviour, an onset or a risk for an onset of a cancer disease in said patient.

In one embodiment of the methods of the invention, assaying for the presence and/or amount of Seprase comprises:

(i) contacting the biological sample with the Seprase binding peptide of the invention or the Seprase binding agent of the invention, and (ii) detecting the formation of and/or determining the quantity of a complex between the Seprase binding peptide or the Seprase binding agent and Seprase.

In one embodiment of the methods of the invention, the Seprase binding peptide or Seprase binding agent comprises or is conjugated to at least one detectable label or reporter.

In one embodiment, the method of the invention is performed in the context of an immunoassay.

In one embodiment of the methods of the invention, the Seprase binding peptide or Seprase binding agent is releasably or non-releasably immobilised on a solid support.

Binding of a Seprase binding compound according to the invention to Seprase can interfere with the function of Seprase, e.g. by inhibiting catalytic activity. Furthermore, a Seprase binding compound may be attached to therapeutic effector moieties, e.g., radiolabels, cytotoxins, cytotoxic enzymes, and the like, and binding of the compound to Seprase can selectively target and kill cells that express Seprase or cells that are associated with cells that express Seprase, in particular cancer cells. In one embodiment, said compound reduces tumor cell growth and/or induces tumor cell death and thus, has a tumor-inhibiting or tumor-destroying effect. Accordingly, the Seprase binding compounds described herein may be used in therapy, in particular for a prophylactic and/or therapeutic treatment of cancer diseases.

A positive diagnosis of a cancer disease as described above using the methods of the present invention may indicate a cancer disease which is amenable to the methods of treatment described herein.

Thus, another object of the invention is to provide means and methods for therapeutic and/or prophylactic treatment of a cancer disease.

The present invention provides a pharmaceutical composition comprising the Seprase binding peptide of the invention, the Seprase binding agent of the invention, the recombinant nucleic acid of the invention or the host cell of the invention.

A pharmaceutical composition of the invention may comprise a pharmaceutically acceptable carrier and may optionally comprise further substances as described herein.

The present invention provides the Seprase binding peptide of the invention, the Seprase binding agent of the invention, the recombinant nucleic acid of the invention, the host cell of the invention or the pharmaceutical composition of the invention for use in therapy, in particular for use in treating or preventing cancer in a patient.

The present invention provides the Seprase binding peptide of the invention or the Seprase binding agent of the invention for use in targeting cancer in a patient.

The present invention provides a method of treating a patient comprising administering to the patient the Seprase binding peptide of the invention, the Seprase binding agent of the invention, the recombinant nucleic acid of the invention, the host cell of the invention or the pharmaceutical composition of the invention, wherein, preferably, the patient has cancer or is at risk of developing cancer.

In one embodiment of the above aspects, the Seprase binding peptide or Seprase binding agent comprises or is conjugated to at least one therapeutic effector moiety.

In one embodiment of the above aspects, the cancer is Seprase-positive and/or involves cells expressing Seprase. In one embodiment, the cells are cancer-associated fibroblasts.

According to all aspects of the invention, cancer is preferably selected from the group consisting of breast cancer, pulmonary or lung cancer, e.g. non-small cell lung carcinoma (NSCLC), colorectal cancer, colon cancer, esophagus cancer, head and neck cancer, stomach cancer, bile duct cancer, pancreas cancer, kidney cancer, cervix cancer, ovary cancer, bladder cancer, endometrium cancer or prostate cancer.

According to all aspects of the invention, Seprase preferably comprises the amino acid sequence according to SEQ ID NO: 3 or 4 of the sequence listing or a variant of said amino acid sequence.

In one aspect, the invention provides agents as described herein for use in the methods of treatment described herein. In one embodiment, the invention provides a pharmaceutical composition as described herein for use in the methods of treatment described herein.

The treatments described herein can be combined with surgical resection and/or radiation and/or traditional chemotherapy.

Other features and advantages of the instant invention will be apparent from the following detailed description and claims.

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, cell biology, immunology, and recombinant DNA techniques which are explained in the literature in the field (cf., e.g., *Molecular Cloning: A Laboratory Manual*, 2nd Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The present invention relates to Seprase binding compounds or agents such as Seprase binding peptides or agents comprising one or more Seprase binding peptides.

Seprase also known as fibroblast activation protein alpha (FAPα) or 170 kDa melanoma membrane-bound gelatinase is a protein that in humans is encoded by the FAP gene. The protein is an integral membrane serine peptidase, which has been shown to have gelatinase activity.

Seprase appears to act as a proteolytically active 170 kDa homodimer, consisting of two 97 kDa subunits. It is a member of the group type II integral serine proteases, which include dipeptidyl peptidase IV (DPP IV/CD26) and related type II transmembrane prolyl serine peptidases, which exert their mechanisms of action on the cell surface. Seprase is a member of the S9B prolyl oligopeptidase subfamily. Other members of the S9B subfamily are DPP IV, DPP8 and DPP9.

Seprase is most closely related to DPP IV and they share about 50% of their amino acids. DPP IV and Seprase exhibit multiple functions due to their abilities to form complexes with each other and to interact with other membrane associated molecules.

Seprase has a dual function in tumor progression. The proteolytic activity of Seprase has been shown to promote cell invasiveness towards the extracellular matrix and also to support tumor growth and proliferation. It is selectively expressed in reactive stromal fibroblasts of epithelial cancers, granulation tissue of healing wounds, and malignant cells of bone and soft tissue sarcomas. Seprase expression is seen on activated stromal fibroblasts of more than 90% of all human carcinomas. Stromal fibroblasts play an important role in the development, growth and metastasis of carcinomas.

According to the invention, the term "Seprase" preferably relates to human Seprase.

Preferably, the term "Seprase" relates to a nucleic acid comprising, preferably consisting of the nucleic acid sequence of SEQ ID NO: 1 or 2 of the sequence listing or a variant of said nucleic acid sequence and to a protein encoded by this nucleic acid, preferably to a protein comprising, preferably consisting of the amino acid sequence of SEQ ID NO: 3 or 4 of the sequence listing or a variant of said amino acid sequence.

The amino acid sequence of Seprase predicts a type II integral membrane protein with a cytoplasmic tail of 6 amino acids, followed by a transmembrane domain of 20 amino acids and an extracellular domain of 734 amino acids. The carboxyl terminus contains a putative catalytic region (~200 amino acids) which is homologous (68% identity) to that of the nonclassical serine protease dipeptidyl peptidase IV (DPP IV). The conserved serine protease motif G-X-S-X-G is present as G-W-S-Y-G.

Seprase is expressed in cancers of various origins such as breast cancer, pulmonary or lung cancer, e.g. non-small cell lung carcinoma (NSCLC), colorectal cancer, colon cancer, esophagus cancer, head and neck cancer, stomach cancer, bile duct cancer, pancreas cancer, kidney cancer, cervix cancer, ovary cancer, bladder cancer, endometrium cancer or prostate cancer. Seprase is a valuable target for the diagnosis, prevention and/or treatment of primary tumors and metastases.

A Seprase binding agent of the invention has the ability of binding to Seprase, i.e. the ability of binding to an epitope present in Seprase, preferably an epitope located within the extracellular domains of Seprase, in particular amino acid positions 27 to 760 of Seprase. In particular embodiments, a Seprase binding agent of the invention binds to an epitope on Seprase which is not present on DPP IV.

A Seprase binding agent preferably binds to Seprase but not to DPP IV. Preferably, a Seprase binding agent is specific for Seprase. Preferably, a Seprase binding agent binds to Seprase expressed on the cell surface. In particular preferred embodiments, a Seprase binding agent binds to native epitopes of Seprase present on the surface of living cells.

The term "epitope" refers to a part or portion in a molecule that is recognized by a binding agent. For example, epitopes are the discrete, three-dimensional sites on a molecule, which are recognized by a binding agent. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. An epitope of a protein preferably comprises a continuous or discontinuous portion of said protein and is preferably between 5 and 100, preferably between 5 and 50, more preferably between 8 and 30, most preferably between 10 and 25 amino acids in length, for example, the epitope may be preferably 8, 9, 10, 11, 12, 13, 14, 15, 16, 17, 18, 19, 20, 21, 22, 23, 24, or 25 amino acids in length.

According to the invention, the term "Seprase binding agent" or "Seprase binding compound" includes any compound (including complexes of molecules) that has a binding capacity to Seprase. Preferably, such binding agent is or comprises at least one Seprase binding peptide of the invention. If a Seprase binding agent comprises at least two Seprase binding peptides of the invention (which may be identical or different) these peptides may be covalently or non-covalently associated (i.e., bound). Seprase binding agents may comprise one or more Seprase binding peptides covalently or non-covalently associated to any other compound or moiety such as labels or therapeutic effector moieties.

According to the present invention, an agent is capable of binding to a predetermined target such as Seprase if it has a significant affinity for said predetermined target and binds to said predetermined target in standard assays. "Affinity" or "binding affinity" is often measured by equilibrium dissociation constant ($K_D$). Preferably, the term "significant affinity" refers to the binding to a predetermined target with a dissociation constant ($K_D$) of $10^{-5}$ M or lower, $10^{-6}$ M or lower, $10^{-7}$ M or lower, $10^{-8}$ M or lower, $10^{-9}$ M or lower, $10^{-10}$ M or lower, $10^{-11}$ M or lower, or $10^{-12}$ M or lower.

An agent is not (substantially) capable of binding to a target if it has no significant affinity for said target and does not bind significantly, in particular does not bind detectably, to said target in standard assays. Preferably, the agent does not detectably bind to said target if present in a concentration of up to 2, preferably 10, more preferably 20, in particular 50 or 100 µg/ml or higher. Preferably, an agent has no significant affinity for a target if it binds to said target with a $K_D$ that is at least 10-fold, $10^2$-fold, $10^3$-fold, $10^4$-fold, $10^5$-fold, or $10^6$-fold higher than the $K_D$ for binding to the predetermined target to which the agent is capable of binding. For example, if the $K_D$ for binding of an agent to the target to which the agent is capable of binding is $10^{-7}$ M, the $K_D$ for binding to a target for which the agent has no significant affinity would be at least $10^{-6}$ M, $10^{-5}$ M, $10^{-4}$ M, $10^{-3}$ M, $10^{-2}$ M, or $10^{-1}$ M.

According to the invention, the term "binding" preferably relates to a specific binding.

"Specific binding" means that an agent binds stronger to a target for which it is specific compared to the binding to another target. An agent binds stronger to a first target compared to a second target if it binds to the first target with a dissociation constant ($K_D$) which is lower than the dissociation constant for the second target. Preferably the dissociation constant ($K_D$) for the target to which the agent binds specifically is more than $10^2$-fold, $10^3$-fold, $10^4$-fold, $10^5$-fold, $10^6$-fold, $10^7$-fold, $10^8$-fold, $10^9$-fold, or $10^{10}$-fold lower than the dissociation constant ($K_D$) for the target to which the agent does not bind specifically.

Preferably, an agent is specific for a predetermined target if it is capable of binding to said predetermined target while it is not capable of binding to other targets, i.e. has no significant affinity for other targets and does not significantly bind to other targets in standard assays. According to the invention, an agent is specific for Seprase if it is capable of binding to Seprase but is not (substantially) capable of binding to other targets such as DPP IV. Preferably, an agent is specific for Seprase if the affinity for and the binding to such other targets does not significantly exceed the affinity for or binding to Seprase-unrelated proteins such as bovine serum albumin (BSA), casein, human serum albumin (HSA) or non-Seprase transmembrane proteins such as MHC molecules or transferrin receptor or any other specified polypeptide. Preferably, an agent is specific for a predetermined target if it binds to said target with a $K_D$ that is at least $10^2$-fold, $10^3$-fold, $10^4$-fold, $10^5$-fold, $10^6$-fold, $10^7$-fold, $10^8$-fold, $10^9$-fold, or $10^{10}$-fold lower than the $K_D$ for binding to a target for which it is not specific.

Binding of an agent to a target can be determined experimentally using any suitable method; see, for example, Berzofsky et al., "Antibody-Antigen Interactions" In Fundamental Immunology, Paul, W. E., Ed., Raven Press New York, N Y (1984), Kuby, Janis Immunology, W. H. Freeman and Company New York, N Y (1992), and methods described herein. Affinities may be readily determined using conventional techniques, such as by equilibrium dialysis; by using surface plasmon resonance analytic (e.g. Biacore), using general procedures outlined by the manufacturer; by radioimmunoassay using radiolabeled target antigen; or by another method known to the skilled artisan. The affinity data may be analyzed, for example, by the method of Scatchard et al., Ann N.Y. Acad. ScL, 51:660 (1949). The measured affinity of a particular interaction can vary if measured under different conditions, e.g., salt concentration, pH. Thus, measurements of affinity and other binding parameters, e.g., $K_D$, $IC_{50}$, are preferably made with standardized solutions of binding agent and target, and a standardized buffer.

According to the invention, the term "Seprase-positive cancer" or similar terms means a cancer involving or being associated with Seprase, in particular a cancer involving cells expressing Seprase, preferably on the surface of said cells.

According to the invention, a cancer involves or is associated with Seprase if Seprase is spatially linked to said cancer, in particular if Seprase is present in said cancer. Preferably, a cancer involving or being associated with Seprase contains cells expressing Seprase, preferably on the surface of said cells. Said cells may be cancer cells or cells being associated with cancer such as fibroblasts, in particular cancer-associated fibroblasts.

"Cell surface" is used in accordance with its normal meaning in the art, and thus includes the outside of the cell which is accessible to binding by proteins and other molecules Seprase is expressed on the surface of cells if it is located at the surface of said cells and is accessible to binding by Seprase-specific agents added to the cells.

The term "extracellular domain" in the context of the present invention refers to a portion of a molecule such as a protein that is facing the extracellular space of a cell and preferably is accessible from the outside of said cell, e.g., by binding agents such as antibodies located outside the cell. Preferably, the term refers to one or more extracellular loops or domains or a fragment thereof.

The terms "part" or "fragment" are used interchangeably herein and refer to a continuous element. A part or fragment of a protein sequence preferably comprises at least 6, in particular at least 8, at least 12, at least 15, at least 20, at least 30, at least 50, or at least 100 consecutive amino acids of the protein sequence.

The term "portion" refers to a continuous and/or non-continous element. A portion of a protein sequence preferably comprises at least 6, in particular at least 8, at least 12, at least 15, at least 20, at least 30, at least 50, or at least 100 consecutive and/or non-consecutive amino acids of the protein sequence.

According to the invention, Seprase is not (substantially) expressed in a cell if the level of expression is below the detection limit and/or if the level of expression is too low to allow binding by Seprase-specific binding agents added to the cell.

According to the invention, Seprase is expressed in a cell if the level of expression is above the detection limit and/or if the level of expression is high enough to allow binding by Seprase-specific binding agents added to the cell. Preferably, Seprase expressed in a cell is expressed or exposed on the surface of said cell.

A cystine knot is a protein structural motif containing at least three disulfide bridges (formed from pairs of cysteine molecules). It comprises an embedded ring formed by two disulfide bonds and their connecting backbone segments which is threaded by a third disulfide bond. This structure is preferably associated with a beta-sheet structure. Peptides containing a cystine knot are preferably 25-60, preferably 25-50 or 25-40 amino acid residues long.

Cystine knots occur in many peptides or proteins across many species and provide considerable structural stability. There are three types of cystine knots, which differ in the topology of the disulfide bonds: Growth Factor Cystine Knot (GFCK), Inhibitor Cystine Knot (ICK) and Cyclic Cystine Knot, or cyclotide.

An inhibitor cystine knot (ICK) or knottin is a protein structural motif containing three disulfide bridges. Along with the sections of polypeptide between them, two disulfides (linking the first and fourth cysteine and the second and fifth cysteine, respectively) form a loop through which the third disulfide bond (linking the third and sixth cysteine in the sequence) passes, forming a knot. The motif is common in invertebrate toxins such as those from arachnids and molluscs. The motif is also found in some inhibitor proteins found in plants.

Thus, according to the invention, an ICK motif involves two intracysteine backbone segments and their connecting disulfide bonds, CysI-CysIV and CysII-CysV, which form a ring that is penetrated by the third disulfide bond, CysIII-CysVI.

The ICK motif is similar to the cyclic cystine knot or cyclotide, but lacks the cyclisation of the polypeptide backbone which is present in the latter family. The growth factor cystine knot (GFCK) shares the motif but its topology is such that it is the bond between the first and fourth cysteine which threads through the loop (formed between the second and fifth cysteine and the third and sixth cysteine, respectively).

The cyclotides fall into two main structural subfamilies. Moebius cyclotides, the less common of the two, contain a cis-proline in loop 5 that induces a local 180° backbone twist, whereas bracelet cyclotides do not. The trypsin inhibitor cyclotides are classified in their own family based on sequence variation and natural activity. Trypsin inhibitor cyclotides are more homologous to a family of non-cyclic trypsin inhibitors from squash plants known as knottins or inhibitor cystine knots than they are to the other cyclotides.

MCoTI-I and MCoTI-II are natural polypeptides from the seeds of the spinal gourd *Momordica cochinchinensis*. These polypeptides are inhibitors of trypsin-like proteases and contain an additional loop connecting the amino- and the carboxy-terminus and a knotted arrangement of three conserved disulfide bonds. The cystine knot is defined by three intramolecular disulfide bonds, where CysICysIV and CysII-CysV of the linear peptide sequence form a ring that is penetrated by the third disulfide bond, CysIII-CysVI. This arrangement provides a well-defined and extremely stable scaffold that exhibits extraordinary thermal and proteolytic stability. Due to structural similarity and common biological activity, i.e., inhibition of proteases of the trypsin family, MCoTI-I and MCoTI-II have been grouped into the squash inhibitor cystine-knot (ICK) family of small protease inhibitors. Members of this family are open-chain molecules forming a small triple-stranded β-sheet and a short $3_{10}$ helix, held together by three intramolecular disulfide bonds to give rise to a cystine-knot framework. MCoTI-I and MCoTI-II are the only known members of the large family of squash inhibitors that are cyclic. Open-chain variants of MCoTI-II that lack the cyclization loop have been synthesized.

According to the invention, peptides described herein can be synthetically produced by chemical synthesis methods which are well known in the art, either as an isolated peptide or as a part of another peptide or polypeptide. Alternatively, a peptide can be produced in a microorganism which produces the peptide which is then isolated and if desired, further purified. Thus, the peptide can be produced in microorganisms such as bacteria, yeast, or fungi; in a eukaryote cells such as mammalian or insect cells; or, in a recombinant virus vector such as adenovirus, poxvirus, herpesvirus, Simliki forest virus, baculovirus, bacteriophage, sindbis virus, or sendai virus. Suitable bacteria for producing the peptide include *Escherichia coli, Bacillus subtilis*, or any other bacterium that is capable of expressing peptides. Suitable yeast types for expressing the peptide include, but are not limited to *Saccharomyces cerevisiae, Schizosaccharomyces pombe, Candida*, or any other yeast capable of expressing peptides. Methods for using the aforementioned bacteria, recombinant virus vectors, eukaryote cells to produce peptides are well known in the art.

To produce a peptide, the nucleic acid encoding the peptide is preferably in a plasmid and the nucleic acid is operably linked to a promoter which effects expression of the peptide in a microorganism. Suitable promoters include, but are not limited to, T7 phage promoter, T3 phage promoter, β-galactosidase promoter, and the Sp6 phage promoter. Methods for isolating and purifying peptides are well known in the art and include methods such as gel filtration, affinity chromatography, ion exchange chromatography, or centrifugation.

The peptides of the invention, either by themselves or as part of a fusion peptide, can be conjugated to a heterologous peptide or protein. Such heterologous proteins include, but are not limited to, carrier proteins such as bovine serum albumen (BSA), and reporter enzymes which include, but are not limited to, horseradish peroxidase or alkaline phosphatase. Further, the peptides or fusion peptides comprising the peptide can be chemically conjugated to fluorescent reporter molecules which include, but are not limited to, fluorescein or R-phycoerythrin. Methods for conjugating carrier proteins, enzymes, and fluorescent reporter molecules to peptides and fusion peptides are well known in the art.

To facilitate isolation of the peptide, a fusion polypeptide can be made wherein the peptide is translationally fused (covalently linked) to a heterologous tag such as a heterologous polypeptide or polyhistidine, preferably six histidine residues, which allows for the simplified recovery of the fusion polypeptide, e.g. its isolation by affinity chromatography or metal affinity chromatography, preferably nickel affinity chromatography. In some instances it can be desirable to remove the tag after purification. Therefore, it is also contemplated that the fusion polypeptide comprises a cleavage site at the junction between the peptide and the heterologous tag. The cleavage site consists of an amino acid sequence that is cleaved with an enzyme specific for the amino acid sequence at the site.

The Seprase binding agents described herein may be used in assays for assaying the presence or amount of Seprase or Seprase antibodies. Such assays may be carried out in a number of ways, including but not limited to immunodetection, and include ELISA, in particular peptide ELISA, competitive binding assays, RIA and the like. The methods of the invention allow quantitative and/or qualitative evaluations, e.g., absolute and/or relative evaluations, of Seprase or Seprase antibodies.

In general, the assays are performed using an enzyme-linked immunosorbent assay (ELISA) embodiment.

The term "enzyme-linked immunosorbent assay or ELISA", as used herein, relates to a method for quantitatively or semi-quantitatively determining protein concentrations from a sample, e.g. blood plasma, serum or cell/tissue extracts, in a multi-well plate format (usually 96-wells per plate). Broadly, proteins in solution are adsorbed to ELISA plates. Antibodies specific for the protein of interest may be used to probe the plate. Background is minimized by optimizing blocking and washing methods (as for IHC), and specificity is ensured via the presence of positive and negative controls. Detection methods are usually colorimetric or chemiluminescence based.

A microtiter plate may be provided containing a plurality of wells wherein a first well or series of wells contains a monoclonal antibody against Seprase immobilized to the surface therein. A sample may be added to the wells containing the bound monoclonal antibody. The Seprase in the sample binds to the monoclonal antibody. The ELISA is incubated for a time sufficient for antibody complexes to form. A peptide of the invention may be further added. The peptide may be part of a fusion polypeptide. Afterwards, the wells are washed to remove any unbound material. The wells may then be incubated with a labeled antibody or an antibody conjugated to a reporter molecule that binds to the fusion polypeptide to form a complex which can be detected. A detectable signal from the label or reporter indicates that the sample contains Seprase whereas an absence of a signal may indicate that the sample does not contain Seprase. When the fusion polypeptide comprises a label or reporter molecule such as a reporter enzyme such as alkaline phosphatase, the antibody complex can be detected directly without the need for a labeled antibody.

Alternatively, a microtiter plate may be provided containing a plurality of wells wherein a first well or series of wells contains the peptide of the invention, which may be conjugated to a carrier protein or fusion polypeptide, immobilized to the surface therein. Sample may be added to the wells containing the bound peptides. The Seprase in the sample and the peptide bound to the well surfaces are incubated for a time sufficient for complexes to form. Afterwards, the wells are washed to remove any unbound material. The amount of Seprase that is bound to the immobilized peptides in the well is determined by incubating the wells with a labeled antibody or an antibody conjugated to a reporter molecule that binds to the Seprase to form a complex that can be detected. A detectable signal from the reporter indicates the sample contains Seprase whereas an absence of a signal indicates that the sample does not contain Seprase. The intensity of the signal may provide an estimate of the concentration of Seprase in the sample.

According to the invention, the Seprase which is to be assayed may be expressed on the surface of a cell.

Peptides of the invention may also be used in methods for detecting the presence of antibodies against Seprase. The design of suitable immunoassays to put these methods into effect may be subject to a great deal of variation, and a variety of these immunoassays are known in the art. Suitable immunoassay protocols may be based, for example, upon competition, or direct reaction, or sandwich type assays. The immunoassay protocols used may also, for example, use solid supports, or may be by immunoprecipitation. Assays may involve the use of labelled peptides and the labels may be, for example, fluorescent, chemiluminescent, radioactive, or dye molecules. Particular preferred assays are enzyme-labelled and mediated immunoassays, such as ELISA assays.

Accordingly, the peptides may also be used in an assay such as an ELISA assay to determine antibody against Seprase in a sample. For this purpose, the wells of ELISA plates may be coated with peptides. Seprase and the peptide bound to the well surfaces may be incubated for a time sufficient for complexes to form. Subsequently, a sample such as plasma may be added and the detection of Seprase specific antibodies (primary antibody) may be performed with a labelled secondary antibody directed against the primary antibody.

When used as an assay reagent as described herein, a peptide of the invention may be conjugated to a label.

According to the invention, a label is any entity the presence of which can be readily detected. Preferably the label is a direct label. Direct labels are entities which, in their natural state, are readily visible either to the naked eye, or with the aid of an optical filter and/or applied stimulation, e.g. UV light to promote fluorescence. Examples include radioactive, chemiluminescent, electroactive (such as redox labels), and fluorescent compounds. Direct particulate labels, such as dye sols, metallic sols (e.g. gold) and coloured latex particles, are also very suitable and are, along with fluorescent compounds, preferred. Of these options, coloured latex particles and fluorescent compounds are most preferred. Concentration of the label into a small zone or volume should give rise to a readily detectable signal, e.g. a strongly coloured area. Indirect labels, such as enzymes, e.g. alkaline phosphatase and horseradish peroxidase, can also be used, although these usually require the addition of one or more developing reagents such as substrates before a visible signal can be detected.

According to the invention, a label may function to: (i) provide a detectable signal; (ii) interact with a second label to modify the detectable signal provided by the first or second label, e.g. FRET (Fluorescence Resonance Energy Transfer); (iii) affect mobility, e.g. electrophoretic mobility, by charge, hydrophobicity, shape, or other physical parameters, or (iv) provide a capture moiety, e.g., affinity, antibody/antigen, or ionic complexation. Suitable as label are structures, such as fluorescent labels, luminescent labels, chromophore labels, radioisotopic labels, isotopic labels, preferably stable isotopic labels, isobaric labels, enzyme labels, particle labels, in particular metal particle labels, magnetic particle labels, polymer particle labels, small organic molecules such as biotin, ligands of receptors or binding molecules such as cell adhesion proteins or lectins, label-sequences comprising nucleic acids and/or amino acid residues which can be detected by use of binding agents, etc. Labels comprise, in a nonlimiting manner, barium sulfate, iocetamic acid, iopanoic acid, calcium ipodate, sodium diatrizoate, meglumine diatrizoate, metrizamide, sodium tyropanoate and radio diagnostic, including positron emitters such as fluorine-18 and carbon-11, gamma emitters such as iodine-123, technetium-99m, iodine-131 and indium-111, nuclides for nuclear magnetic resonance, such as fluorine and gadolinium. In preferred embodiments, a label comprises a radionuclide such as lutetium-177 or gallium-68 which may be complexed with a ligand such as DOTA (1,4,7,10-tetraazacyclododecane-1,4,7,10-tetraacetic acid) bound to a Seprase binding agent.

Conjugation of the label to the peptide of the invention can be by covalent or non-covalent (including hydrophobic) bonding, or by adsorption. Techniques for such conjugation are commonplace in the art and may be readily adapted for the particular reagents employed.

The term "sample", as used herein, includes any biological sample which may be isolated from a patient and used for analysis purposes. Said sample may be a body fluid sample, a tissue sample, or a cell sample. For example, samples encompassed by the present invention are tissue (e.g. section or explant) samples, single cell samples, cell colony samples, cell culture samples, blood (e.g. whole blood or blood fraction such as blood cell fraction, serum or plasma) samples, urine samples, or samples from other peripheral sources. Said samples may be mixed or pooled, e.g. a sample may be a mixture of a blood sample and a urine sample. Said samples may be provided by removing a body fluid, cell(s), cell colonies, an explant, or a section from a patient, but may also be provided by using a previously isolated sample. For example, a tissue sample may be removed from a patient by conventional biopsy techniques or a blood sample may be taken from a patient by conventional blood collection techniques. The sample, e.g. tissue sample or blood sample, may be obtained from a patient prior to initiation of the therapeutic treatment, during the therapeutic treatment, and/or after the therapeutic treatment.

In one embodiment, the sample is a body fluid sample. The term "body fluid sample", as used herein, refers to any liquid sample derived from the body of a patient. Said body fluid sample may be a blood sample, urine sample, sputum sample, breast milk sample, cerebrospinal fluid (CSF) sample, cerumen (earwax) sample, endolymph sample, perilymph sample, gastric juice sample, mucus sample, peritoneal fluid sample, pleural fluid sample, saliva sample, sebum (skin oil) sample, semen sample, sweat sample, tears sample, vaginal secretion sample, or vomit sample including components or fractions thereof. Said body fluid samples may be mixed or pooled. Thus, a body fluid sample may be a mixture of a blood and a urine sample or a mixture of a blood and cerebrospinal fluid sample. Said body fluid sample may be provided by removing a body liquid from a patient, but may also be provided by using previously isolated body fluid sample material. In one preferred embodiment, the sample is a whole blood sample or a blood fraction sample such as a blood cell fraction, blood serum, or blood plasma sample.

In one embodiment, a biological sample is a sample obtained from a tissue suspected of being affected with a disease such as cancer. In one embodiment, a biological sample is a tumor sample, e.g. a sample obtained from a tumor and comprising tumor cells. According to the invention, the term "biological sample" also includes processed biological samples such as fractions or isolates of biological samples, e.g. nucleic acid and peptide/protein isolates.

According to the invention, a "reference" such as a reference sample or reference organism may be used to correlate and compare the results obtained in the methods of the invention from a test sample or test organism, i.e. a patient. Typically the reference organism is a healthy organism, in particular an organism which does not suffer from a tumor disease.

A "reference value" or "reference level" can be determined from a reference empirically by measuring a sufficiently large number of references. Preferably the reference value is determined by measuring at least 2, preferably at least 3, preferably at least 5, preferably at least 8, preferably at least 12, preferably at least 20, preferably at least 30, preferably at least 50, or preferably at least 100 references.

"Reduce", "decrease" or "inhibit" as used herein means an overall decrease or the ability to cause an overall decrease, preferably of 5% or greater, 10% or greater, 20% or greater, more preferably of 50% or greater, and most preferably of 75% or greater, in the level, e.g. in the level of expression or in the level of proliferation of cells. The amount of a substance is also reduced in a test sample such as a biological sample compared to a reference sample if it is detectable in the reference sample but absent or not detectable in the test sample.

Terms such as "increase" or "enhance" preferably relate to an increase or enhancement by about at least 10%, preferably at least 20%, preferably at least 30%, more preferably at least 40%, more preferably at least 50%, even more preferably at least 80%, and most preferably at least 100%, at least 200%, at least 500%, at least 1000%, at least 10000% or even more. The amount of a substance is also increased in a test sample such as a biological sample compared to a reference sample if it is detectable in the test sample but absent or not detectable in the reference sample.

Seprase binding agents such as peptides of the invention may be bound to a solid support, for example the surface of an immunoassay well or dipstick, and/or packaged into kits in a suitable container along with suitable reagents, controls, instructions and the like.

Accordingly the present invention also provides a kit comprising at least one Seprase binding agent of the present invention. In a preferred embodiment, the kit further comprises at least one additional agent such as one or more suitable reagents for performing an immunoassay, a control, or instructions for use of the kit.

According to the invention there is further provided an assay device comprising at least one Seprase binding agent of the present invention. In one embodiment, the assay device is selected from the group consisting of an enzyme-linked immunosorbent assay device.

Such a device can take different forms, and it can be varied depending on the precise nature of the assay being performed. For example, the peptide of the invention may be coated onto a solid support, typically nitrocellulose or other hydrophobic porous material. Alternatively, the peptide may be coated on a synthetic plastics material, microtitre assay plate, microarray chip, latex bead, filter comprising a cellulosic or synthetic polymeric material, glass or plastic slide, dipstick, capillary fill device and the like. Coating of the peptides to these surfaces can be accomplished by methods known in the art. Protein carriers are typically used for complexing, with BSA or adhesive peptides being the most preferred. In one embodiment, the peptide of the invention is releasably immobilised on the solid support. In a further preferred embodiment, the peptide of the invention is non-releasably immobilised on the solid support.

It is to be understood that the peptides described herein may be delivered to a patient by administering a nucleic acid such as RNA encoding the peptide and/or by administering a host cell comprising a nucleic acid such as RNA encoding the peptide. Thus, a nucleic acid encoding a peptide when administered to a patient may be present in naked form or in a suitable delivery vehicle such as in the form of liposomes or viral particles, or within a host cell. The nucleic acid provided can produce the peptide over extended time periods in a sustained manner. Nucleic acids to be delivered to a patient can be produced by recombinant means. If a nucleic acid is administered to a patient without being present within a host cell, it is preferably taken up by cells of the patient for expression of the peptide encoded by the nucleic acid. If a nucleic acid is administered to a patient while being present within a host cell, it is preferably expressed by the host cell within the patient so as to produce the peptide encoded by the nucleic acid.

The term "nucleic acid", as used herein, is intended to include deoxyribonucleic acid (DNA) and ribonucleic acid (RNA) such as genomic DNA, cDNA, mRNA, recombinantly produced and chemically synthesized molecules. A nucleic acid may be single-stranded or double-stranded. RNA includes in vitro transcribed RNA (IVT RNA) or synthetic RNA.

As used herein, the term "RNA" means a molecule comprising ribonucleotide residues. By "ribonucleotide" is meant a nucleotide with a hydroxyl group at the 2'-position of a beta-D-ribo-furanose moiety. The term includes double stranded RNA, single stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

According to the present invention, the term "RNA" includes and preferably relates to "mRNA" which means "messenger RNA" and relates to a "transcript" which may be produced using DNA as template and encodes a peptide or protein. mRNA typically comprises a 5' non translated region (5'-UTR), a protein or peptide coding region and a 3' non translated region (3'-UTR). In one embodiment of the invention, the RNA is obtained by in vitro transcription or chemical synthesis. Preferably, mRNA is produced by in vitro transcription using a DNA template. The in vitro transcription methodology is known to the skilled person. For example, there is a variety of in vitro transcription kits commercially available.

In order to increase expression and/or stability of the RNA used according to the present invention, it may be modified, preferably without altering the sequence of the expressed peptide or protein.

The term "modification" in the context of RNA as used according to the present invention includes any modification of RNA which is not naturally present in said RNA.

In one embodiment of the invention, the RNA used according to the invention does not have uncapped 5'-triphosphates. Removal of such uncapped 5'-triphosphates can be achieved by treating RNA with a phosphatase.

The RNA according to the invention may have modified naturally occurring or synthetic ribonucleotides in order to increase its stability and/or decrease cytotoxicity. For example, in one embodiment, in the RNA used according to the invention 5-methylcytidine is substituted partially or completely, preferably completely, for cytidine. Alternatively or additionally, in one embodiment, in the RNA used according to the invention pseudouridine is substituted partially or completely, preferably completely, for uridine.

In one embodiment, the term "modification" relates to providing an RNA with a 5'-cap or 5'-cap analog. The term "5'-cap" refers to a cap structure found on the 5'-end of an mRNA molecule and generally consists of a guanosine nucleotide connected to the mRNA via an unusual 5' to 5' triphosphate linkage. In one embodiment, this guanosine is methylated at the 7-position. The term "conventional 5'-cap" refers to a naturally occurring RNA 5'-cap, preferably to the 7-methylguanosine cap (m7G). In the context of the present invention, the term "5'-cap" includes a 5'-cap analog that resembles the RNA cap structure and is modified to possess the ability to stabilize RNA if attached thereto, preferably in vivo and/or in a cell.

Providing an RNA with a 5'-cap or 5'-cap analog may be achieved by in vitro transcription of a DNA template in the presence of said 5'-cap or 5'-cap analog, wherein said 5'-cap is co-transcriptionally incorporated into the generated RNA strand, or the RNA may be generated, for example, by in vitro transcription, and the 5'-cap may be attached to the RNA post-transcriptionally using capping enzymes, for example, capping enzymes of vaccinia virus.

The RNA may comprise further modifications. For example, a further modification of the RNA used in the present invention may be an extension or truncation of the naturally occurring poly(A) tail or an alteration of the 5'- or 3'-untranslated regions (UTR) such as introduction of a UTR which is not related to the coding region of said RNA, for example, the insertion of one or more, preferably two copies of a 3'-UTR derived from a globin gene, such as alpha2-globin, alpha1-globin, beta-globin, preferably beta-globin, more preferably human beta-globin.

In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector".

The term "translation" according to the invention relates to the process in the ribosomes of a cell by which a strand of messenger RNA directs the assembly of a sequence of amino acids to make a peptide or protein.

The term "expression" is used according to the invention in its most general meaning and comprises the production of RNA and/or peptides or proteins, e.g. by transcription and/or translation. With respect to RNA, the term "expression" or "translation" relates in particular to the production of peptides or proteins. It also comprises partial expression of nucleic acids. Moreover, expression can be transient or stable. According to the invention, the term expression also includes an "aberrant expression" or "abnormal expression".

"Aberrant expression" or "abnormal expression" means according to the invention that expression is altered, preferably increased, compared to a reference, e.g. a state in a subject not having a disease associated with aberrant or abnormal expression of a certain protein, e.g., Seprase. An increase in expression refers to an increase by at least 10%, in particular at least 20%, at least 50%, at least 100%, at least 200%, at least 500%, at least 1000%, at least 10000%, or more. In one embodiment, expression is only found in a diseased tissue, while expression in a healthy tissue is repressed.

The term "specifically expressed" means that a protein is essentially only expressed in a specific tissue or organ. For example, a protein specifically expressed in gastric mucosa means that said protein is primarily expressed in gastric mucosa and is not expressed in other tissues or is not expressed to a significant extent in other tissue or organ types. Thus, a protein that is exclusively expressed in cells of the gastric mucosa and to a significantly lesser extent in any other tissue, such as testis, is specifically expressed in cells of the gastric mucosa.

According to the invention, the term "nucleic acid encoding" means that nucleic acid, if present in the appropriate environment, preferably within a cell, can be expressed to produce a protein or peptide it encodes.

The nucleic acids described according to the invention have preferably been isolated. The term "isolated nucleic acid" means according to the invention that the nucleic acid was (i) amplified in vitro, for example by polymerase chain reaction (PCR), (ii) recombinantly produced by cloning, (iii) purified, for example by cleavage and gel-electrophoretic fractionation, or (iv) synthesized, for example by chemical synthesis. An isolated nucleic acid is a nucleic acid which is available for manipulation by recombinant DNA techniques.

The term "variant" with respect to, for example, nucleic acid and amino acid sequences, according to the invention includes any variants, in particular mutants, splice variants, conformations, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. A species homolog is a nucleic acid or amino acid sequence with a different species of origin from that of a given nucleic acid or amino acid sequence.

With respect to nucleic acid molecules, the term "variant" includes degenerate nucleic acid sequences, wherein a degenerate nucleic acid according to the invention is a nucleic acid that differs from a reference nucleic acid in codon sequence due to the degeneracy of the genetic code.

Furthermore, a "variant" of a specific nucleic acid sequence according to the invention includes nucleic acid sequences comprising single or multiple such as at least 2, at least 4, or at least 6 and preferably up to 3, up to 4, up to 5, up to 6, up to 10, up to 15, or up to 20 nucleotide substitutions, deletions and/or additions.

Preferably the degree of identity between a given nucleic acid sequence and a nucleic acid sequence which is a variant of said given nucleic acid sequence will be at least about 60%, 65%, 70%, 80%, 81%, 82%, 83%, 84%, 85%, 86%, 87%, 88%, 89%, 90%, 91%, 92%, 93%, 94%, 95%, 96%, 97%, 98%, or 99%. The degree of identity is given preferably for a region which is at least about 10%, at least about 20%, at least about 30%, at least about 40%, at least about 50%, at least about 60%, at least about 70%, at least about 80%, at least about 90% or about 100% of the entire length of the reference nucleic acid sequence. For example, if the reference nucleic acid sequence consists of 200 nucleotides, the degree of similarity or identity is given preferably for at least about 20, at least about 40, at least about 60, at least about 80, at least about 100, at least about 120, at least about 140, at least about 160, at least about 180, or about 200 nucleotides, preferably continuous nucleotides. In preferred embodiments, the degree of identity is given for the entire length of the reference nucleic acid sequence.

"Sequence identity" between two nucleic acid sequences indicates the percentage of nucleotides that are identical between the sequences.

The term "percentage identity" is intended to denote a percentage of nucleotides which are identical between the two sequences to be compared, obtained after the best alignment, this percentage being purely statistical and the differences between the two sequences being distributed randomly and over their entire length. Sequence comparisons between two nucleotide sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

Preferably, a given nucleic acid sequence and a nucleic acid sequence which is a variant of said given nucleic acid sequence will be capable of hybridizing.

A nucleic acid is "capable of hybridizing" or "hybridizes" to another nucleic acid if the two sequences are complementary with one another. A nucleic acid is "complementary" to another nucleic acid if the two sequences are capable of forming a stable duplex with one another. According to the invention, hybridization is preferably carried out under conditions which allow specific hybridization between polynucleotides (stringent conditions). Stringent conditions are described, for example, in Molecular Cloning: A Laboratory Manual, J. Sambrook et al., Editors, 2nd Edition, Cold Spring Harbor Laboratory press, Cold Spring Harbor, New York, 1989 or Current Protocols in Molecular Biology, F. M. Ausubel et al., Editors, John Wiley & Sons, Inc., New York and refer, for example, to hybridization at 65° C. in hybridization buffer (3.5×SSC, 0.02% Ficoll, 0.02% polyvinylpyrrolidone, 0.02% bovine serum albumin, 2.5 mM $NaH_2PO_4$ (pH 7), 0.5% SDS, 2 mM EDTA). SSC is 0.15 M sodium chloride/0.15 M sodium citrate, pH 7. After hybridization, the membrane to which the DNA has been transferred is washed, for example, in 2×SSC at room temperature and then in 0.1-0.5×SSC/0.1×SDS at temperatures of up to 68° C.

A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" or "fully complementary" means that all the contiguous residues of a nucleic acid sequence will hydrogen bond with the same number of contiguous residues in a second nucleic acid sequence. Preferably, the degree of complementarity according to the invention is at least 70%, preferably at least 75%, preferably at least 80%, more preferably at least 85%, even more preferably at least 90% or most preferably at least 95%, 96%, 97%, 98% or 99%. Most preferably, the degree of complementarity according to the invention is 100%.

The term "derivative" comprises any chemical derivatization of a nucleic acid on a nucleotide base, on the sugar or on the phosphate. The term "derivative" also comprises nucleic acids which contain nucleotides and nucleotide analogs not occurring naturally. Preferably, a derivatization of a nucleic acid increases its stability.

Nucleic acids may, according to the invention, be present alone or in combination with other nucleic acids, in particular heterologous nucleic acids. Preferably, a nucleic acid coding for a peptide or protein expresses said peptide or protein. In preferred embodiments, a nucleic acid is functionally linked to expression control sequences or regulatory sequences which may be homologous or heterologous with respect to said nucleic acid. A coding sequence and a regulatory sequence are "functionally" linked to one another, if they are covalently linked to one another in such a way that expression or transcription of said coding sequence is under the control or under the influence of said regulatory sequence. If the coding sequence is to be translated into a functional protein, then, with a regulatory sequence functionally linked to said coding sequence, induction of said regulatory sequence results in transcription of said coding sequence, without causing a frame shift in the coding sequence or said coding sequence not being capable of being translated into the desired protein or peptide.

The term "expression control sequence" or "regulatory sequence" comprises according to the invention promoters, enhancers and other control elements which regulate expression of a gene. In particular embodiments of the invention, the expression control sequences can be regulated. The exact structure of regulatory sequences may vary as a function of the species or cell type, but generally comprises 5'untranscribed and 5'untranslated sequences which are involved in initiation of transcription and translation, respectively, such as TATA box, capping sequence, CAAT sequence, and the like. More specifically, 5'untranscribed regulatory sequences comprise a promoter region which includes a promoter sequence for transcriptional control of the functionally linked gene. Regulatory sequences may also comprise enhancer sequences or upstream activator sequences.

According to the invention, a nucleic acid may furthermore be present in combination with another nucleic acid which codes for a peptide controlling secretion of the protein or peptide encoded by said nucleic acid from a host cell. According to the invention, a nucleic acid may also be present in combination with another nucleic acid which codes for a peptide causing the encoded protein or peptide to be anchored on the cell membrane of the host cell or compartmentalized into particular organelles of said cell. Similarly, a combination with a nucleic acid is possible which represents a reporter gene or any "tag".

In a preferred embodiment, a recombinant nucleic acid molecule is according to the invention a vector, where appropriate with a promoter, which controls expression of a nucleic acid. The term "vector" is used here in its most general meaning and comprises any intermediary vehicle for a nucleic acid which enables said nucleic acid, for example, to be introduced into prokaryotic and/or eukaryotic cells and, where appropriate, to be integrated into a genome. Vectors of this kind are preferably replicated and/or expressed in the cells. An intermediary vehicle may be adapted, for example, to the use in electroporation, in bombardment with microprojectiles, in liposomal administration, in the transfer with the aid of agrobacteria or in insertion via DNA or RNA viruses. Vectors comprise plasmids, phagemids, bacteriophages or viral genomes.

The nucleic acids according to the invention may be used for transfection of host cells. Nucleic acids here mean both recombinant DNA and RNA. Recombinant RNA may be prepared by in-vitro transcription of a DNA template. Furthermore, it may be modified by stabilizing sequences, capping and polyadenylation prior to application.

The term "recombinant" in the context of the present invention means "made through genetic engineering". Preferably, a "recombinant object" such as a recombinant nucleic acid in the context of the present invention is not occurring naturally.

The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring.

The term "cell" or "host cell" preferably relates to an intact cell, i.e. a cell with an intact membrane that has not released its normal intracellular components such as enzymes, organelles, or genetic material. An intact cell preferably is a viable cell, i.e. a living cell capable of carrying out its normal metabolic functions. Preferably said term relates according to the invention to any cell which can be transfected with an exogenous nucleic acid. Preferably, the cell when transfected with an exogenous nucleic acid can express the nucleic acid.

The term "host cell" comprises according to the invention prokaryotic (e.g. E. coli) or eukaryotic cells (e.g. dendritic cells, B cells, CHO cells, COS cells, K562 cells, yeast cells and insect cells). Particular preference is given to mammalian cells such as cells from humans, mice, hamsters, pigs, goats, primates. The cells may be derived from a multiplicity of tissue types and comprise primary cells and cell lines. Specific examples comprise keratinocytes, peripheral blood leukocytes, stem cells of the bone marrow and embryonic stem cells. A nucleic acid may be present in the host cell in the form of a single copy or of two or more copies and, in one embodiment, is expressed in the host cell.

The term "peptide" comprises oligo- and polypeptides and refers to substances comprising two or more, preferably 3 or more, preferably 4 or more, preferably 6 or more, preferably 8 or more, preferably 10 or more, preferably 13 or more, preferably 16 more, preferably 21 or more and up to preferably 8, 10, 20, 30, 40 or 50, in particular 100 amino acids joined covalently by peptide bonds. The term "protein" refers to large peptides, preferably to peptides with more than 100 amino acid residues, but in general the terms "peptides" and "proteins" are synonyms and are used interchangeably herein.

According to the invention, a peptide may include natural amino acids and non-natural amino acids. In one embodiment, a peptide merely includes natural amino acids.

According to the invention, the term "non-natural amino acid" refers to an amino acid having a structure different from those of the 20 natural amino acid species. Since non-natural amino acids have structures similar to those of natural amino acids, non-natural amino acids may be classified as derivatives or analogs of given natural amino acids.

According to the invention, the term "cyclic peptide" relates to a peptide or polypeptide chain which forms a ring. A peptide can be cyclized in four different ways: head-to-tail (C-terminus to N-terminus), head-to-side chain, side chain-to-tail or side-chain-to-side-chain. Particularly preferred according to the invention are peptides containing two or more residues containing thiol groups such as cysteines which can form intramolecular disulphide bridges giving cyclic peptides.

According to the invention, a peptide may be covalently or non-covalently bound to one or more other compounds. Such compounds include peptidic compound such as peptides and proteins as well as non-peptidic compounds such as polyethylene glycol (PEG).

In one embodiment, the peptides described herein are PEGylated. PEGylation is the process of covalent attachment of polyethylene glycol (PEG) polymer chains to another molecule, such as a peptide or protein. The covalent attachment of PEG can "mask" the agent from the host's immune system (reduced immunogenicity and antigenicity), and increase the hydrodynamic size (size in solution) of the agent which prolongs its circulatory time by reducing renal clearance. PEGylation can also provide water solubility to hydrophobic drugs and proteins.

Preferably, the proteins and peptides described according to the invention have been isolated. The terms "isolated protein" or "isolated peptide" mean that the protein or peptide has been separated from its natural environment. An isolated protein or peptide may be in an essentially purified state. The term "essentially purified" means that the protein or peptide is essentially free of other substances with which it is associated in nature or in vivo. Such proteins and peptides may be used, for example, in an immunological or diagnostic assay or as therapeutics. Proteins and peptides described according to the invention may be isolated from biological samples such as tissue or cell homogenates and may also be expressed recombinantly in a multiplicity of pro- or eukaryotic expression systems.

The term "antibody" includes a glycoprotein comprising at least two heavy (H) chains and two light (L) chains inter-connected by disulfide bonds, and any molecule comprising an antigen-binding portion of such glycoprotein. The term "antibody" includes monoclonal antibodies, recombinant antibodies, human antibodies, humanized antibodies, chimeric antibodies, molecules comprising binding fragments or derivatives of antibodies, including, without limitation, single chain antibodies, e.g., scFv's and antigen-binding antibody fragments such as Fab and Fab' fragments and also includes all recombinant forms of antibodies, e.g., antibodies expressed in prokaryotes, unglycosylated antibodies, and any antigen-binding antibody fragments and derivatives as described herein. Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The teaching given herein with respect to specific amino acid sequences, e.g. those shown in the sequence listing, is to be construed so as to also relate to variants of said specific sequences resulting in sequences which are functionally equivalent to said specific sequences, e.g. amino acid sequences exhibiting properties identical or similar to those of the specific amino acid sequences. One important property is to retain binding to a target such as Seprase.

For the purposes of the present invention, "variants" of an amino acid sequence comprise amino acid insertion variants, amino acid addition variants, amino acid deletion variants and/or amino acid substitution variants. Amino acid deletion variants that comprise the deletion at the N-terminal and/or C-terminal end of the protein are also called N-terminal and/or C-terminal truncation variants.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid addition variants comprise amino- and/or carboxy-terminal fusions of one or more amino acids, such as 1, 2, 3, 5, 10, 20, 30, 50, or more amino acids.

Amino acid deletion variants are characterized by the removal of one or more amino acids from the sequence, such as by removal of 1, 2, 3, 5, 10, 20, 30, 50, or more amino acids. The deletions may be in any position of the peptide or protein.

Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties. Preferably, amino acid changes in protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids.

Preferably the degree of similarity, preferably identity between a given amino acid sequence and an amino acid sequence which is a variant of said given amino acid sequence will be at least about 60%, 65%, 70%, 80%, 81%, 82%, 83%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, preferably continuous amino acids. In preferred embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5.

"Sequence similarity" indicates the percentage of amino acids that either are identical or that represent conservative amino acid substitutions. "Sequence identity" between two amino acid sequences indicates the percentage of amino acids that are identical between the sequences.

The term "percentage identity" is intended to denote a percentage of amino acid residues which are identical between the two sequences to be compared, obtained after the best alignment, this percentage being purely statistical and the differences between the two sequences being distributed randomly and over their entire length. Sequence comparisons between two amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

The peptides and amino acid variants described herein may be readily prepared with the aid of known peptide synthesis techniques such as, for example, by solid phase synthesis (Merrifield, 1964) and similar methods or by recombinant DNA manipulation. The manipulation of DNA sequences for preparing proteins and peptides having substitutions, insertions or deletions, is described in detail in Sambrook et al. (1989), for example.

According to the invention, the term "peptide" or "protein" includes "derivatives" of peptides and proteins. Such derivatives are modified forms of peptides and proteins. Such modifications include any chemical modification and comprise single or multiple substitutions, deletions and/or additions of any molecules associated with the peptide or protein, such as carbohydrates, lipids, proteins and/or peptides. The term "derivative" also extends to all functional chemical equivalents of said peptides and proteins. Preferably, a modified peptide has increased stability and/or increased immunogenicity.

The Seprase binding agents of the invention may be used in therapeutic approaches. To this end, the Seprase binding agents of the invention may be covalently and/or non-covalently bound to one or more therapeutic effector moieties and/or combined with various components to produce pharmaceutically acceptable compositions. The agents such as peptide described herein may be administered in the form of any suitable pharmaceutical composition.

"Target cell" shall mean any undesirable cell such as a cancer cell. In preferred embodiments, the target cell expresses Seprase.

According to the invention, the term "therapeutic effector moiety" means any molecule which may exert a therapeutic effect. According to the invention, a therapeutic effector moiety is preferably selectively guided to a cell which expresses Seprase. Any agent that exerts a therapeutic effect on cancer cells can be used as the drug for conjugation to a Seprase binding agent. Preferably, conjugation of the drug does not alter or significantly alter the binding characteristics, in particular the specificity, of the Seprase binding agent, as discussed herein.

According to the invention, a therapeutic effector moiety includes anticancer agents, radioisotopes such as radioactive iodine-labeled compounds, toxins, cytostatic or cytolytic drugs, etc. Anticancer agents comprise, for example, aminoglutethimide, azathioprine, bleomycin sulfate, busulfan, carmustine, chlorambucil, cisplatin, cyclophosphamide, cyclosporine, cytarabidine, dacarbazine, dactinomycin, daunorubin, doxorubicin, taxol, etoposide, fluorouracil, interferon-α, lomustine, mercaptopurine, methotrexate, mitotane, procarbazine HCl, thioguanine, vinblastine sulfate and vincristine sulfate. Other anticancer agents are described, for example, in Goodman and Gilman, "The Pharmacological Basis of Therapeutics", 8th Edition, 1990, McGraw-Hill, Inc., in particular Chapter 52 (Antineoplastic Agents (Paul Calabresi and Bruce A. Chabner). Toxins may be proteins such as pokeweed antiviral protein, cholera toxin, pertussis toxin, ricin, gelonin, abrin, diphtheria exotoxin or *Pseudomonas* exotoxin. Toxin residues may also be high energy-emitting radionuclides such as cobalt-60.

Therapeutic effector moieties include, in particular, cytotoxins or cytotoxic agents. A cytotoxin or cytotoxic agent includes any agent that is detrimental to and, in particular, kills cells.

Useful classes of cytotoxic agents include, for example, antitubulin agents, DNA minor groove binders (e.g., enediynes and lexitropsins), DNA replication inhibitors, aikylating agents (e.g., platinum complexes such as cis-platin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, nitrosoureas, platinols, pre-forming compounds, purine antimetabolites, puromycins, radiation sensitizers, steroids, taxanes (e.g., paclitaxel and docetaxel), topoisomerase inhibitors, *vinca* alkaloids, or the like.

Individual cytotoxic agents include, for example, an androgen, anthramycin (AMC), asparaginase, 5-azacytidine, azathioprine, bleomycin, busulfan, buthionine sulfoximine, camptothecin, carboplatin, carmustine (BSNU), CC-1065, chlorambucil, cisplatin, colchicine, cyclophosphamide, cytarabine, cytidine arabinoside, cytochalasin B, dacarbazine, dactinomycin (formerly actinomycin), daunorubicin, decarbazine, docetaxel, doxorubicin, an estrogen, 5-fluordeoxyuridine, 5-fluorouracil, gramicidin D, hydroxyurea, idarubicin, ifosfamide, irinotecan, lomustine (CCNU), mechlorethamine, melphalan, 6-mercaptopurine, methotrexate, mithramycin, mitomycin C, mitoxantrone, nitroimidazole, paclitaxel, plicamycin, procarbizine, streptozotocin, tenoposide, 6-thioguanine, thioTEPA, topotecan, vinblastine, vincristine, vinorelbine, VP-16 and VM-26.

Examples of anti-tubulin agents include, but are not limited to, dolastatins (e.g., auristatin E, AFP, MMAF, MMAE, AEB, AEVB), maytansinoids, taxanes (e.g., paclitaxel, docetaxel), T67 (Tularik), vinca alkyloids (e.g., vincristine, vinblastine, vindesine, and vinorelbine), baccatin derivatives, taxane analogs (e.g., epothilone A and B), nocodazole, colchicine and colcimid, estramustine, cryptophysins, cemadotin, combretastatins, discodermolide, and eleutherobin.

Radioisotopes to generate cytotoxic radiopharmaceuticals include, e.g., iodine-131, yttrium-90 or indium-111.

Techniques for conjugating such therapeutic effector moiety (drug) to peptides are well known. The generation of peptide-drug conjugates can be accomplished by any technique known to the skilled artisan. A peptide and a drug may be directly bound to each other via their own linker groups or indirectly via a linker or other substance.

A number of different reactions are available for covalent attachment of drugs to peptides. This is often accomplished by reaction of the amino acid residues of the peptide molecule, including the amine groups of lysine, the free carboxylic acid groups of glutamic and aspartic acid, the sulthydryl groups of cysteine and the various moieties of the aromatic amino acids. One of the most commonly used non-specific methods of covalent attachment is the carbodiimide reaction to link a carboxy (or amino) group of a compound to amino (or carboxy) groups of the peptide. Additionally, bifunctional agents such as dialdehydes or imidoesters have been used to link the amino group of a compound to amino groups of the peptide molecule. Also available for attachment of drugs to peptides is the Schiff base reaction. This method involves the periodate oxidation of a drug that contains glycol or hydroxy groups, thus forming an aldehyde which is then reacted with the peptide molecule. Attachment occurs via formation of a Schiff base with amino groups of the peptide molecule. Isothiocyanates can also be used as coupling agents for covalently attaching drugs to peptides. Other techniques are known to the skilled artisan and within the scope of the present invention.

There are many linking groups known in the art for making peptide-drug conjugates. A linker preferably comprises one or more functional groups that react with either or both of the peptide and the drug. Examples of functional groups include amino, carboxyl, mercapto, maleimide, and pyridinyl groups.

In one embodiment of the invention, a peptide is linked with a drug via a bifunctional crosslinking reagent. As used herein, a "bifunctional crosslinking reagent" refers to a reagent that possesses two reactive groups one of which is capable of reacting with a peptide, while the other one is capable of reacting with the drug to link the peptide with the drug, thereby forming a conjugate. Any suitable bifunctional crosslinking reagent can be used in connection with the invention, so long as the linker reagent provides for retention of the drug, e.g., cytotoxicity, and targeting characteristics of the peptide. Preferably, the linker molecule joins the drug to the peptide through chemical bonds, such that the drug and the peptide are chemically coupled (e.g., covalently bonded) to each other.

In one embodiment, the bifunctional crosslinking reagent comprises non-cleavable linkers. A non-cleavable linker is any chemical moiety that is capable of linking a drug to a peptide in a stable, covalent manner. Preferably, a non-cleavable linker is not cleavable under physiological conditions, in particular inside the body and/or inside a cell. Thus, non-cleavable linkers are substantially resistant to acid-induced cleavage, light-induced cleavage, peptidase-induced cleavage, esterase-induced cleavage, and disulfide bond cleavage, at conditions under which the drug or the peptide remains active. Suitable crosslinking reagents that form non-cleavable linkers between a drug and a peptide are well known in the art. In one embodiment, the drug is linked to the peptide through a thioether bond.

In one particularly preferred embodiment, the linking reagent is a cleavable linker. Preferably, a cleavable linker is cleavable under physiological conditions, in particular inside the body and/or inside a cell. Examples of suitable cleavable linkers include disulfide linkers, acid labile linkers, photolabile linkers, peptidase labile linkers, and esterase labile linkers.

Examples of linkers include, but are not limited to, N-succinimidyl-3-(2-pyridyldithio)butyrate (SPDB), N-succinimidyl-3-(2-pyridyldithio)propionate (SPDP), sulfosuccinimidyl-4-(N-maleimidomethyl)cyclohexane-1-carboxylate (Sulfo-SMCC), N-succinimidyl-4-(maleimidomethyl) cyclohexanecarboxylate (SMCC), N-succinimidyl-4-(N-maleimidomethyl)-cyclohexane-1-carboxy-(6-amidocaproate) (LC-SMCC), 4-maleimidobutyric acid N-hydroxysuccinimide ester (GMBS), 3-maleimidocaproic acid N-hydroxysuccinimide ester (EMCS), m-maleimidobenzoyl-N-hydroxysuccinimide ester (MBS), N-($\alpha$-maleimidoacetoxy)-succinimide ester (AMAS), succinimidyl-6-($\beta$-maleimidopropionamido)hexanoate (SMPH), N-succinimidyl-4-(p-maleimidophenyl)-butyrate (SMPB), N-(p-maleimidophenyl)isocyanate (PMPI), 6-maleimidocaproyl (MC), maleimidopropanoyl (MP), p-aminobenzyloxycarbonyl (PAB), N-succinimidyl-4-(2-pyridylthio)pentanoate (SPP), and N-succinimidyi (4-iodoacetyl) aminobenzoate (SIAB). A peptide linker such as valine-citrulline (Val-Cit) or alanine-phenylalanine (ala-phe) may also be used, and any of the aforementioned linkers may be used in adequate combination.

Disulfide containing linkers are linkers cleavable through disulfide exchange, which can occur under physiological conditions. In yet other embodiments, the linker is cleavable under reducing conditions (e.g., a disulfide linker). A variety of disulfide linkers are known in the art, including, for example, those that can be formed using SATA (N-succinimidyl-5-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene).

Acid labile linkers are linkers cleavable at acid pH. For example, certain intracellular compartments, such as endosomes and lysosomes, have an acidic pH (pH 4-5), and provide conditions suitable to cleave acid labile linkers. Acid labile linkers are relatively stable under neutral pH conditions, such as those in the blood, but are unstable at below pH 5.5 or 5.0. For example, a hydrazone, semicarbazone, thiosemicarbazone, cis-aconitic amide, orthoester, acetal, ketal, or the like can be used.

Photolabile linkers are useful at the body surface and in many body cavities that are accessible to light. Furthermore, infrared light can penetrate tissue.

Peptidase labile linkers can be used to cleave certain peptides inside or outside cells. In one embodiment, the cleavable linker is cleaved under mild conditions, i.e., conditions within a cell under which the activity of the cytotoxic agent is not affected.

The linker can be or can comprise, e.g., a peptidyl linker that is cleaved by an intracellular peptidase or protease enzyme, including, but not limited to, a lysosomal or endosomal protease. Typically, the peptidyl linker is at least two amino acids long or at least three amino acids long. Cleaving agents can include cathepsins B and D and plasmin, all of which are known to hydrolyze dipeptide drug derivatives resulting in the release of active drug inside target cells. For example, a peptidyl linker that is cleavable by the thiol-dependent protease cathepsin-B, which is highly expressed in cancerous tissue, can be used (e.g., a Phe-Leu or a Gly-Phe-Leu-Gly linker). In specific embodiments, the peptidyl linker cleavable by an intracellular protease is a valine-citrulline (Val-Cit; vc) linker or a phenylalanine-lysine (Phe-Lys) linker. One advantage of using intracellular proteolytic release of the therapeutic agent is that the agent is typically attenuated when conjugated and the serum stabilities of the conjugates are typically high.

The terms "individual" and "subject" are used herein interchangeably. They refer to human beings, non-human primates or other mammals (e.g. mouse, rat, rabbit, dog, cat, cattle, swine, sheep, horse or primate) that can be afflicted with or are susceptible to a disease or disorder (e.g., cancer) but may or may not have the disease or disorder. In many embodiments, the individual is a human being. Unless otherwise stated, the terms "individual" and "subject" do not denote a particular age, and thus encompass adults, elderlies, children, and newborns. In preferred embodiments of the present invention, the "individual" or "subject" is a "patient". The term "patient" means according to the invention a subject for treatment, in particular a diseased subject.

The term "disease" refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases. In humans, "disease" is often used more broadly to refer to any condition that causes pain, dysfunction, distress, social problems, or death to the individual afflicted, or similar problems for those in contact with the individual. In this broader sense, it sometimes includes injuries, disabilities, disorders, syndromes, infections, isolated symptoms, deviant behaviors, and atypical variations of structure and function, while in other contexts and for other purposes these may be considered distinguishable categories. Diseases usually affect individuals not only physically, but also emotionally, as contracting and living with many diseases can alter one's perspective on life, and one's personality. According to the invention, the term "disease" includes cancer, in particular those forms of cancer described herein. Any reference herein to cancer or particular forms of cancer also includes cancer metastasis thereof. In a preferred embodiment, a disease to be treated according to the present application involves cells expressing Seprase.

"Diseases involving cells expressing Seprase" or similar expressions means according to the invention that Seprase is expressed in cells of a diseased tissue or organ. In one embodiment, expression of Seprase in cells of a diseased tissue or organ is increased compared to the state in a healthy tissue or organ. In one embodiment, expression is only found in a diseased tissue, while expression in a healthy tissue is repressed. According to the invention, diseases involving cells expressing Seprase include cancer diseases. Furthermore, according to the invention, cancer diseases preferably are those wherein cells express Seprase.

The terms "cancer disease" or "cancer" refer to or describe the physiological condition in an individual that is typically characterized by unregulated cell growth. Examples of cancers include, but are not limited to, carcinoma, lymphoma, blastoma, sarcoma, and leukemia. More particularly, examples of such cancers include bone cancer, blood cancer, lung cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, prostate cancer, uterine cancer, carcinoma of the sexual and reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma. The term "cancer" according to the invention also comprises cancer metastases. Preferably, a "cancer disease" is characterized by cells expressing Seprase.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system. In one embodiment, the term "metastasis" according to the invention relates to lymph node metastasis.

According to the invention, the term "tumor" or "tumor disease" refers to an abnormal growth of cells (called neoplastic cells, tumorigenous cells or tumor cells) preferably forming a swelling or lesion. By "tumor cell" is meant an abnormal cell that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign, premalignant or malignant. According to the invention, a "cancer disease" preferably is a "tumor disease". However, generally, the terms "cancer" and "tumor" are used interchangeably herein.

Preferably, a tumor disease according to the invention is a cancer disease, i.e. a malignant disease, and a tumor cell is a cancer cell. Preferably, a tumor disease or cancer disease is characterized by cells in which Seprase is expressed or abnormally expressed and/or a tumor cell or cancer cell is characterized by expression or abnormal expression of Seprase.

A relapse or recurrence occurs when a person is affected again by a condition that affected them in the past. For example, if a patient has suffered from a tumor disease, has received a successful treatment of said disease and again develops said disease said newly developed disease may be considered as relapse or recurrence. However, according to the invention, a relapse or recurrence of a tumor disease may but does not necessarily occur at the site of the original tumor disease. A relapse or recurrence of a tumor also includes situations wherein a tumor occurs at a site different to the site of the original tumor as well as at the site of the original tumor. Preferably, the original tumor for which the patient has received a treatment is a primary tumor and the tumor at a site different to the site of the original tumor is a secondary or metastatic tumor.

The term "treatment" or "therapeutic treatment" relates to any treatment which improves the health status and/or prolongs (increases) the lifespan of an individual. Said treatment may eliminate the disease in an individual, arrest or slow the development of a disease in an individual, inhibit or slow the development of a disease in an individual, decrease the frequency or severity of symptoms in an individual, and/or decrease the recurrence in an individual who currently has or who previously has had a disease.

The terms "prophylactic treatment" or "preventive treatment" relate to any treatment that is intended to prevent a disease from occurring in an individual. The terms "prophylactic treatment" or "preventive treatment" are used herein interchangeably. For example, a subject at risk for cancer would be a candidate for therapy to prevent cancer.

By "being at risk" is meant a subject that is identified as having a higher than normal chance of developing a disease, in particular cancer, compared to the general population. In addition, a subject who has had, or who currently has, a disease, in particular cancer, is a subject who has an increased risk for developing a disease, as such a subject may continue to develop a disease. Subjects who currently have, or who have had, a cancer also have an increased risk for cancer metastases.

A (therapeutic) treatment of cancer may be selected from the group consisting of surgery, chemotherapy, radiation therapy and targeted therapy.

The term "surgery", as used herein, includes the removal of tumors in an operation. It is a common treatment for cancer. A surgeon may remove the tumors using local excision.

The term "chemotherapy", as used herein, refers to the use of chemotherapeutic agents or combinations of chemotherapeutic agents, preferably to stop the growth of cancer cells, either by killing the cells or by stopping them from dividing. When chemotherapy is taken by mouth or injected into a vein or muscle, the drugs enter the bloodstream and can reach cancer cells throughout the body (systemic chemotherapy). When chemotherapy is placed directly into the cerebrospinal fluid, an organ, or a body cavity such as the abdomen, the drugs mainly affect cancer cells in those areas (regional chemotherapy).

Chemotherapeutic agents according to the invention include cytostatic compounds and cytotoxic compounds. Traditional chemotherapeutic agents act by killing cells that divide rapidly, one of the main properties of most cancer cells. This means that chemotherapy also harms cells that divide rapidly under normal circumstances such as cells in the bone marrow, digestive tract, and hair follicles. This results in the most common side-effects of chemotherapy. Agents that target proteins that are abnormally expressed in a cancer (such as Seprase) and act through a therapeutic moiety or agent conjugated to the agent can be viewed as a form of chemotherapy. However, in the strictest sense, the term "chemotherapy" according to the invention does not include targeted therapy.

According to the invention, the term "targeted therapy" relates to any therapy that can be used to target preferentially diseased cells such as cancer cells while non-diseased cells are not targeted or targeted to a lesser extent. Targeting of diseased cells preferably results in killing and/or impairment of proliferation or viability of diseased cells. Such therapy includes i) agents that are conjugated to a therapeutic moiety that target certain cell surface targets, for example, Seprase, to deliver the therapeutic moiety (e.g. Seprase binding agents conjugated to a therapeutic moiety) or ii) agents that target certain cell surface targets, for example, Seprase, and impair proliferation or viability of diseased cells merely by binding thereto, (e.g. Seprase binding agents conjugated to a therapeutic moiety or not conjugated to a therapeutic moiety).

The pharmaceutical compositions and methods of treatment described according to the invention may be used to therapeutically treat or prevent a disease described herein. It is possible to use animal models for testing an effect on cancer. For example, human cancer cells may be introduced into a mouse to generate a tumor. The effect on the cancer cells (for example reduction in tumor size) may be measured as a measure for the effectiveness of an agent administered to the animal.

Peptides may be administered in a manner known per se. Generally, doses of a peptide of from 1 ng to 1 mg, preferably from 10 ng to 100 µg, are formulated and administered.

If the administration of nucleic acids (DNA and RNA) is desired, doses of from 1 ng to 0.1 mg may be formulated and administered.

In one embodiment, nucleic acids are administered by ex vivo methods, i.e. by removing cells from a patient, genetic modification of said cells in order to incorporate a nucleic acid and reintroduction of the altered cells into the patient. This generally comprises introducing a functional copy of a gene into the cells of a patient in vitro and reintroducing the genetically altered cells into the patient. The functional copy of the gene is under the functional control of regulatory elements which allow the gene to be expressed in the genetically altered cells. Transfection and transduction methods are known to the skilled worker.

The invention also provides for administering nucleic acids in vivo by using, for example, vectors such as viruses and target-controlled liposomes.

In a preferred embodiment, a virus or viral vector for administering a nucleic acid is selected from the group consisting of adenoviruses, adeno-associated viruses, pox viruses, including vaccinia virus and attenuated pox viruses, Semliki Forest virus, retroviruses, Sindbis virus and Ty virus-like particles. Particular preference is given to adenoviruses and retroviruses. The retroviruses are typically replication-deficient (i.e. they are incapable of generating infectious particles).

Methods of introducing nucleic acids into cells in vitro or in vivo comprise transfection of nucleic acid calcium phosphate precipitates, transfection of nucleic acids associated with DEAE, transfection or infection with the above viruses carrying the nucleic acids of interest, liposome-mediated transfection, and the like. In particular embodiments, preference is given to directing the nucleic acid to particular cells. In such embodiments, a carrier used for administering a nucleic acid to a cell (e.g. a retrovirus or a liposome) may have a bound target control molecule. For example, a molecule such as an antibody specific for a surface membrane protein on the target cell or a ligand for a receptor on the target cell may be incorporated into or attached to the nucleic acid carrier. Preferred antibodies comprise antibodies which bind selectively a tumor antigen. If administration of a nucleic acid via liposomes is desired, proteins binding to a surface membrane protein associated with endocytosis may be incorporated into the liposome formulation in order to make target control and/or uptake possible. Such proteins comprise capsid proteins or fragments thereof which are specific for a particular cell type, antibodies to proteins which are internalized, proteins addressing an intracellular site, and the like.

The therapeutically active compounds of the invention may be administered via any conventional route, including by injection or infusion. The administration may be carried out, for example, orally, intravenously, intraperitonealy, intramuscularly, subcutaneously or transdermally. Administration can be locally or systemically, preferably systemically.

The term "systemic administration" refers to the administration of an agent such that the agent becomes widely distributed in the body of an individual in significant amounts and develops a desired effect. For example, the agent may develop its desired effect in the blood and/or reaches its desired site of action via the vascular system. Typical systemic routes of administration include administration by introducing the agent directly into the vascular system or oral, pulmonary, or intramuscular administration wherein the agent is adsorbed, enters the vascular system, and is carried to one or more desired site(s) of action via the blood.

According to the present invention, it is preferred that the systemic administration is by parenteral administration. The term "parenteral administration" refers to administration of an agent such that the agent does not pass the intestine. The term "parenteral administration" includes intravenous administration, subcutaneous administration, intradermal administration or intraarterial administration but is not limited thereto.

The pharmaceutical compositions of the invention are preferably sterile and contain an effective amount of the agents described herein and optionally of further agents as discussed herein to generate the desired reaction or the desired effect.

Pharmaceutical compositions are usually provided in a uniform dosage form and may be prepared in a manner known per se. A pharmaceutical composition may e.g. be in the form of a solution or suspension.

A pharmaceutical composition may comprise salts, buffer substances, preservatives, carriers, diluents and/or excipients all of which are preferably pharmaceutically acceptable. The term "pharmaceutically acceptable" refers to the non-toxicity of a material which does not interact with the action of the active component of the pharmaceutical composition.

Salts which are not pharmaceutically acceptable may be used for preparing pharmaceutically acceptable salts and are included in the invention. Pharmaceutically acceptable salts of this kind comprise in a non limiting way those prepared from the following acids: hydrochloric, hydrobromic, sulfuric, nitric, phosphoric, maleic, acetic, salicylic, citric, formic, malonic, succinic acids, and the like. Pharmaceutically acceptable salts may also be prepared as alkali metal salts or alkaline earth metal salts, such as sodium salts, potassium salts or calcium salts.

Suitable buffer substances for use in a pharmaceutical composition include acetic acid in a salt, citric acid in a salt, boric acid in a salt and phosphoric acid in a salt.

Suitable preservatives for use in a pharmaceutical composition include benzalkonium chloride, chlorobutanol, paraben and thimerosal.

The term "carrier" refers to an organic or inorganic component, of a natural or synthetic nature, in which the active component is combined in order to facilitate, enhance or enable application. According to the invention, the term "carrier" also includes one or more compatible solid or liquid fillers, diluents or encapsulating substances, which are suitable for administration to a patient.

Possible carrier substances for parenteral administration are e.g. sterile water, Ringer, Ringer lactate, sterile sodium chloride solution, polyalkylene glycols, hydrogenated naphthalenes and, in particular, biocompatible lactide polymers, lactide/glycolide copolymers or polyoxyethylene/polyoxypropylene copolymers.

An injectable formulation may comprise a pharmaceutically acceptable excipient such as Ringer Lactate.

The term "excipient" when used herein is intended to indicate all substances which may be present in a pharmaceutical composition and which are not active ingredients such as, e.g., carriers, binders, lubricants, thickeners, surface active agents, preservatives, emulsifiers, buffers, flavouring agents, or colorants.

The agents and compositions described herein are administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition.

An effective amount of an agent or composition described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the agents described herein may depend on various of such parameters. In the case that a reaction in a patient is insufficient with an initial dose, higher doses (or effectively higher doses achieved by a different, more localized route of administration) may be used.

The agents and compositions described herein can be administered to patients, e.g., in vivo, to treat or prevent a variety of disorders such as those described herein. Preferred patients include human patients having disorders that can be corrected or ameliorated by administering the agents and compositions described herein. This includes disorders involving cells characterized by an altered expression pattern of Seprase.

For example, in one embodiment, agents described herein can be used to treat a patient with a cancer disease, e.g., a cancer disease such as described herein characterized by the presence of cells expressing Seprase.

The present invention is described in detail by the figures and examples below, which are used only for illustration purposes and are not meant to be limiting. Owing to the description and the examples, further embodiments which are likewise included in the invention are accessible to the skilled worker.

FIGURES

FIG. 1: Amino acid Sequence of MC-FA-010. Disulfide bridges are depicted as grey lines. Cystines are highlighted in yellow and numbered from N- to C-terminus (roman numerals).

Figure 2:
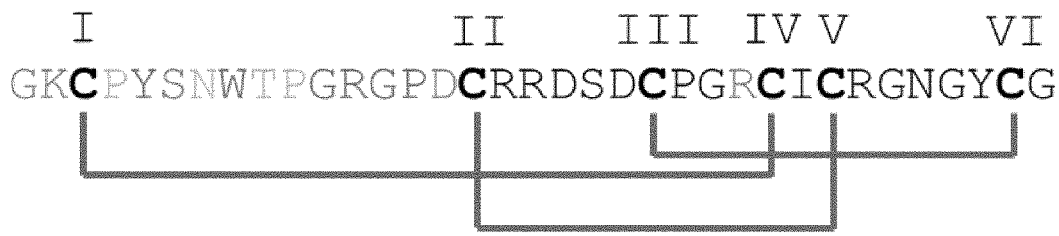

FIG. 2: A: Summary of binding data from alanine scan of MC-FA-010. First column shows position specific parental sequence. Second to fourth column show apparent Kd calculated via one site saturation binding model and calculated Error and $R^2$ value of fitting. Preserved/increased binding (respectively weak loss of binding) is shown in green colors, weak and moderate binding in orange and no binding (complete loss of binding) in red. B: Wildtype sequence of MC-FA-010 with position specific binding highlighted with green, orange and red as described above.

Figure 3:
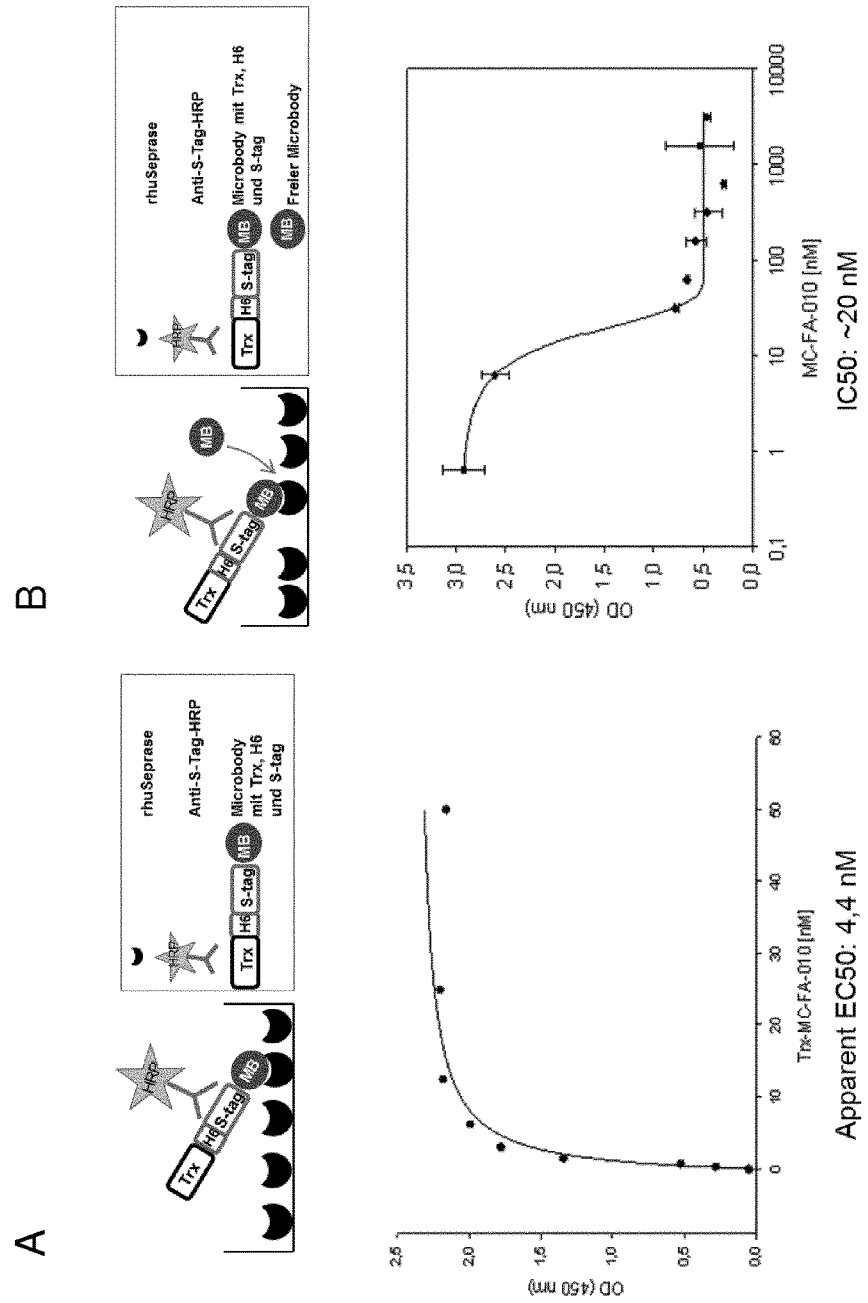

FIG. 3: Binding analysis of Trx-MC-FA-010 to human Seprase. A: ELISA analysis of Trx-MC-FA-010 binding to human Seprase in a range of 0.39 to 50 nM. B: Competition ELISA analysis. Binding of 3 nM Trx-MC-FA-010 to human Seprase was competed with soluble monovalent MC-FA-010 in a range of 0.64-3167 nM.

Figure 4:
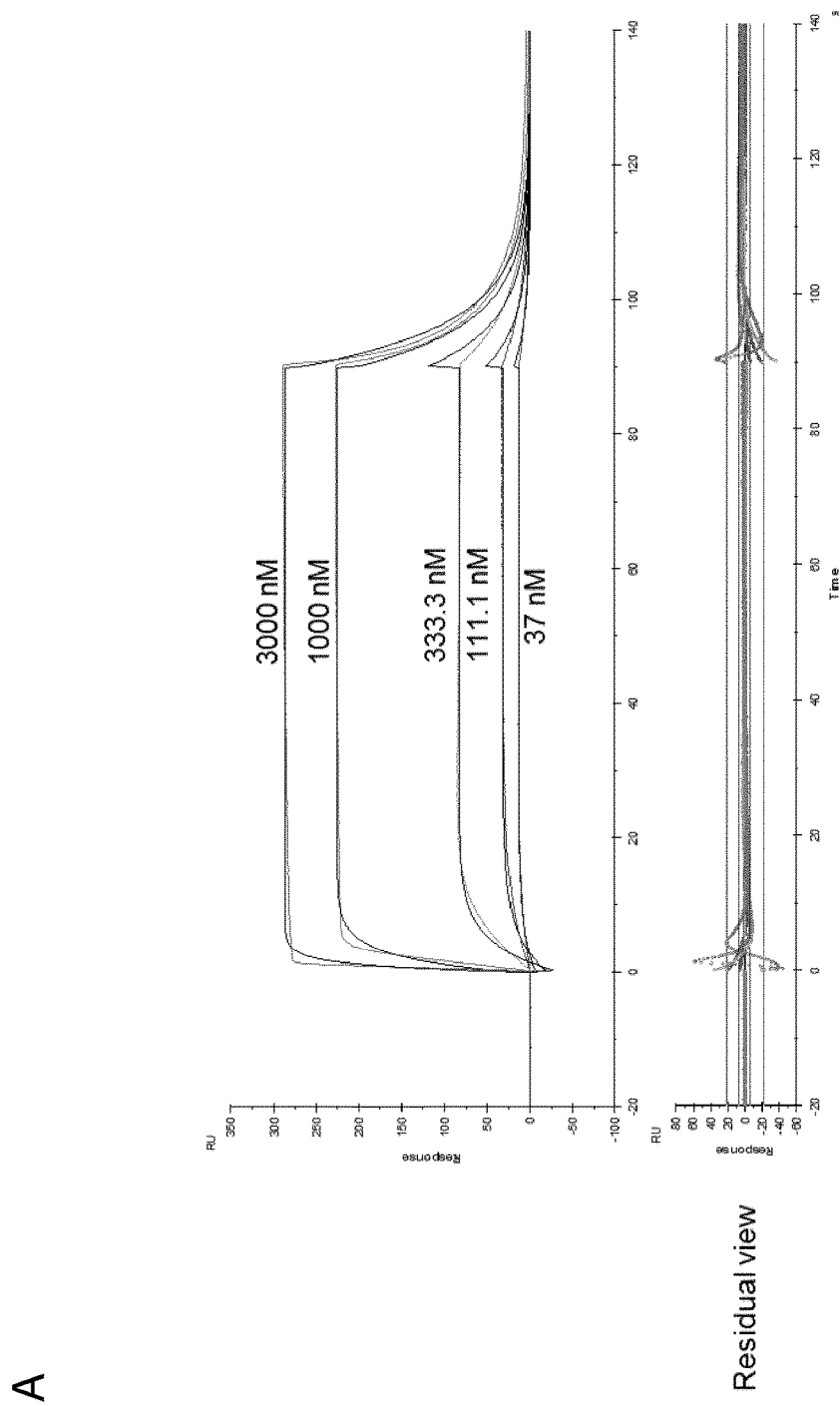

FIG. 4: SPR analysis of MC-FA-010 binding to immobilized human Seprase. A: Upper plot: Fitted data of association and dissociation step. Overlay of all concentrations analyzed. Lower plot: Residual view of measured and fitted curves. B: Summary of measured and calculated data.

Figure 5:
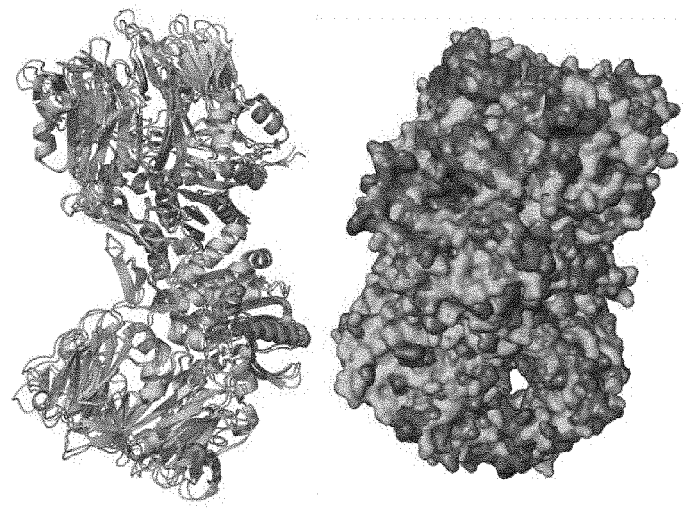
Figure 5:
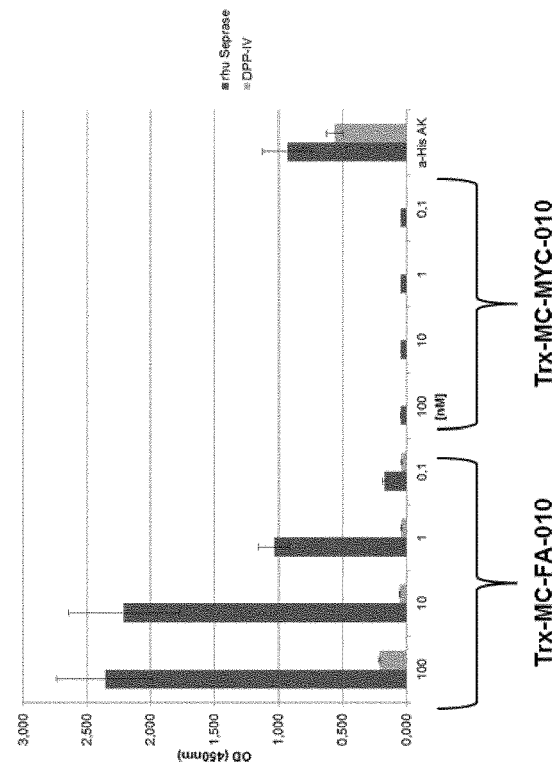

FIG. 5: Analysis of selectivity of MC-FA-010 towards human FAPα. A: Structural overlay of DPP VI depicted in cyan or grey and Seprase depicted in green (Pymol). B: ELISA analysis of Trx-MC-FA-010 binding to human Seprase (rhuSeprase, dark grey bars) and DPP IV (light grey bars). Dataset shown is based on duplicates.

Figure 6:
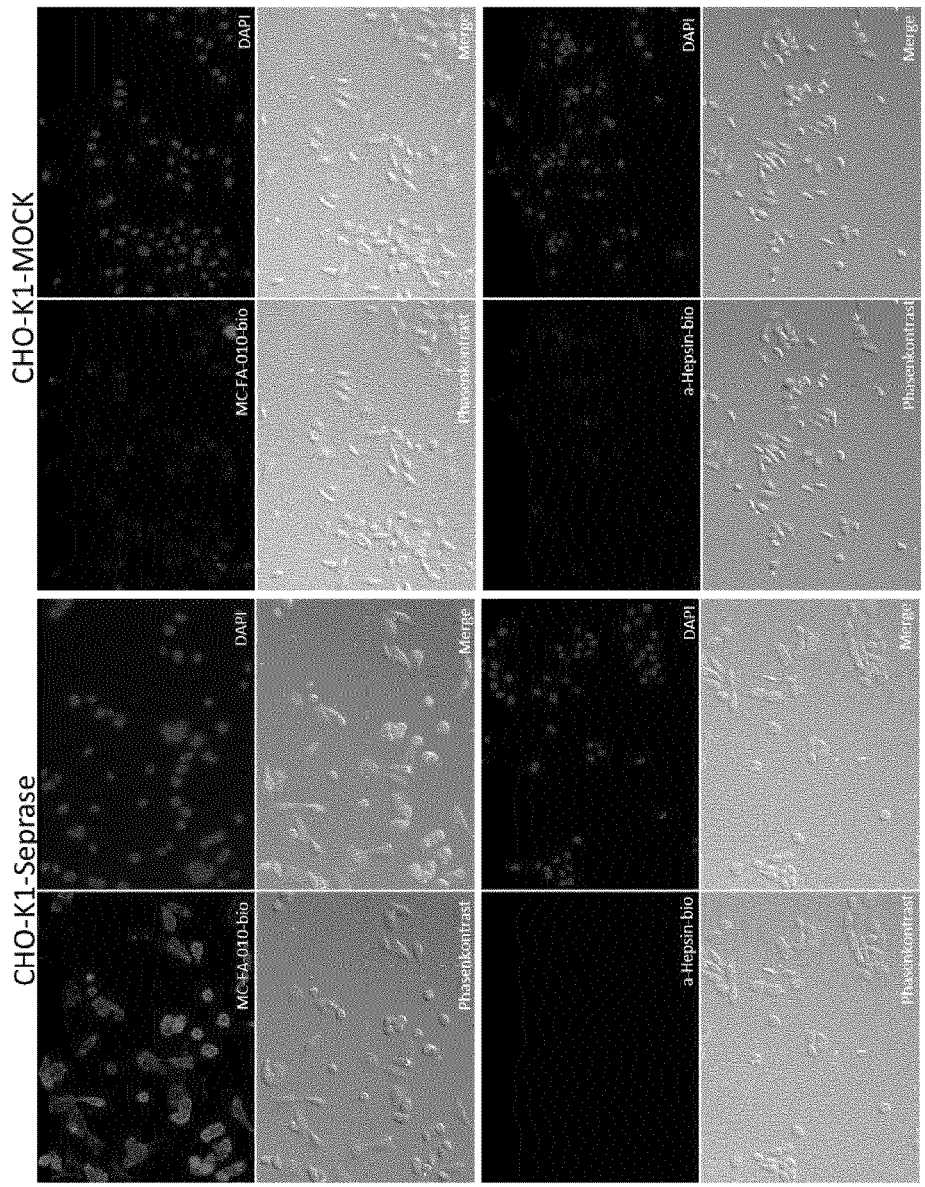

FIG. 6: Immunofluorescence for investigation of MC-FA-010 specificity. Binding of streptavidin-Cy3-conjugated MC-FA-010 to Seprase-overexpressing CHO-K1 cells (CHO-K1-Seprase) was analyzed. Before incubation with cells MC-FA-010 and the control Microbody® were biotinylated and preassembled on Cy3-conjugated streptavidin. As negative controls an unrelated Microbody™ (a-Hepsin-bio) and target negative CHO-K1-MOCK cells were used. Microbody™-Streptavidin-Cy3 complex (red) and nuclei localization (blue).

Figure 7:
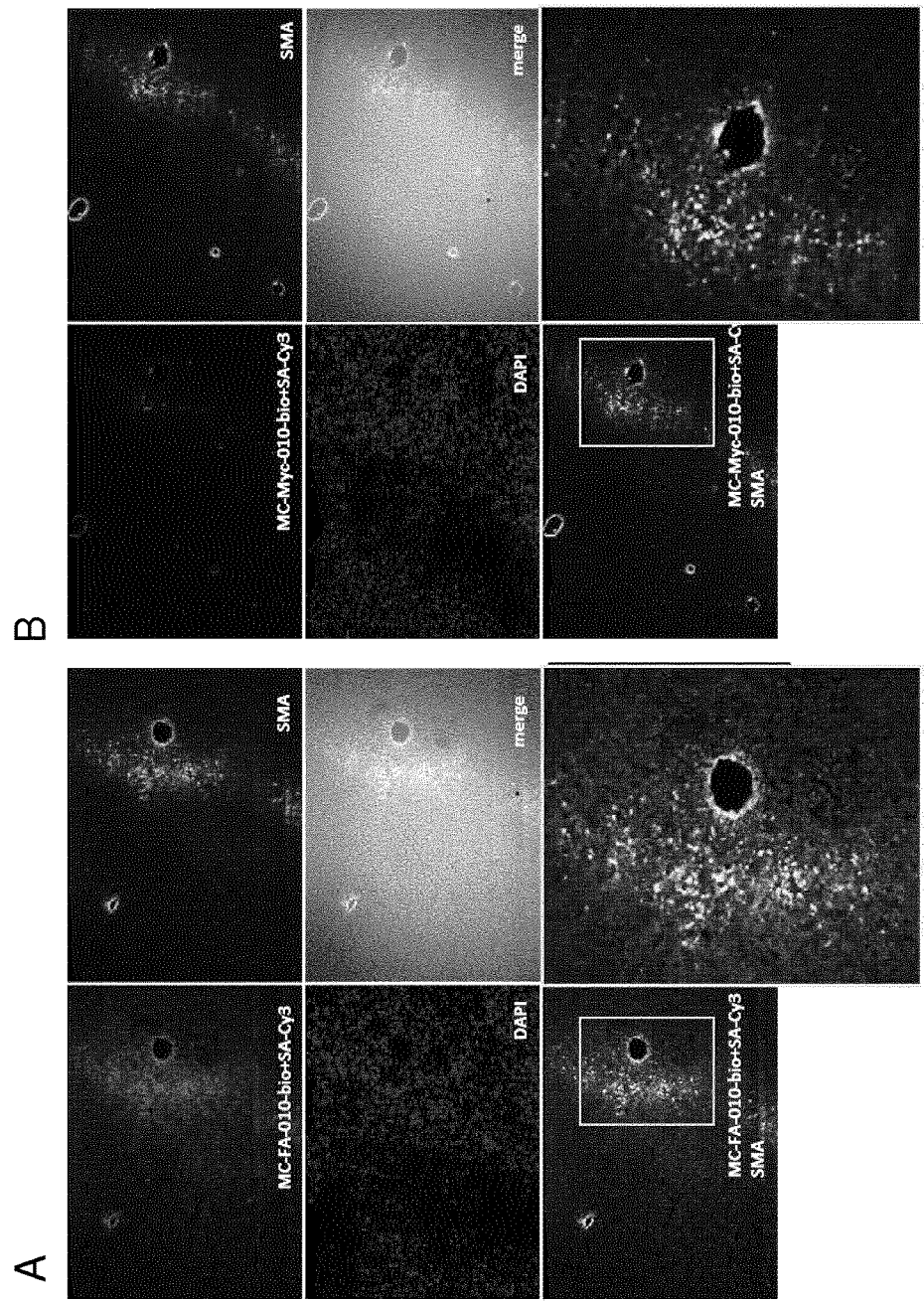

FIG. 7: Staining of paraffin-embedded CT26 cell lines after ex vivo conditioning. After 14 days of implantation all sections were stained with the CAF marker anti-α-SMA (green) and DAPI for nuclei localization (blue). In (A) sections were additional treated with MC-FA-010 which was biotinylated and preassembled on Cy3-conjugated streptavidin. In (B) the sections were stained with the control Microbody™ MC-Myc-010, which was also tetramerized with Streptavisin-Cy3.

Figure 8:
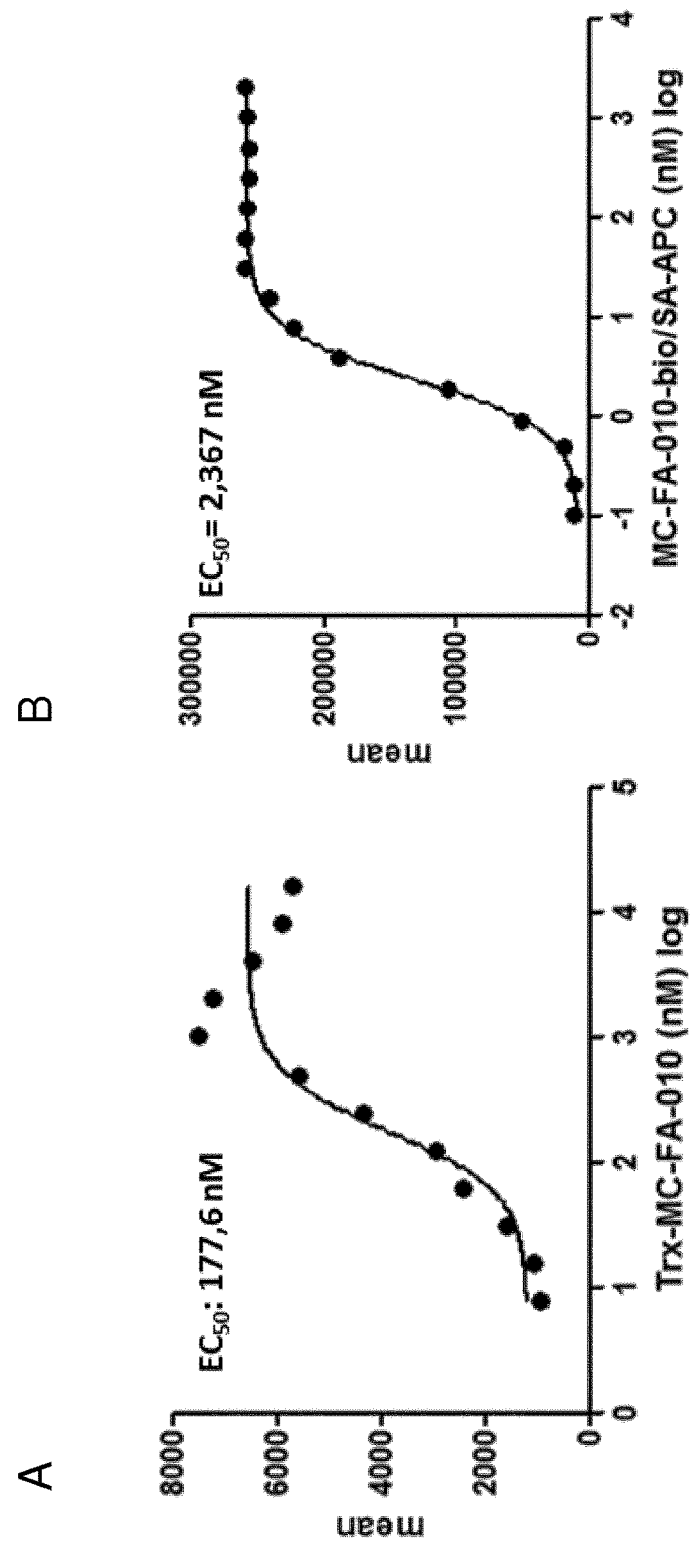

FIG. 8: Binding properties of monovalent and tetravalent MC-FA-010. (A) FACS for determination of the $EC_{50}$ value of monovalent MC-FA-010 (consists of a Thioredoxin-His6-cassette) on human Seprase expressing cells (CHO-K1-Seprase). MC-FA-010 was detected with a His specific PE-conjugated antibody. (B) FACS for determination of the $EC_{50}$ value of streptavidin-APC coupled tetravalent MC-FA-010 on human Seprase expressing cells (CHO-K1-Seprase). Measurements were done in three independent experiments.

Figure 9:
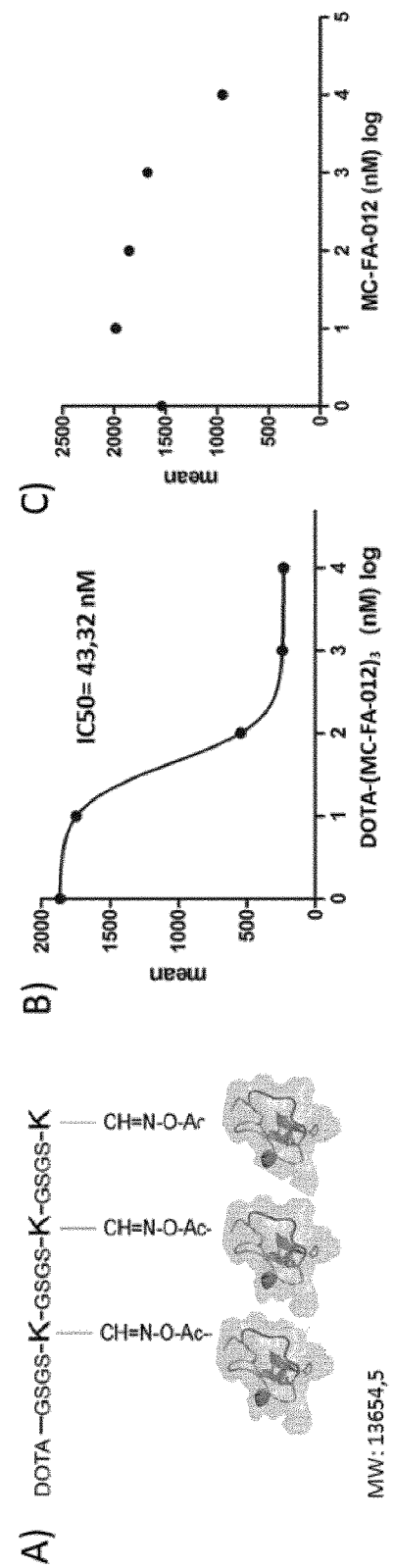

FIG. 9: A) Schematic representation of the DOTA-(MC-FA-012)₃ trimer. The molecular weight of the molecule is indicated below. The trimer was functionally analyzed using a FACS-based competition assay (B) in comparison to the monomeric MC-FA-012 Microbody® (C).

Figure 10:
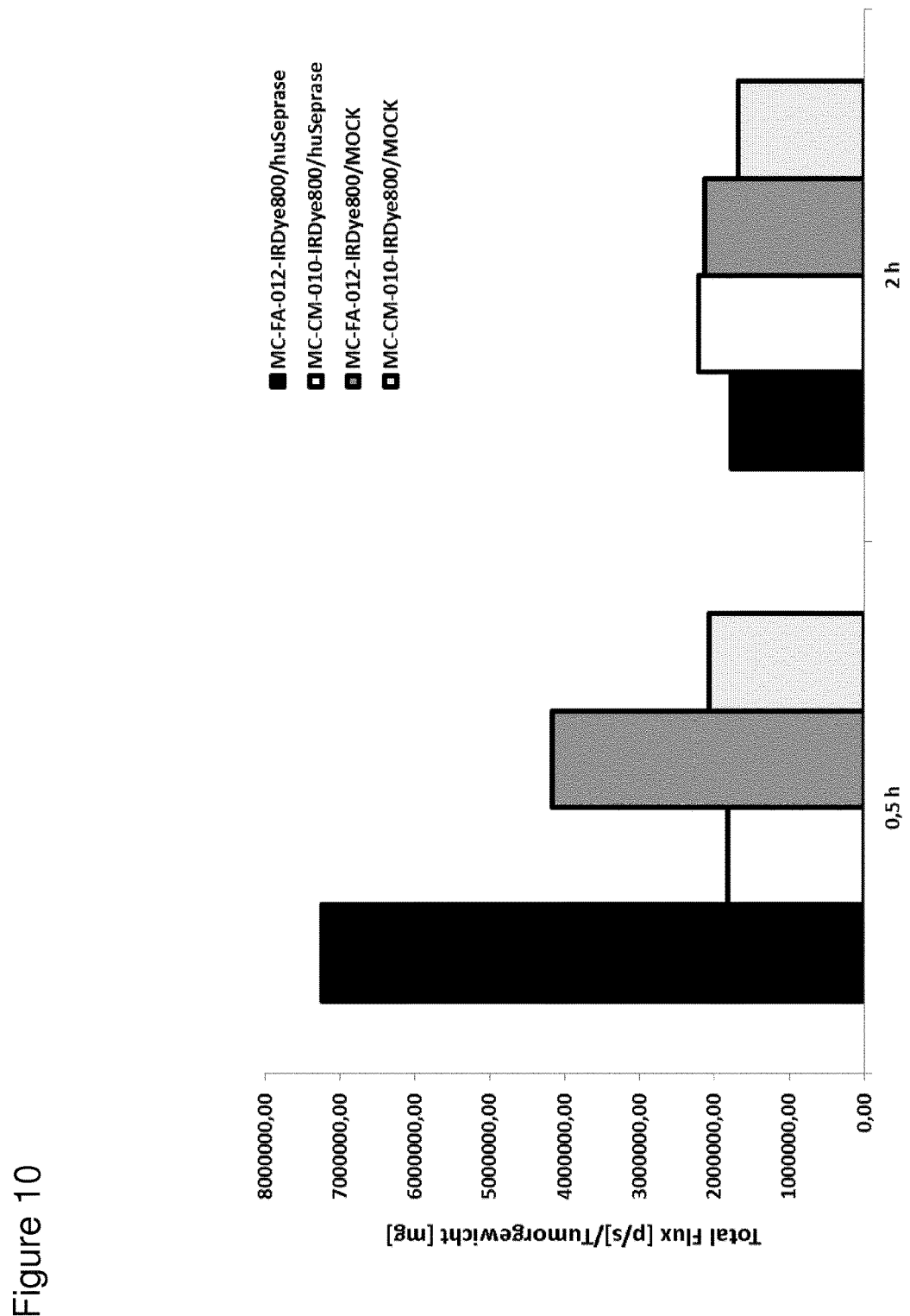

FIG. 10: Tumor targeting in Seprase expressing CHO-Xenograft with IRDye conjugated MC-FA-012. Human Seprase-positive cells (CHO-K1-huSeprase) were inoculated subcutaneously into the flanks of Foxn1(nu) mice. As a negative control huSeprase-negative cells (CHO-K1-MOCK) were used in parallel. After 3 weeks the mice were randomly assigned to the negative control (MC-CM-010-IRDye800CW) or MC-FA-010-IRDye800CW treatment. 5 nmol of each Microbody™ was intravenously administered. 0.5 h and 2 h after injection mice were euthanized and tumor were isolated. The IR signal was measured ex vivo on a Xenogen IVIS optical in vivo imaging system.

Figure 11:
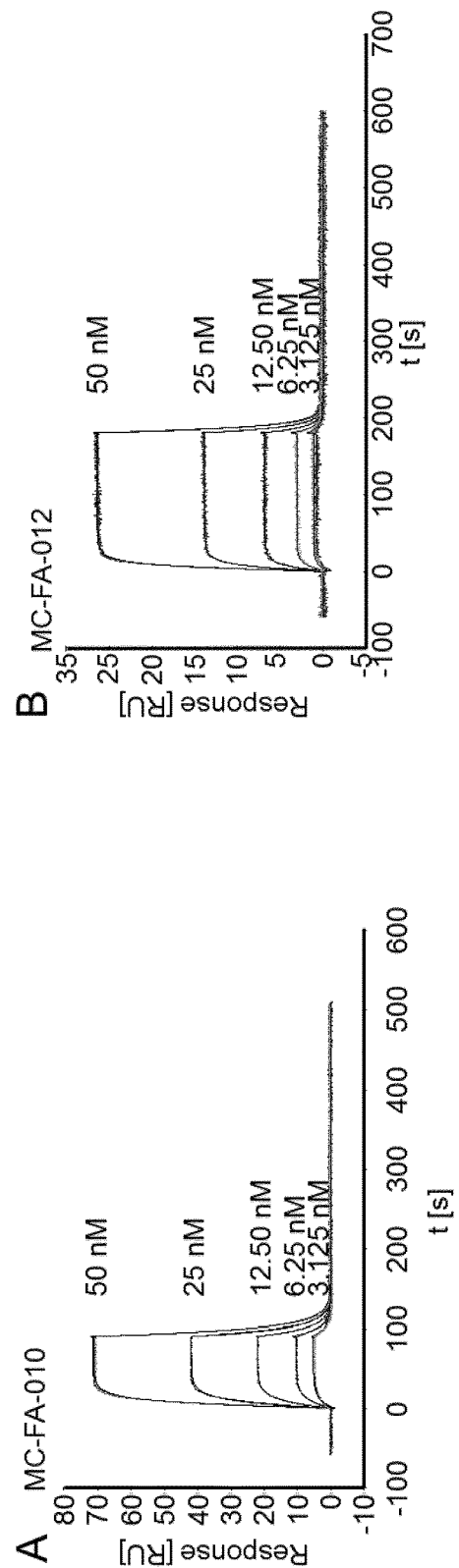
Figure 11:
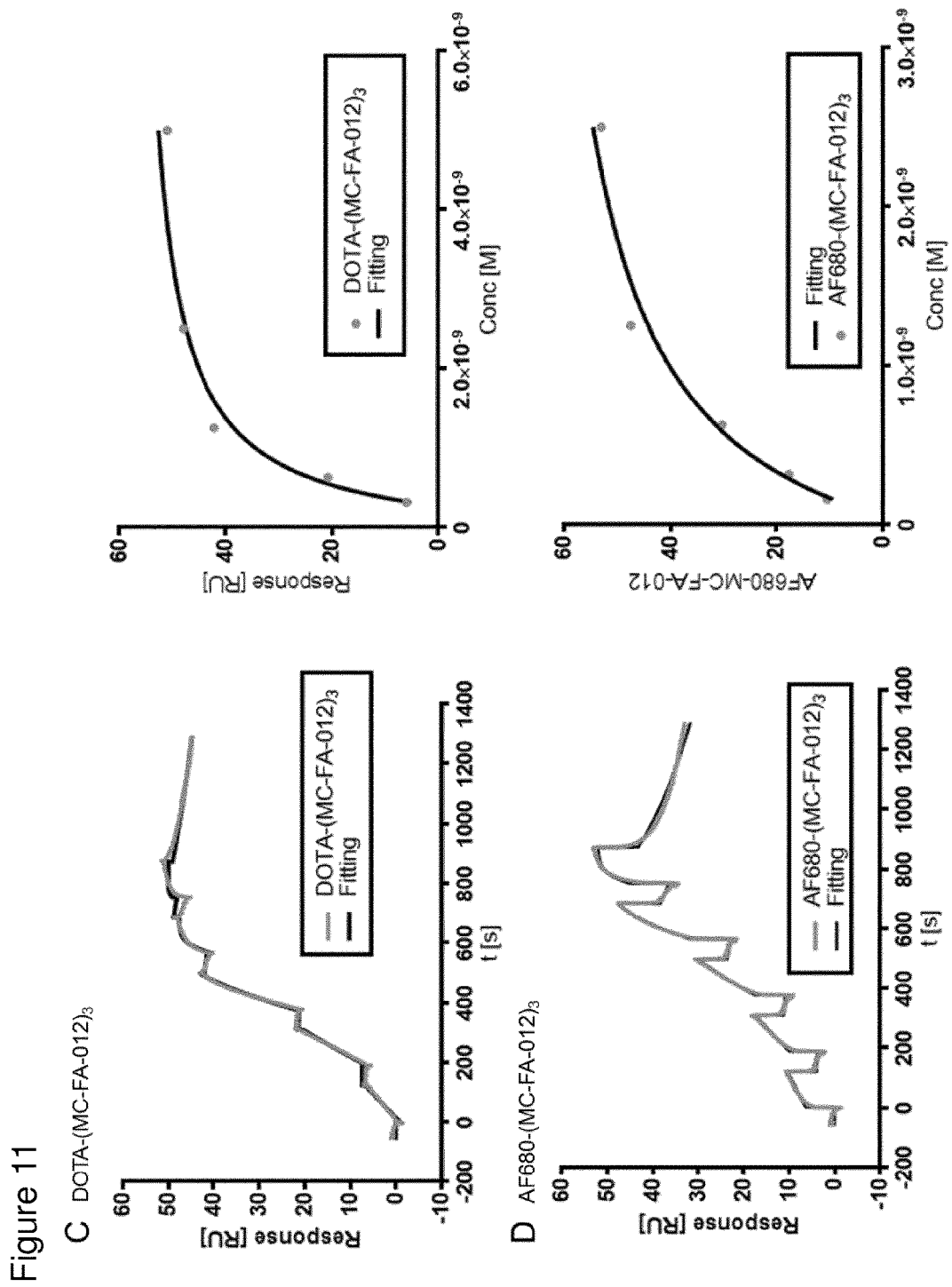

FIG. 11: Surface plasmon resonance spectroscopy of Microbodies and trimers thereof binding rhuSeprase: A: Association and dissociation spectrogram of MC-FA-010, 1:1 fitting; B: Association and dissociation spectrogram of MC-FA-012, 1:1 fitting; C: Spectrogram: Single-cycle measurement and 1:1 fitting of DOTA-(MC-FA-012)₃, Diagram: Corresponding steady state analysis and 1:1 fitting; D: Spectrogram: Single-cycle measurement and 1:1 fitting of AF680-(MC-FA-012)₃, Diagram: Corresponding steady state analysis and 1:1 fitting.

Figure 12:
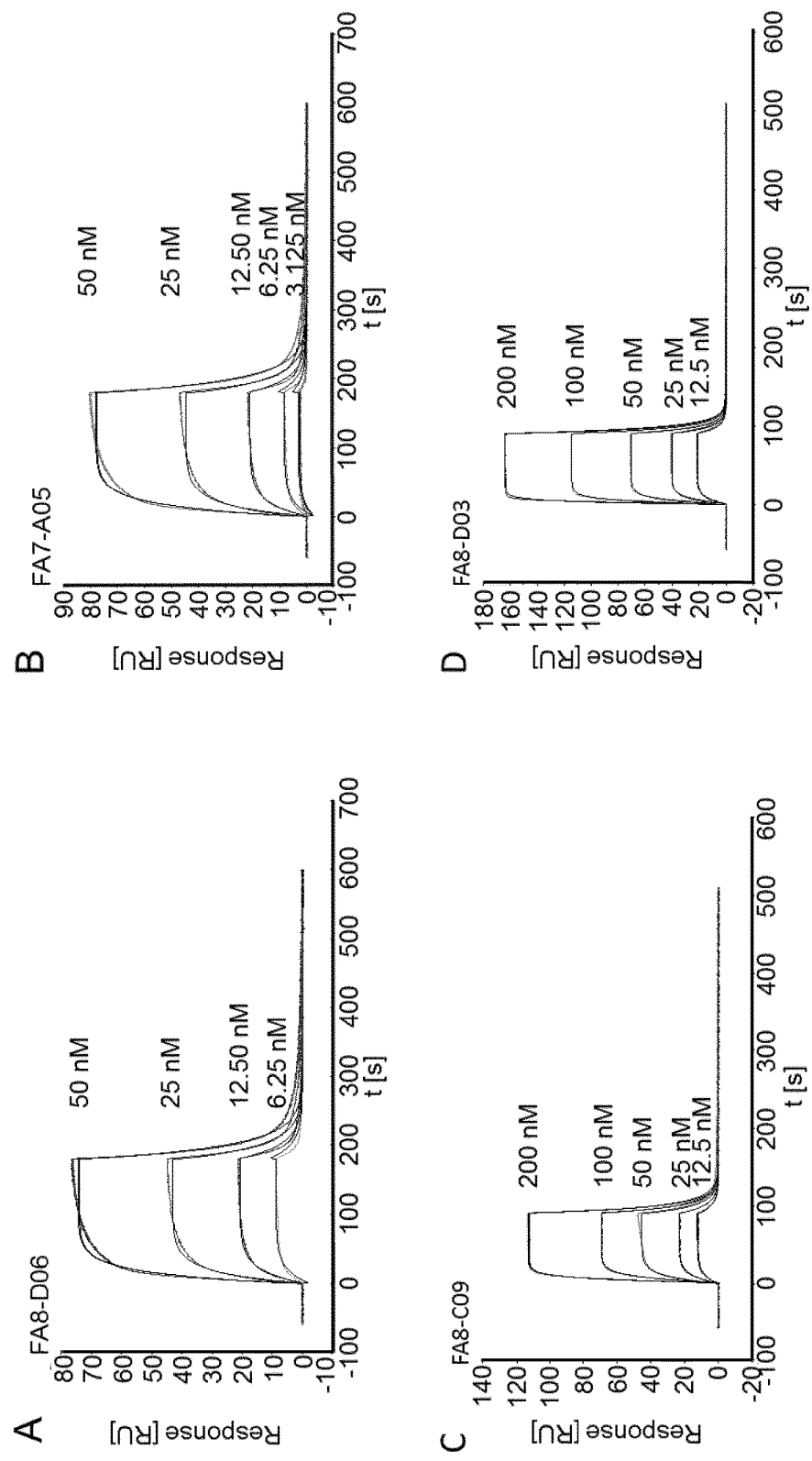
Figure 12:
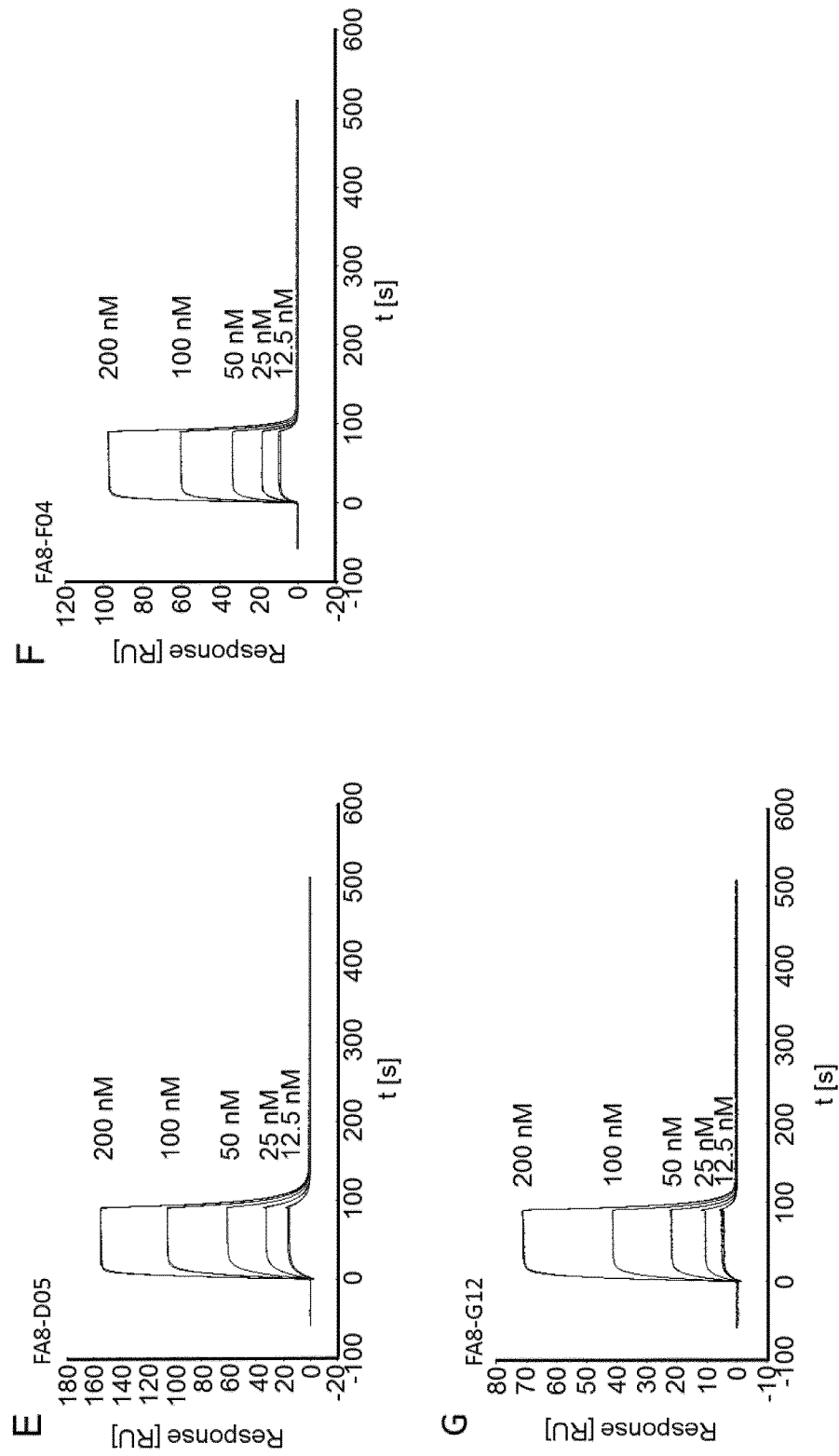

FIG. 12: Surface plasmon resonance spectroscopy of Micobody® MC-FA-012 variants binding rhuSeprase: A: Association and dissociation spectrogram of FA8-D06, 1:1 fitting. B: Association and dissociation spectrogram of FA7-A05, 1:1 fitting; C: Association and dissociation spectrogram of FA8-009, 1:1 fitting; D: Association and dissociation spectrogram of FA8-D03, 1:1 fitting; E: Association and dissociation spectrogram of FA8-D05, 1:1 fitting; F: Association and dissociation spectrogram of FA8-F04, 1:1 fitting; G: Association and dissociation spectrogram of FA8-G12, 1:1 fitting.

Figure 13:
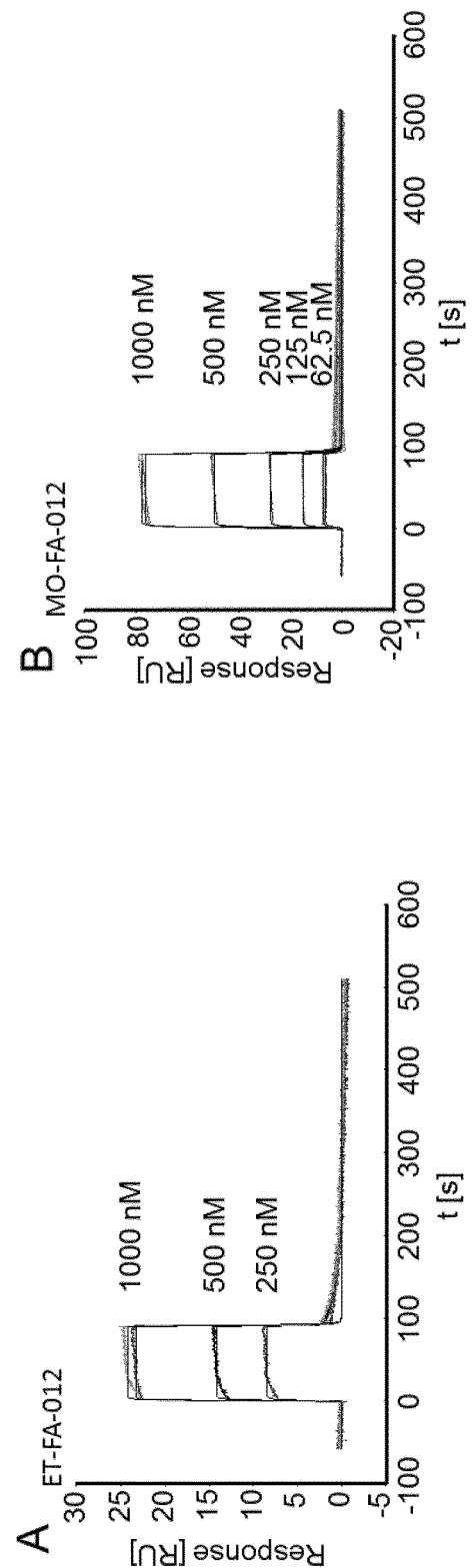

FIG. 13: Surface plasmon resonance spectroscopy of Seprase-binding alternative scaffolds ET-FA-012 and MO-FA-012: A: Association and dissociation spectrogram of ET-FA-012, 1:1 fitting; B: Association and dissociation spectrogram of MO-FA-012.

Figure 14:
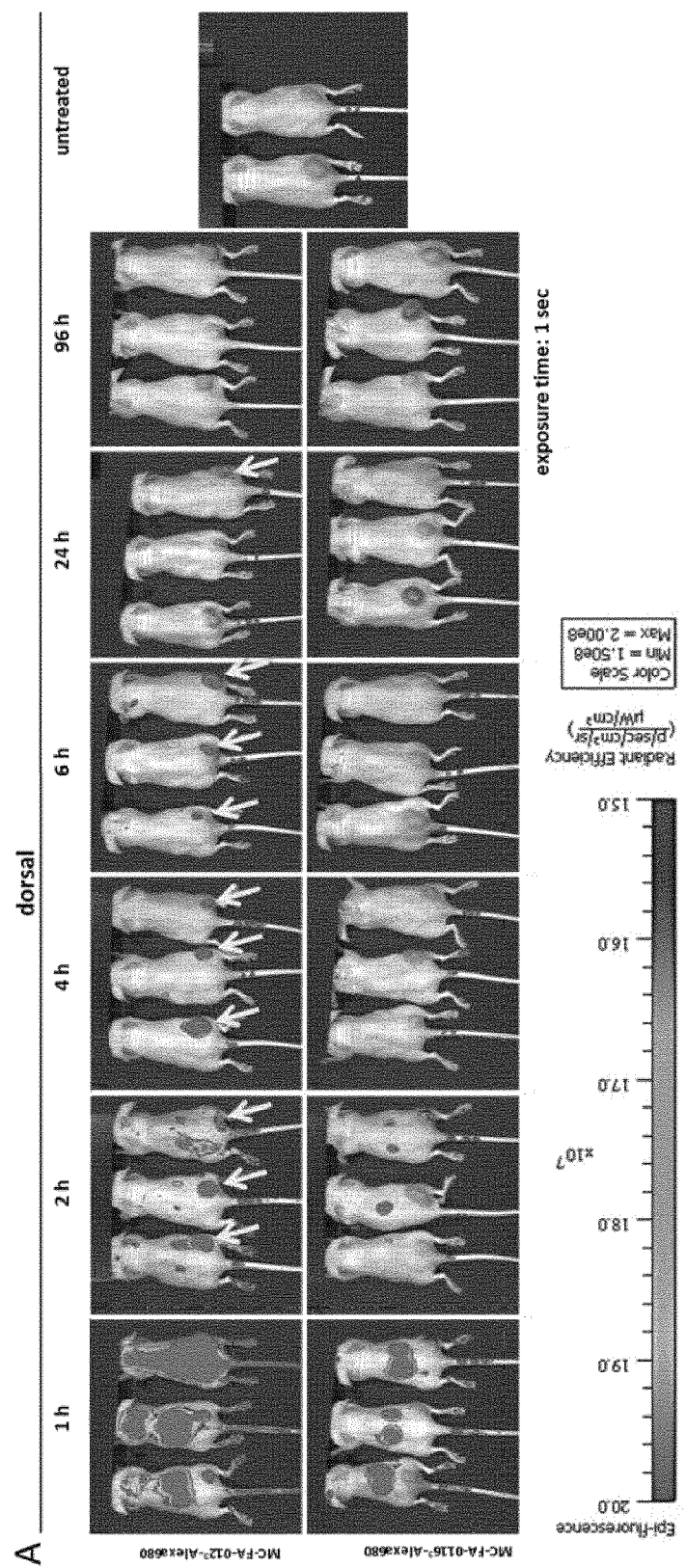
Figure 14:
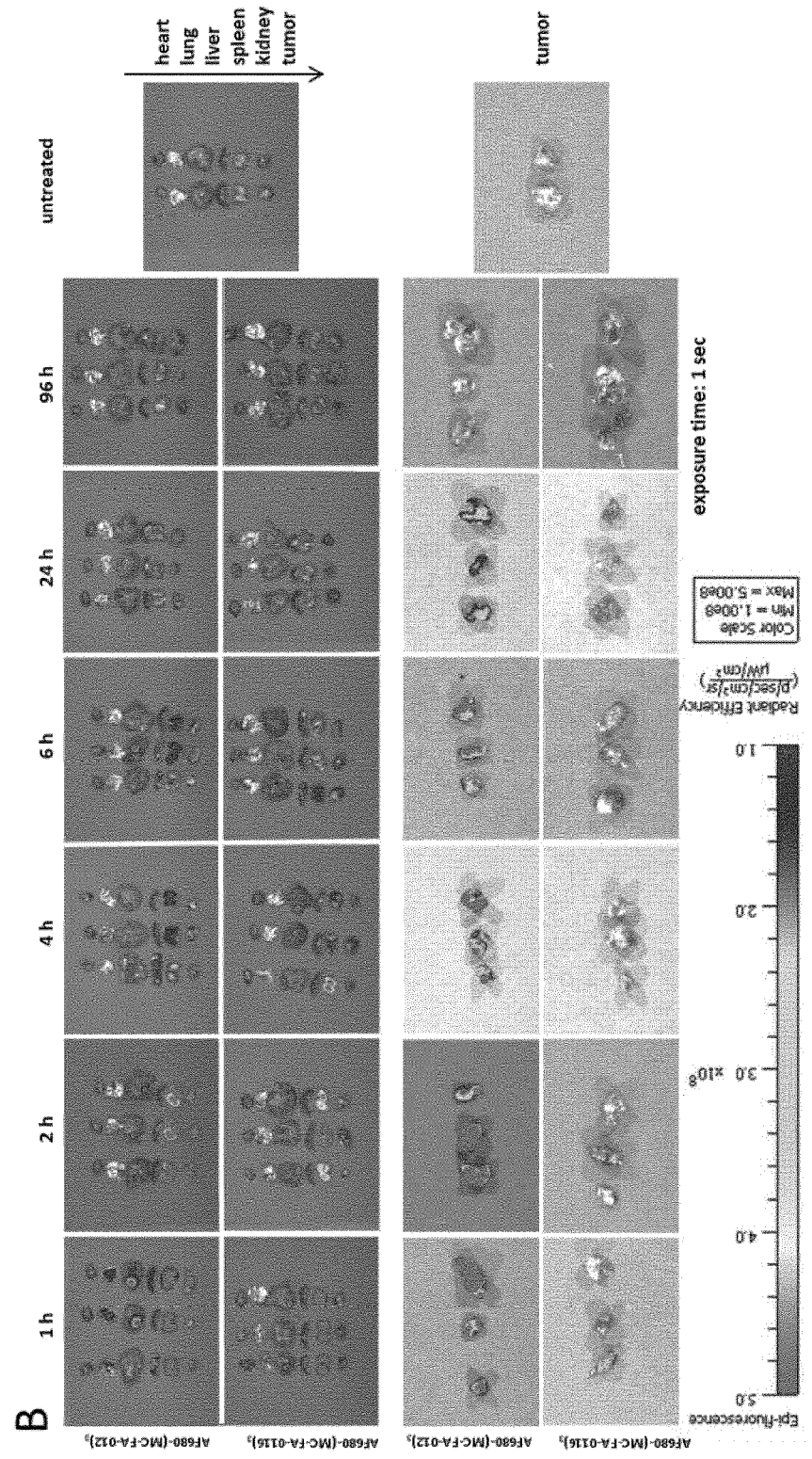

FIG. 14: Biodistribution analysis of AF680-(MC-FA-012)₃ and AF680-(MC-FA-0116)₃, A: In vivo imaging of tumor targeting and organ distribution. B: Ex vivo Imaging of dissected tumors and organs. Arrow: tumor uptake.

Figure 15:
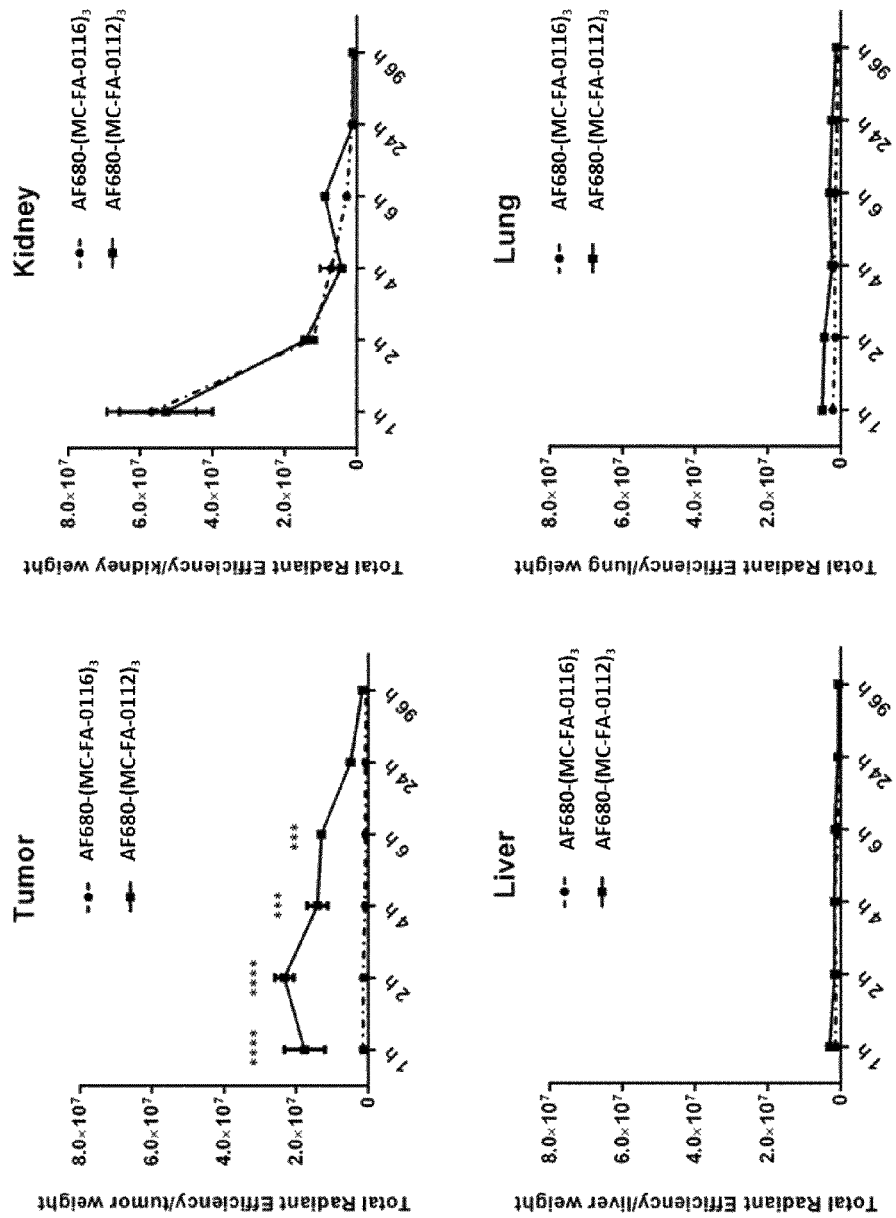

FIG. 15: Comparison of fluorescence signals of AF680 coupled MC-FA-012 and MC-FA-0116 trimer measured ex vivo after 1, 2, 4, 6, 24 and 96 h post-injection. Shown are the total radiant efficiency values per weight in tumor, kidney, liver and lung.

Figure 16:
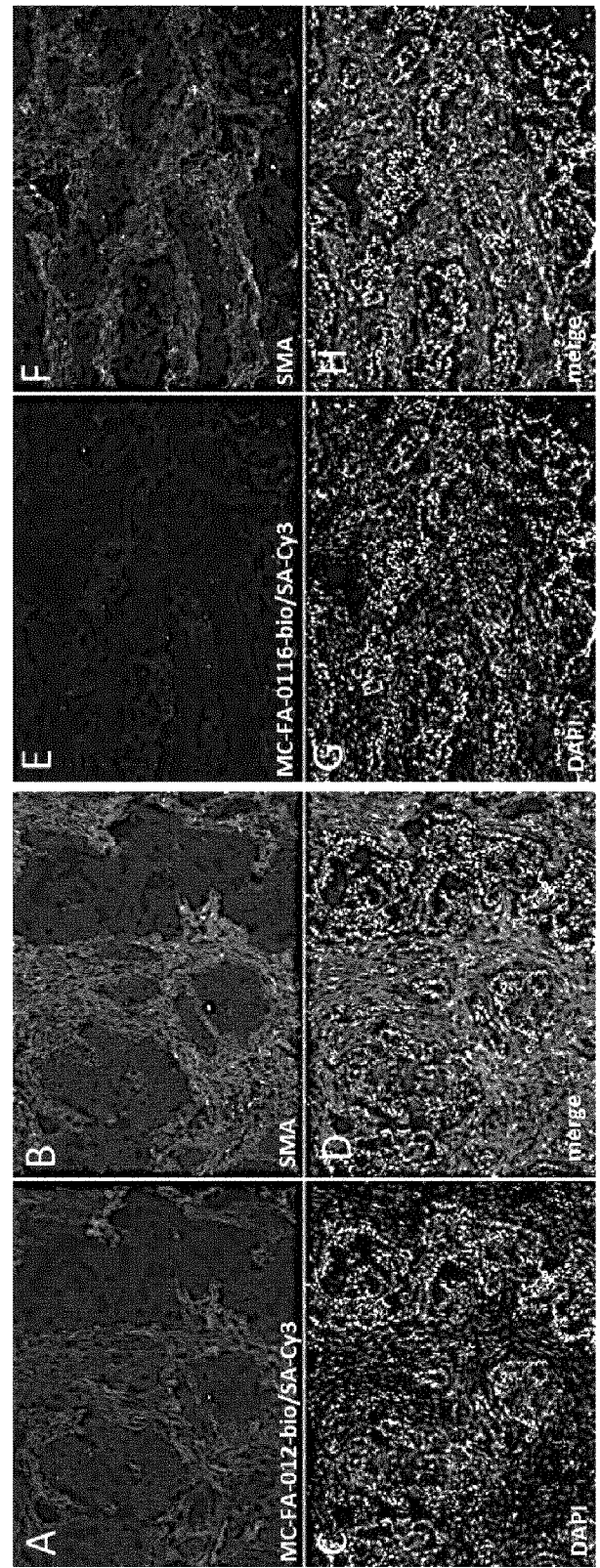

FIG. 16: Immunofluorescence staining of TNBC sections expressing Seprase. Used Microbodies had been tetramerized via Streptavidin-Cy3 conjugate (SA-Cy3). Activated fibroblasts were stained with an anti smooth muscle actin antibody (SMA).

Figure 17:
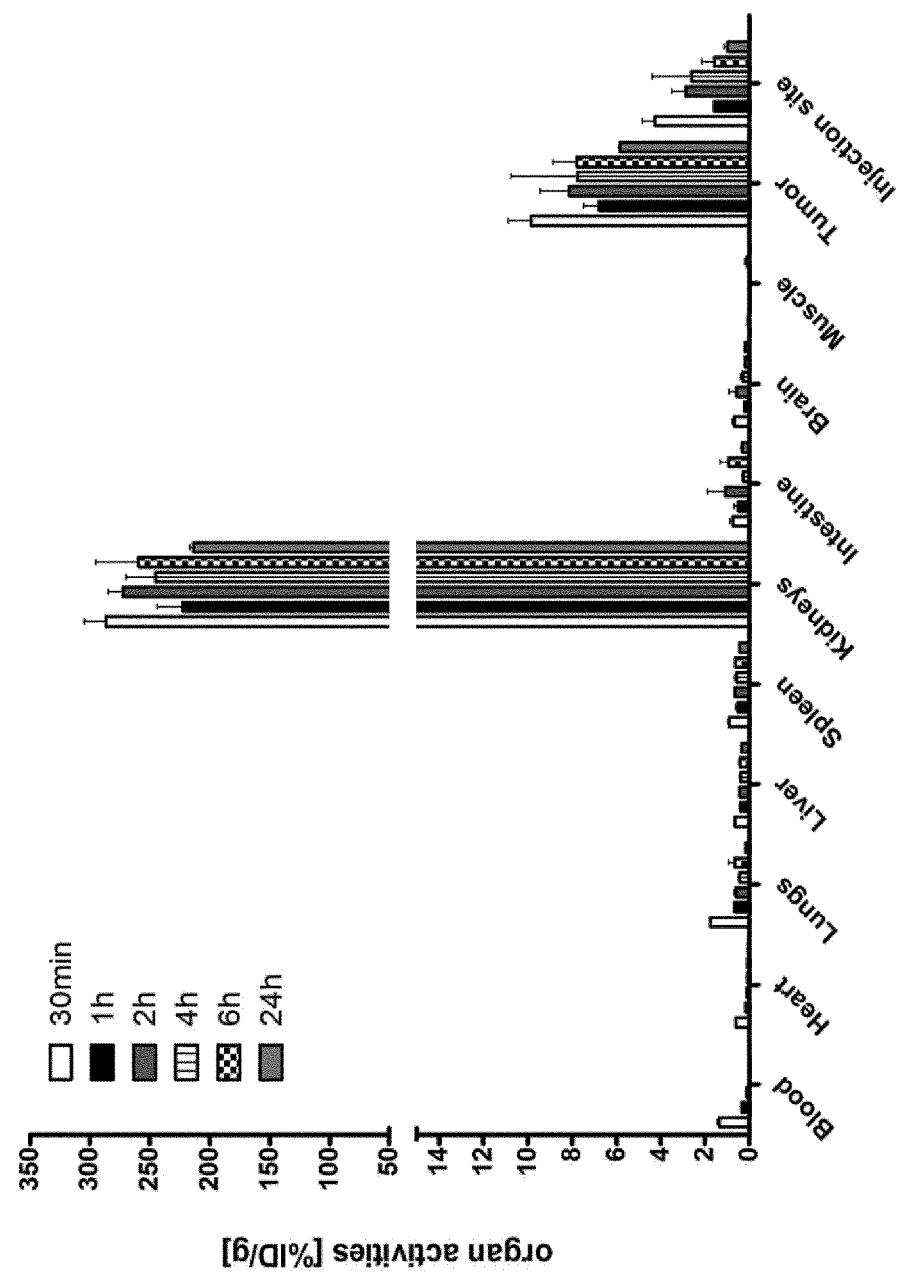

FIG. 17: Organ activities measured 30 min to 24 h after intravenous administration of $^{177}$Lu-(MC-FA-012)₃, calculated as percentage of injected dose per organ weight [% ID/g].

Figure 18:
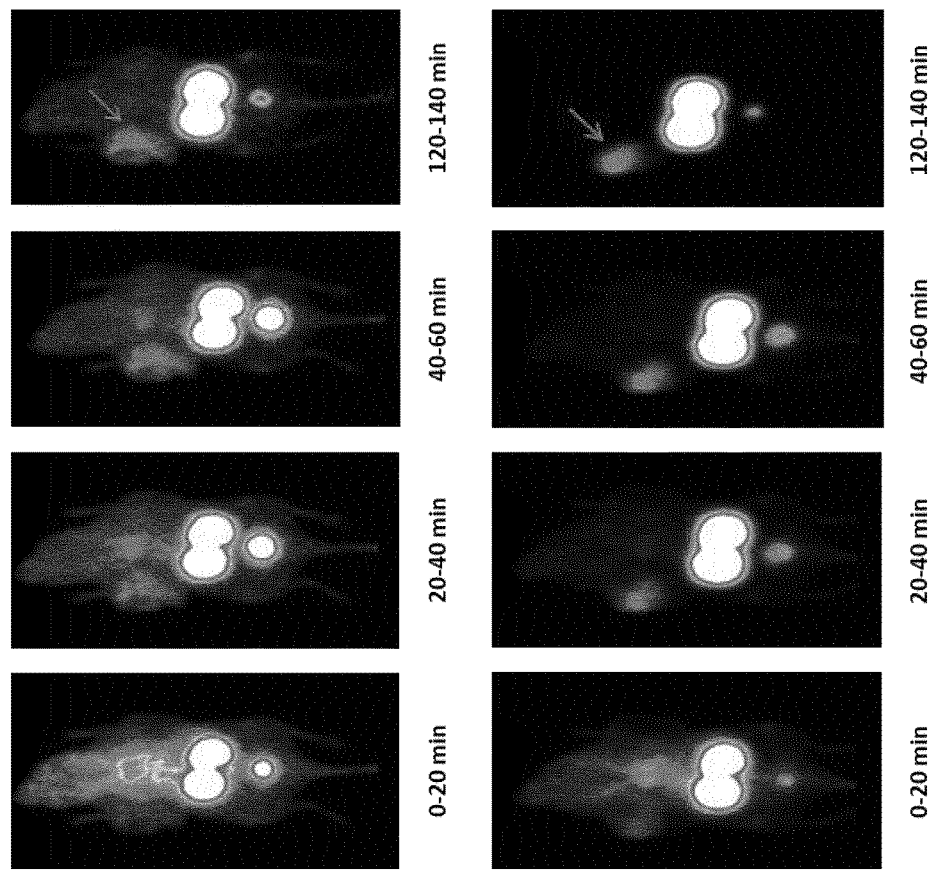

FIG. 18: Maximum intensity projections (MIP) after i.v. administration of ~10 MBq $^{68}$Ga-(MC-FA-012)₃ (upper row: first mouse, bottom row: second mouse). Location of CT26-huSeprase tumor is indicated by the arrows.

Figure 19:
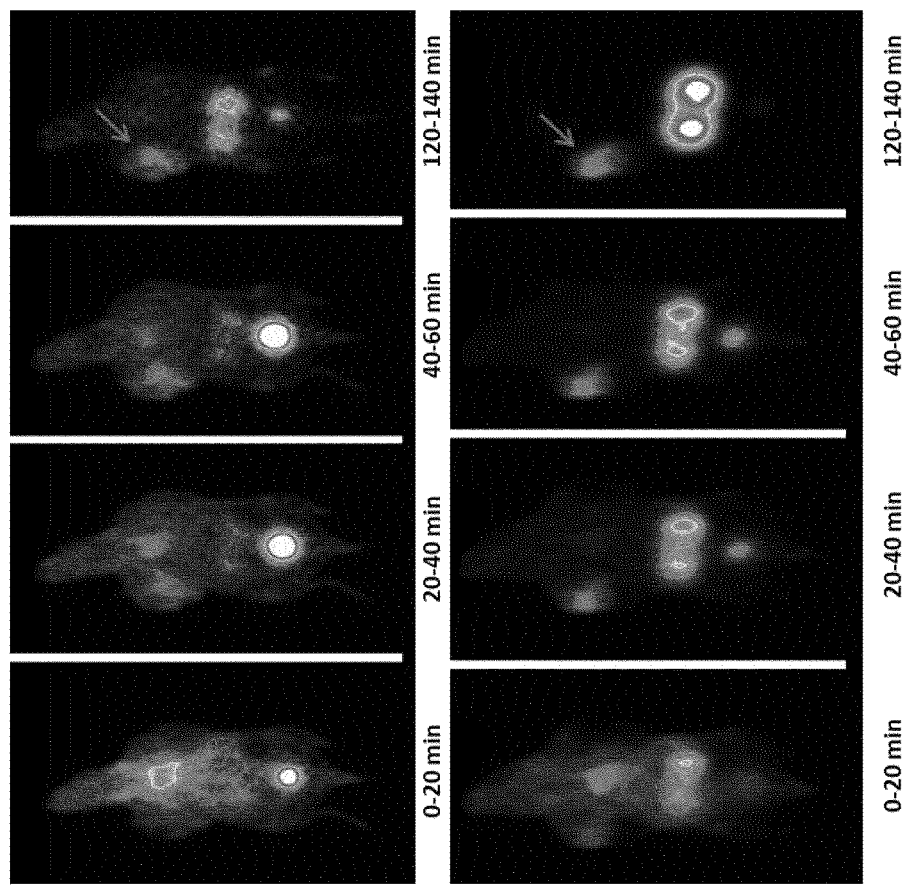

FIG. 19: Standardized uptake values (SUV) after i.v. administration of ~10 MBq $^{68}$Ga-(MC-FA-012)₃ (upper row: first mouse, bottom row: second mouse). Location of CT26-huSeprase tumor is indicated by the arrows.

Figure 20:
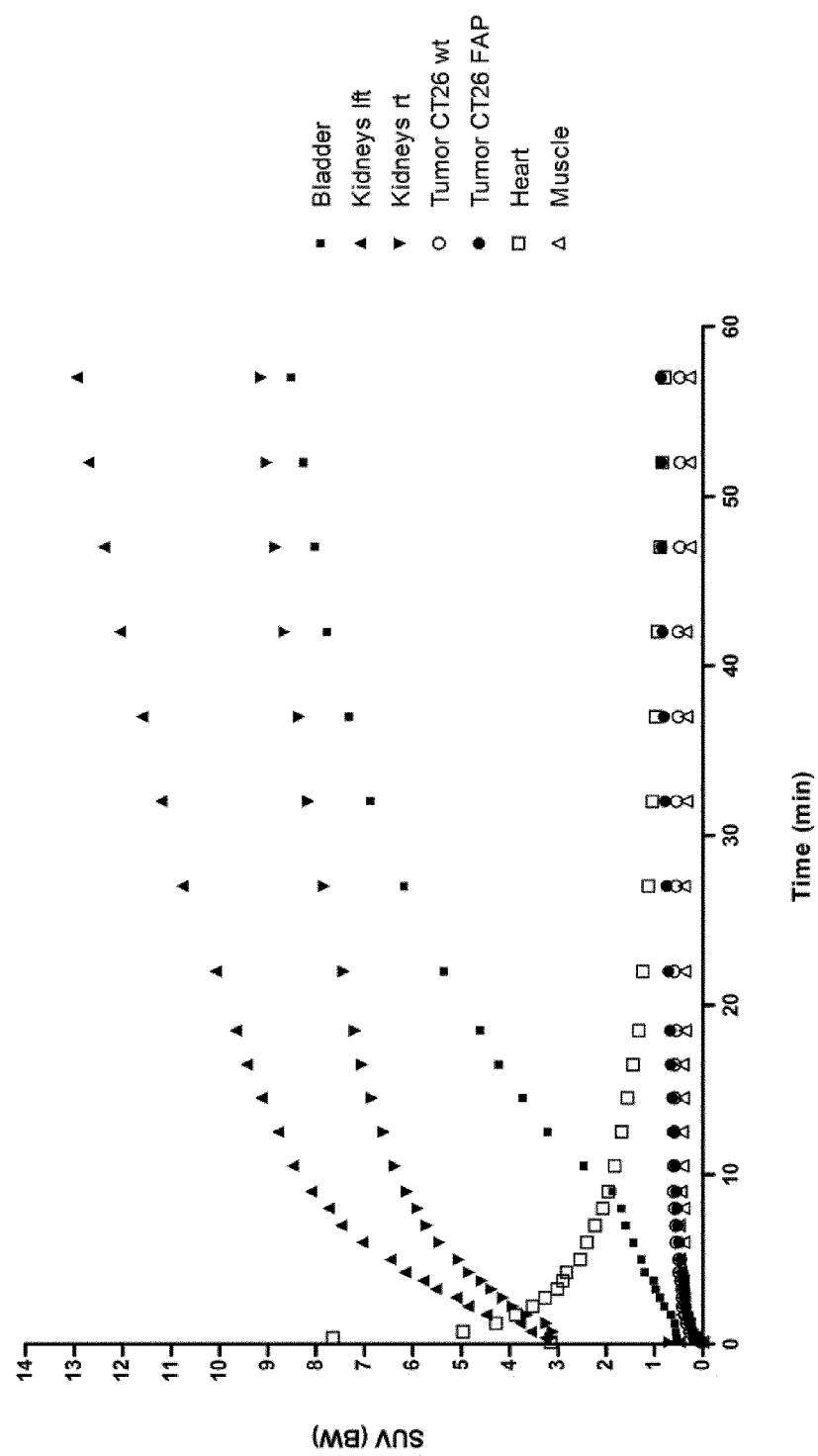

FIG. 20: Small animal PET imaging: Standardized uptake values of selected organs (mouse 1), Kidneys 1 ft: left kidney, Kidneys rt: right kidney; Tumor CT26 wt: CT26 tumor; Tumor CT26-FAP: CT26-huSeprase tumor.

Figure 21:
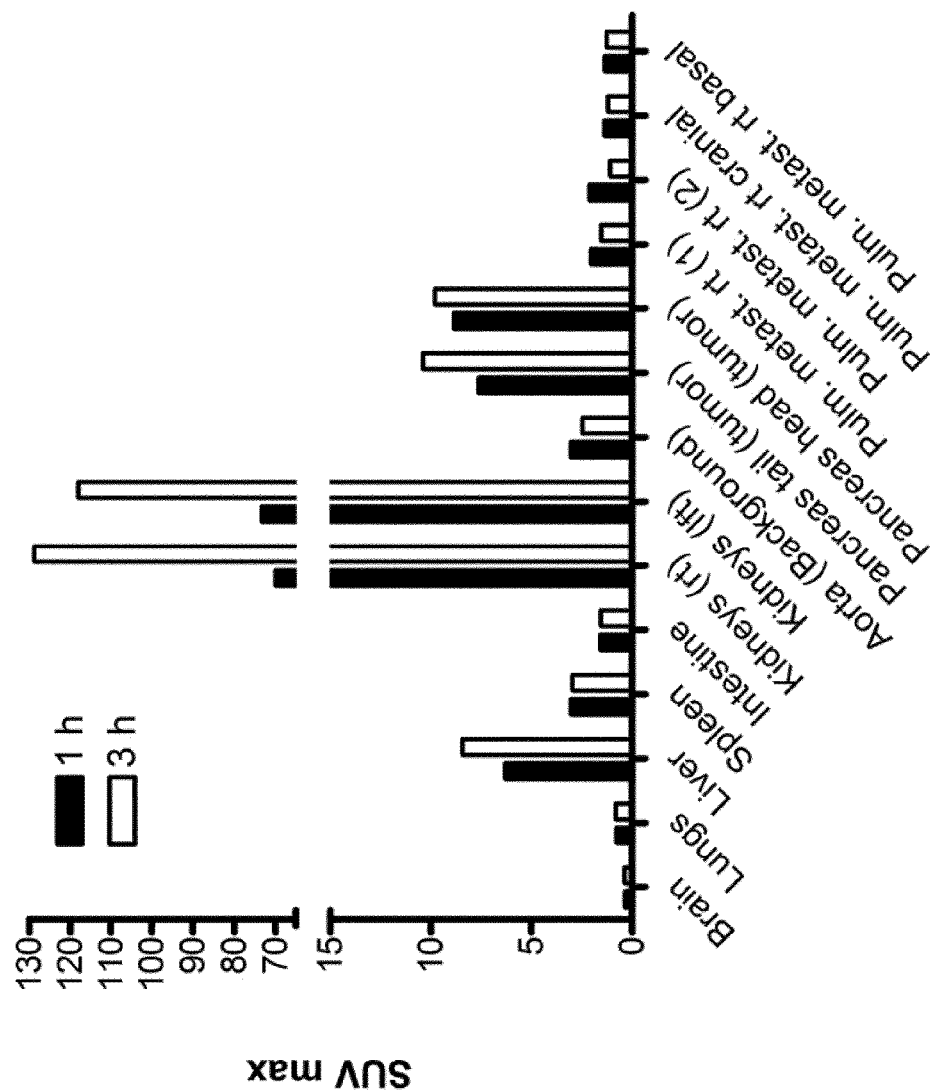

FIG. 21: Organ distribution of $^{68}$Ga-(MC-FA-012)₃ 1 and 3 hours after administration (SUV max) in patient 1 (rt=right, 1 ft=left).

Figure 22:
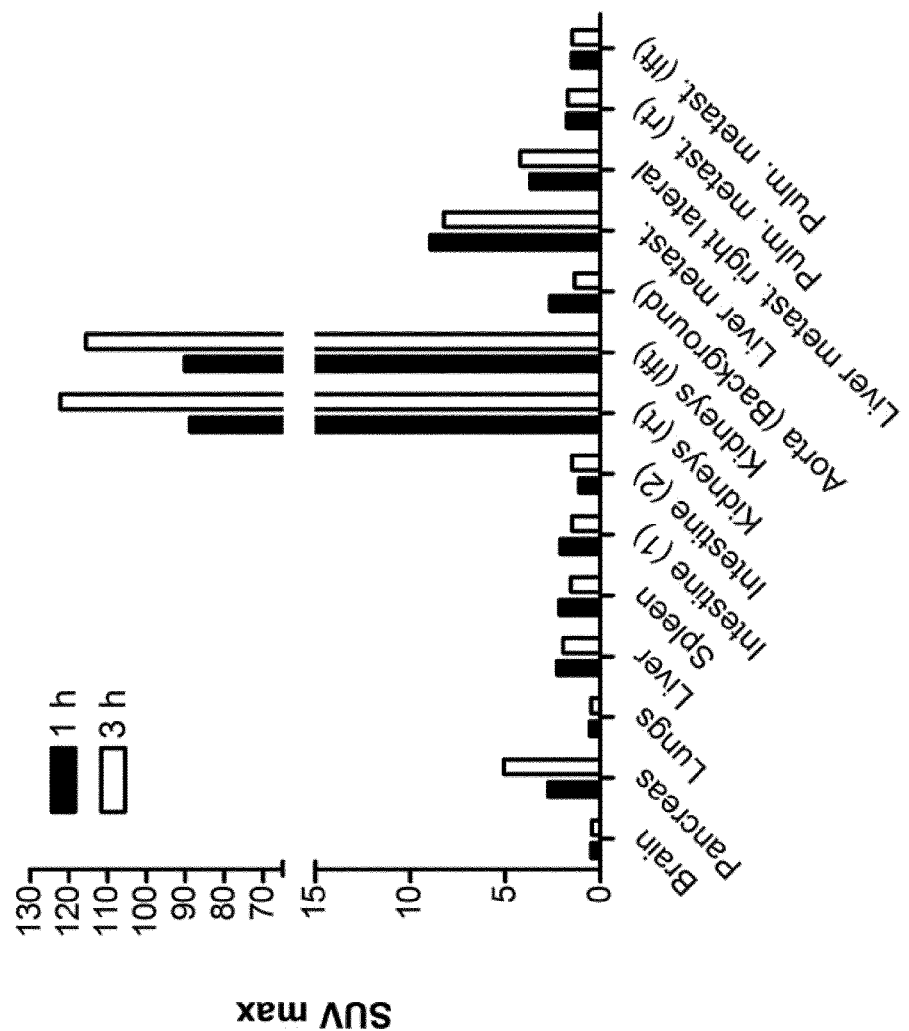

FIG. 22: Organ distribution of $^{68}$Ga-(MC-FA-012)₃ 1 and 3 hours after administration (SUV max) in patient 2 (rt=right, 1 ft=left).

Figure 23:
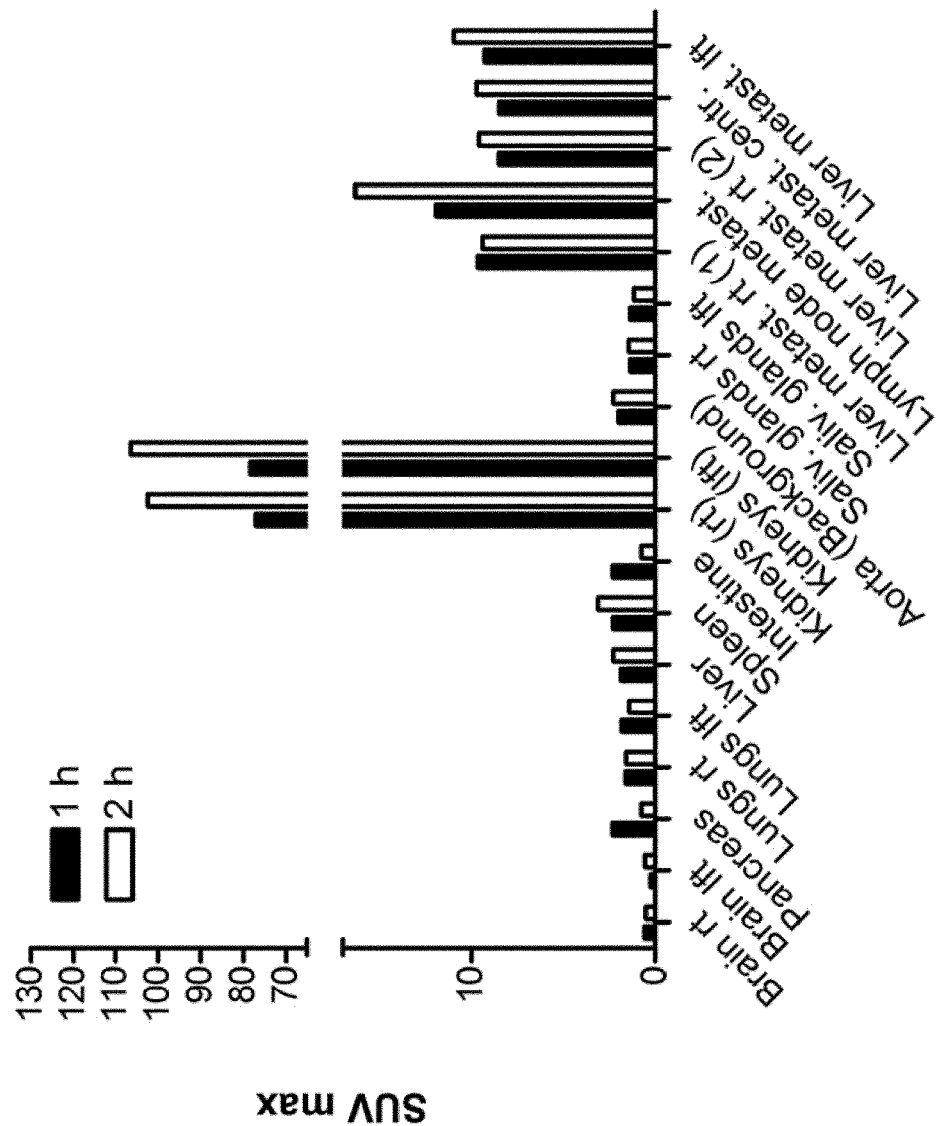

FIG. 23: Organ distribution of $^{68}$Ga-(MC-FA-012)₃ 1 and 2 hours after administration (SUV max) in patient 3 (rt=right, 1 ft=left).

Figure 24:
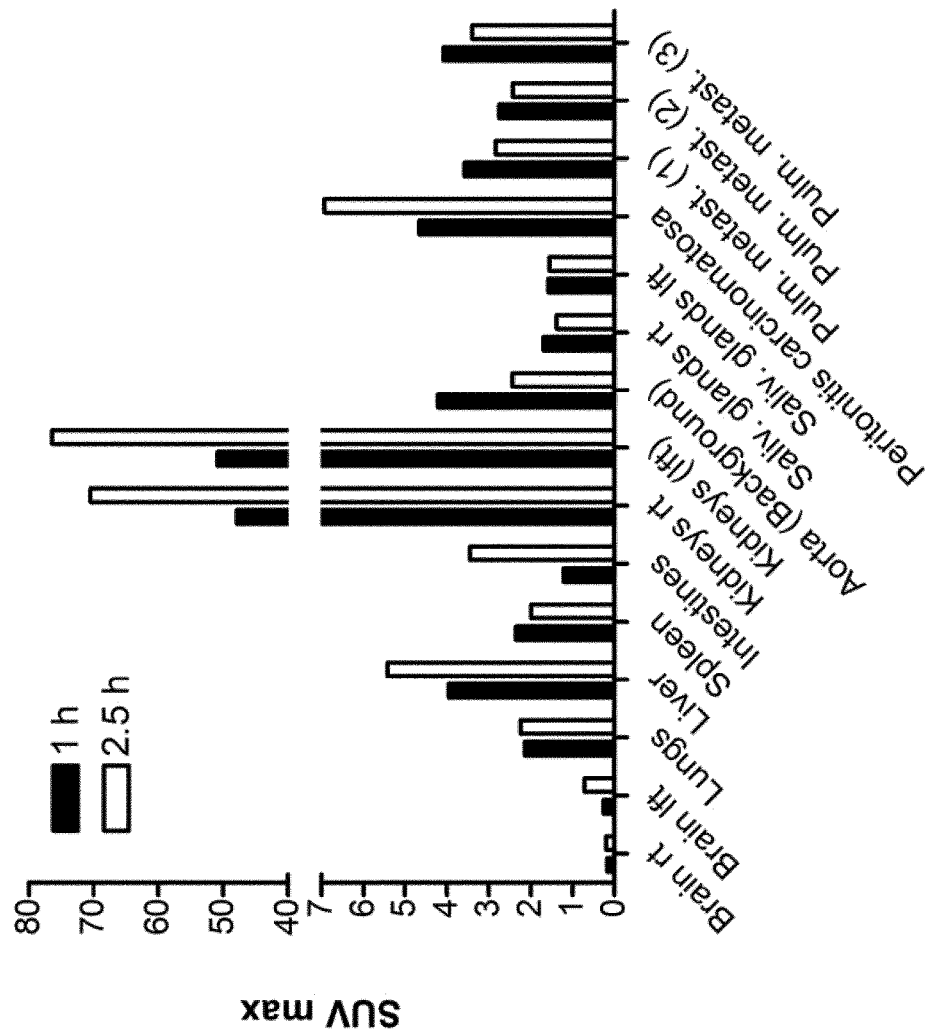

FIG. 24: Organ distribution of $^{68}$Ga-(MC-FA-012)$_3$ 1 and 2.5 hours after administration (SUV max) in patient 4 (rt=right, 1 ft=left).

Figure 25:
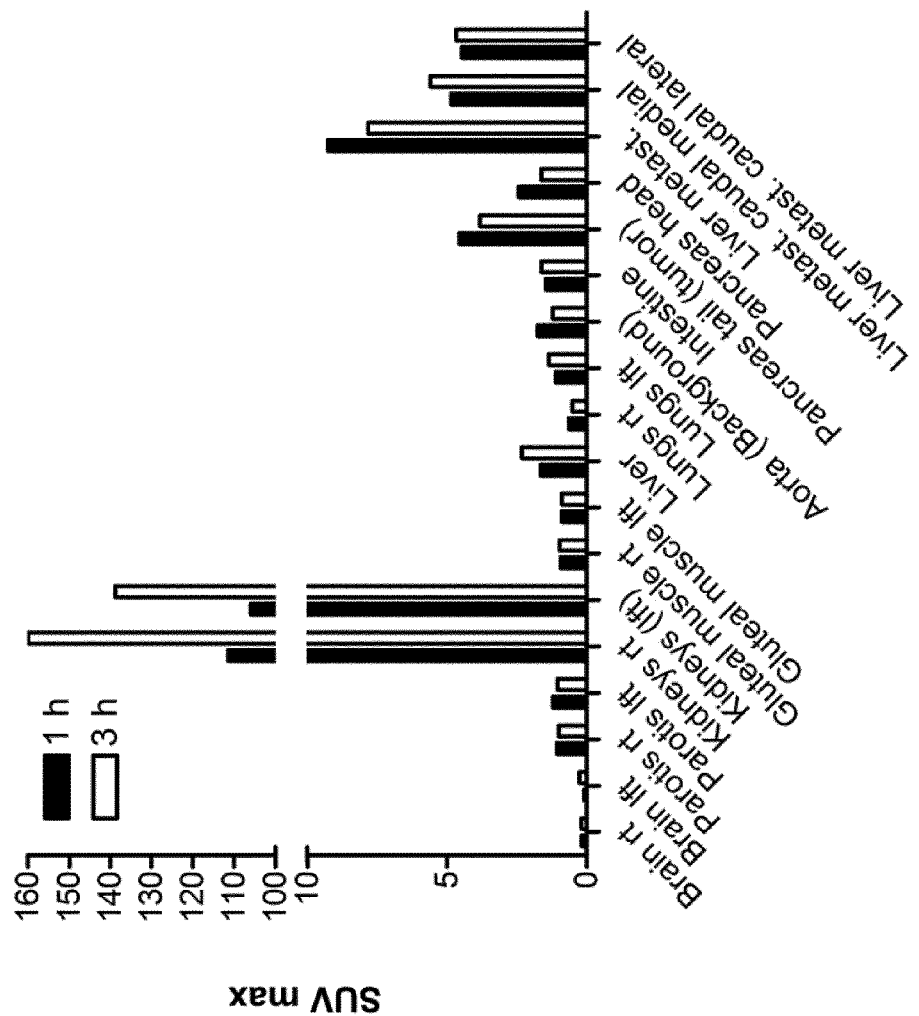

FIG. 25: Organ distribution of $^{68}$Ga-(MC-FA-012)$_3$ 1 and 3 hours after administration (SUV max) in patient 5 (rt=right, 1 ft=left).

Figure 26:
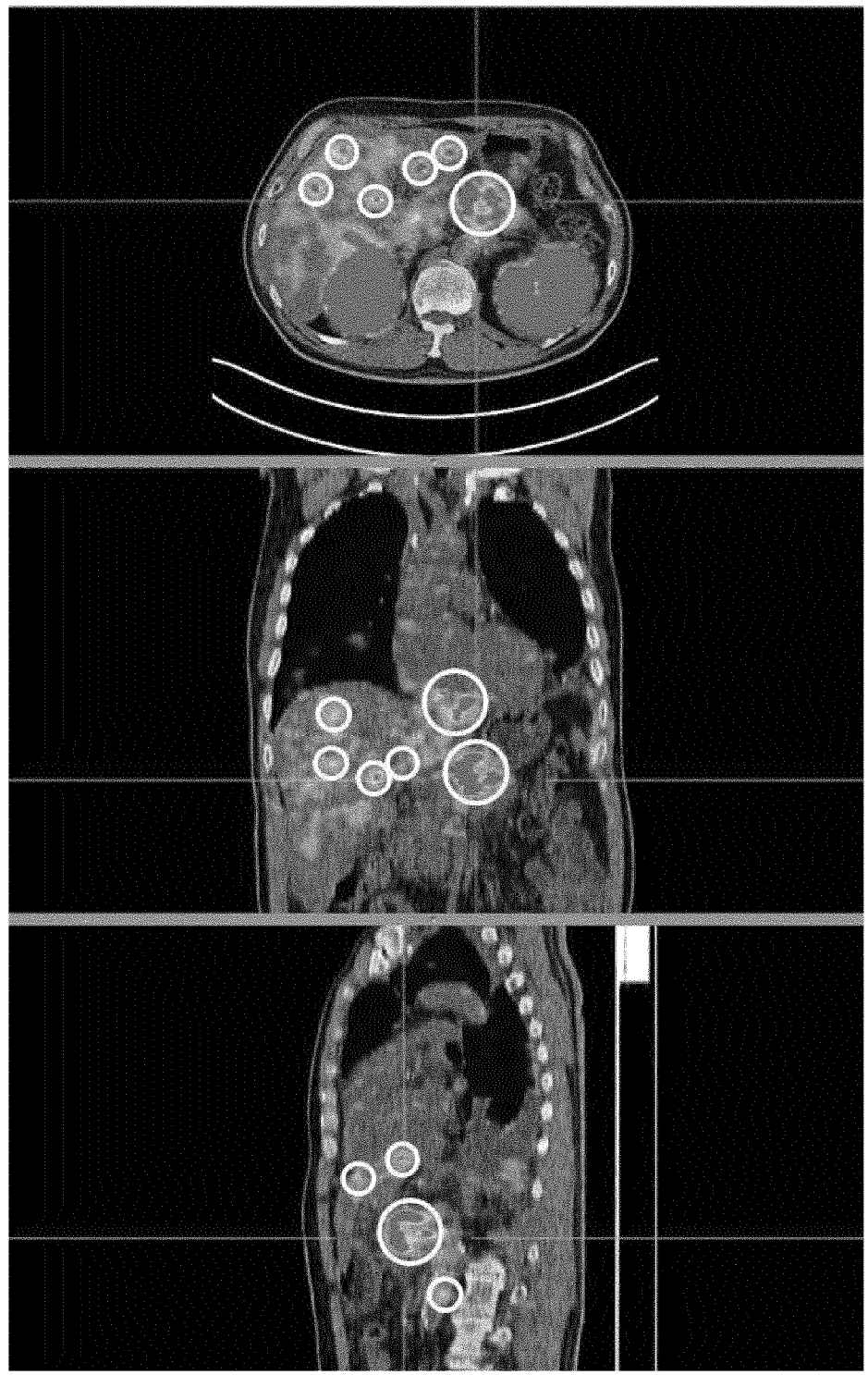

FIG. 26: Transaxial, coronal and sagittal views of exemplary PET scan (patient 3) 1 hour after injection of 64 MBq $^{68}$Ga-(MC-FA-012)$_3$. The scan shows a clear uptake in primary pancreatic tumor and liver metastasis. Location of tumor and metastasis marked by white circles.

Figure 27:
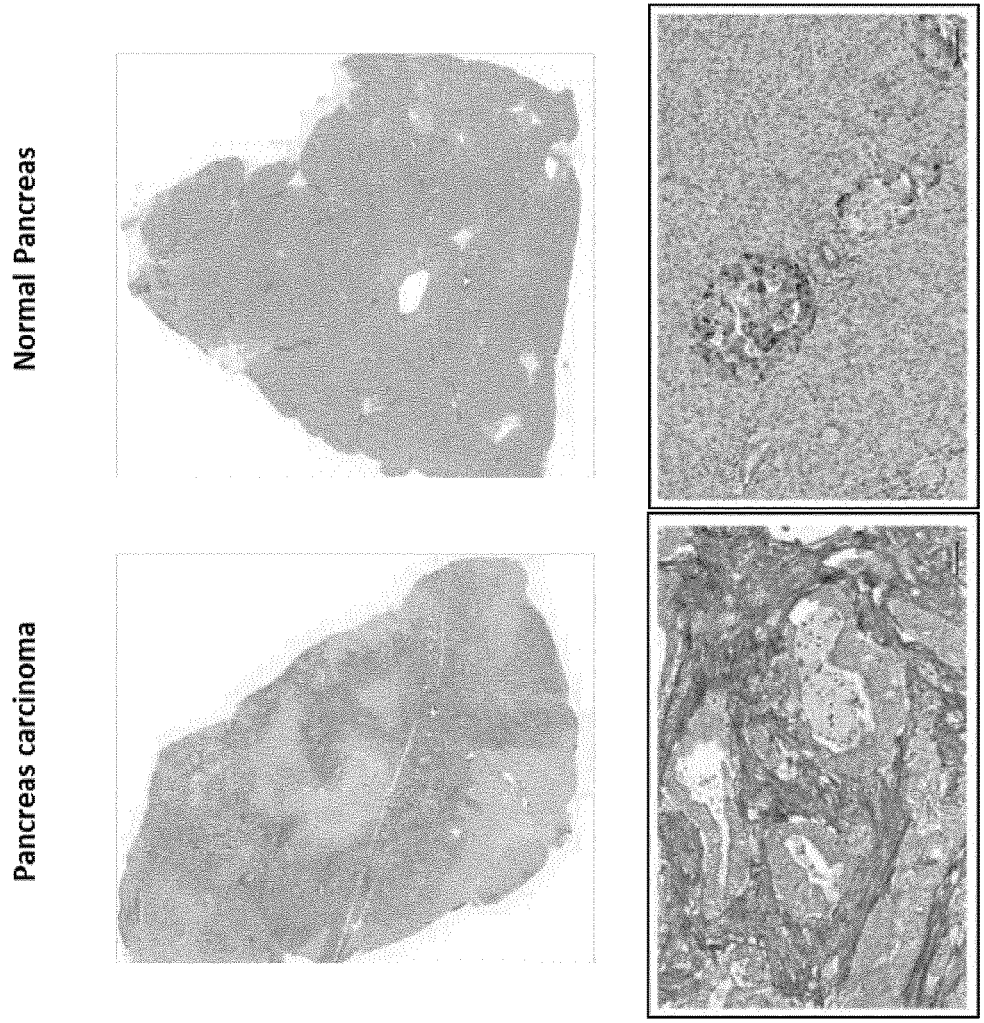

FIG. 27: Sections of pancreatic carcinoma and normal tissue stained with Seprase specific antibody.

Figure 28:
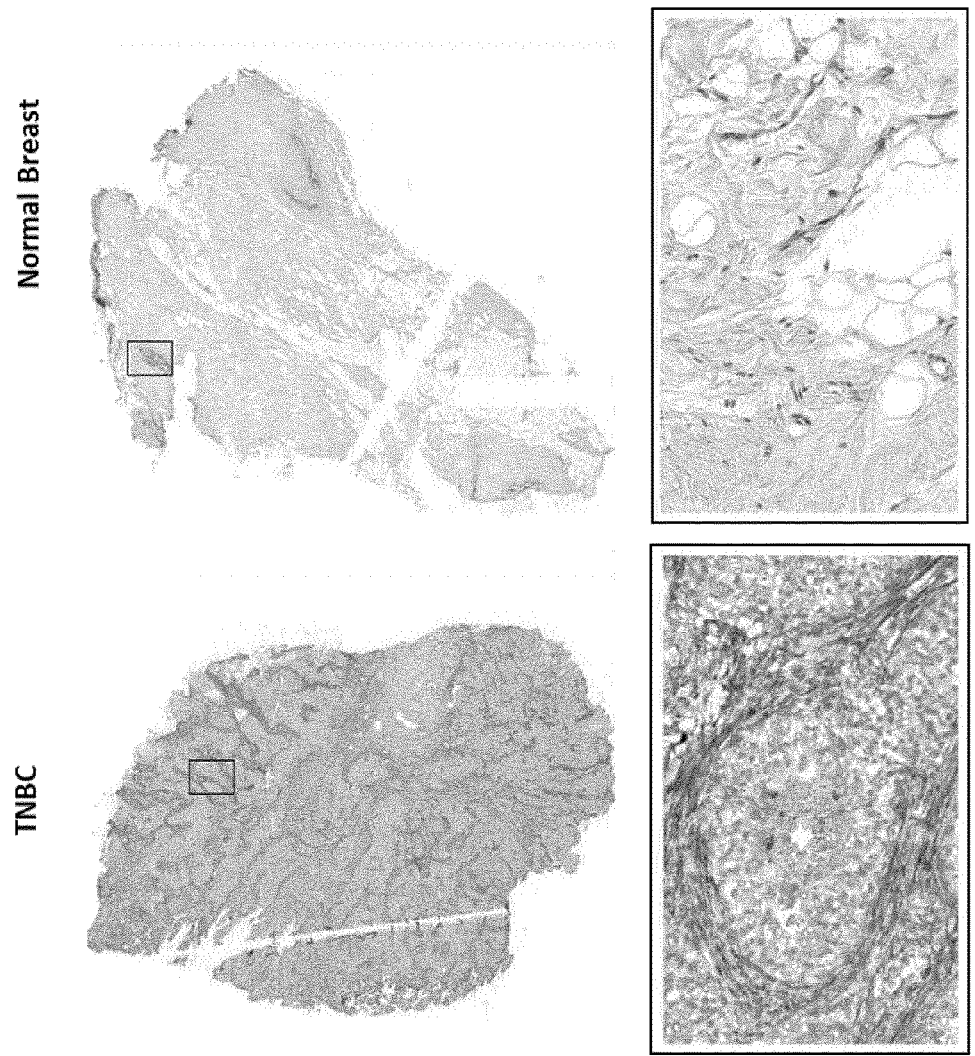

FIG. 28: Sections of triple negative breast carcinoma (TNBC) and normal tissue stained with Seprase specific antibody.

Figure 29:
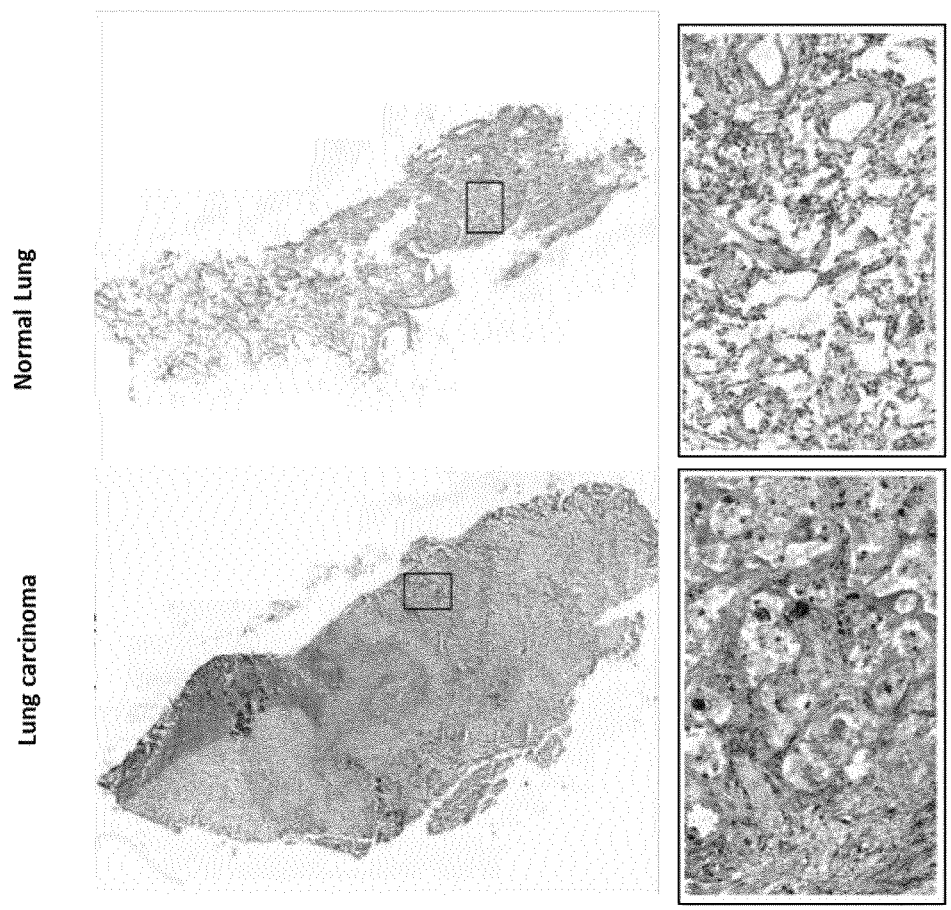

FIG. 29: Sections of lung carcinoma and normal tissue stained with Seprase specific antibody.

EXAMPLES

The techniques and methods used herein are described herein or carried out in a manner known per se and as described, for example, in Sambrook et al., Molecular Cloning: A Laboratory Manual, 2nd Edition (1989) Cold Spring Harbor Laboratory Press, Cold Spring Harbor, N.Y. All methods including the use of kits and reagents are carried out according to the manufacturers' information unless specifically indicated.

Example 1

Materials and Methods

Plasmid Constructions

CHO codon optimized full length human Seprase (NCBI accession number NP_004451) was synthesized by Geneart and subcloned into pENTRcht vector (Invitrogen). The plasmid was verified by DNA sequencing and named pENTR-huSeprase. Afterwards, the respective insert was shuttled into a piggy Bac transposon vector (PB53x EF1 Series) by Gateway cloning (Invitrogen) to generate transposon expression plasmids. These plasmids contain an EF1 alpha promoter to drive expression of the cDNA, an IRES-EGFP cassette and hygromycin as a selection marker. The plasmid was used for the generation of a stable Seprase expressing cell line.

Utilizing pENTR-huSeprase plasmid DNA as a PCR template, a cDNA fragment encoding the Seprase extracellular domain (amino acids 29-760) was amplified with a forward primer (5'-GCGCAAGCTTGCTGCGGCCCTC-CCGGGTGCAC-3') and a reverse primer (5'-GCGCAGCG-GCCGCGTCGGACAGGGAGAAGCACTGC-3') The PCR product, excluding the coding sequences of both the short cytoplasmic (amino acids 1-6) and hydrophobic transmembrane domains of seprase (amino acids 7-29), was inserted into a modified pCEP4 vector (Invitrogen). Compared to pCEP4, the modified vector additionally contains a Kozak consensus sequence, a hexahistidine (H6) fusion tag and the coding sequence of a secretion signal from the V-J2-C region of the mouse Ig kappa-chain for efficient secretion of the recombinant protein. The cDNA sequence of the Seprase extracellular domain was inserted, in frame, along with the N-terminal secretion signal and the C-terminal H6 tag, allowing efficient secretion, easy detection (by anti-His Antibody; Invitrogen) and rapid purification (by Ni-chelate affinity chromatography) of recombinant Seprase. The final construct was verified by DNA sequencing, named pCEP4-IgKappa-huSeprase-coCHO_26-760aa-H6 and used for the generation of recombinant soluble human Seprase (rhuSeprase).

Cell Lines

Chinese hamster ovarian cells (CHO-K1) were obtained from ATCC and grown in DMEM/F-12 medium supplemented with penicillin (100 units/ml), streptomycin (100 mg/ml) and 10% (v/v) heat-inactivated fetal bovine serum (FBS) (Invitrogen). Cells were maintained at 37° C. in 5% $CO_2$-humidified air atmosphere and passaged every 48-72 hours. MOCK or human Seprase expressing CHO-K1 cells (CHO-K1-MOCK and CHO-K1-huSeprase) were grown under the same conditions as the wild type cells with addition of 200 µg/mL hyromycin B (Invitrogen). For production of rhuSeprase the Freestyle™ CHO-S cell line from Invitrogen was used. This suspension cell line has been distinguished as a separate sub-clone from the common CHO-K1 cell line (D'Anna, 1996; D'Anna et al., 1997; Deaven & Petersen, 1973). Cells were cultured in polycarbonate, disposable, sterile Erlenmeyer flask with vented cap (125 mL or 500 mL) using 15-25% of the nominal volume at 120-135 rpm (Minitron Incubator shaker, Infors-HT) under standard humidified conditions (37° C. and 8% $CO_2$). Cells were sub-cultured when the density was approximately 1-1.5×10$^6$ viable cells/ml, typically every 48-72 hours in protein free chemically defined medium for CHO cells (CD CHO medium, Invitrogen) supplemented with 1×HT supplement, and 4 mM glutamine (Invitrogen).

Production of Recombinant Human Seprase

For large-scale expression of soluble recombinant human Seprase protein (rhuSeprase), the FreeStyle™ MAX CHO expression system (Invitrogen) was used, following the manufacturer's instructions. In brief, CHO-S cells were passed at 5-6×10$^5$ cells/ml, incubated under standard humidified conditions at 120 rpm-135 rpm overnight in a Minitron Incubator shaker (Infors-HT). On the following day the cells were diluted to 1×10$^6$ cells/ml in 150 ml into a 500 ml-shake flask on the day of transfection. 187.5 µg of pCEP4-IgKappa-huSeprase-coCHO_26-760aa-H6 plasmid DNA was added into 3 ml of OptiPro™ SFM and mixed. 187.5 µl of the FreeStyle™ MAX transfection reagent was diluted in 3 ml of OptiProSFM (Invitrogen) and mixed gently. Diluted FreeStyle™ MAX transfection reagent was added to diluted DNA solution, mixed gently, and incubated for 10 min at room temperature. DNA-FreeStyle™ MAX reagent complex was added slowly into the 500 ml-flask containing cells while slowly swirling the flask. Afterwards, transfected cell culture was incubated under standard conditions. Five to seven days after transfection, the supernatant was harvested and purified via conventional Ni-chelate affinity chromatography and size-exclusion chromatography using a HisTrap HP (GE Healthcare) and HiLoad 26/600 Superdex 200 prep grade SEC column (GE Healthcare) respectively. A portion of the purified protein was biotinylated by incubation with a 10 fold molar excess of EZ-Link Sulfo-NHS-LC-Biotin (Pierce) in PBS pH 8.8 for 2 h on ice. Protein was stored at −20° C. after buffer exchange to PBS supplemented with 5% mannitol (Roth) and 5% trehalose (Applichem).

Generation of Stable Seprase Expressing Cell Lines

Polyethylenimine, linear, MW 25000 (PEI) (Polysciences. Inc) reagent was used as the transfection reagent. Stable cell lines were established with the PiggyBac transposon system. Briefly, this system consists of a donor vector carrying an artificial transposon with a mammalian expression cassette for the recombinant transgene and a helper vector driving transient expression of the PB transposase (PBase) (Invitrogen). One day before transfection, $3 \times 10^5$ CHO-K1 cells were plated in 2 ml of growth medium per well in a six-well plate. CHO-K1 cells were co-transfected with 2 µg transposon vector plasmid and 0.8 µg of transposase vector plasmid. Three days post-transfection, cells were split and placed in media containing 200 µg/ml hygromycin B (Invitrogen). After 2 weeks of hygromycin selection, the transfection efficiency and the target expression was analyzed by flow cytometry, western blot and immunofluorescence analysis. The functionality was tested by enzyme activity assay using Z-Gly-Pro-AMC substrate (Bachem).

Flow Cytometry Analysis

For flow cytometry, $1 \times 10^6$ cells were collected, washed once with FACS buffer (PBS+0.5 M EDTA+5% FBS) and incubated with an antibody against human Seprase (clone 1E5, Abnova; 1:50 dilution) or with different concentrations of Thioredoxin-A (Trx) miniprotein fusions for 1 h on ice. To analyze the binding of tetramerized miniproteins, biotinylated miniproteins were pre-incubated with a fivefold molar excess of Streptavidin-APC (Affymetrix eBioscience) for 10 min at room temperature. After incubation cells were washed thrice with FACS buffer. Cell treated with tetramerized miniproteins were used directly for flow cytometry analysis. To analyze Seprase expression or monovalent miniprotein binding, cells were stained with a secondary Cy5-labeled anti-mouse antibody (Dianova) or with PE-labeled anti-H6 antibody (R&D Systems, detects internal H6 tag within the Trx-miniprotein fusion). After 30 min cells were washed again with FACS buffer and analyzed using a FACS Canto II device (Becton Dickinson). The analysis gate was set on viable cells identified according to forward scatter/side scatter characteristics. Data were analyzed using FlowJo software (Version 10, Tree Star Inc.).

Immunohistochemistry

Tumors were immediately excised, transferred into embedding cassettes and fixed overnight at 4° C. in 4% Roti-Histo-Fix (pH 7) (Roth). After fixation, the tumors were washed in 70% ethanol to remove excess fixation solution. Thereafter, tumors were dehydrated in an ascending alcohol series and paraffin embedded in a tissue processor. Serial section (3 µm thick) of the embedded tumors was performed with a microtome. The sections were mounted on glass slides and deparaffinized and rehydrated in a descending alcohol series. Then, sections were boiled for 20 min with 10 mM citrate buffer (pH 6) in a microwave. After washing with 1×PBST, unspecific binding was blocked with 3% BSA in PBST for 30 min. 1:500 polyclonal anti-SMA antibody (Abcam) or 1 µM biotinylated miniprotein, which was preincubated with Streptavidin-Cy3 (Rockland) before for tetramerization, was added and incubated overnight at 4° C. After washing the sections three times with 1×PBST anti-SMA antibody binding was detected with the secondary antibody IgG anti-rabbit-FITC diluted 1:200 (Dianova). Secondary antibodies were incubated for 1 h at room temperature in the dark. Finally, sections were washed three times with PBS and subsequently incubated with Hoechst dye (Sigma-Aldrich), diluted 1:5000 in 1×PBS for 10 min and mounted in mounting medium (Darko).

To evaluate the expression levels of Seprase in TNBC, lung- and pancreas carcinoma immunohistochemical analyses were performed. As positive control CHO-K1-huSeprase tissues with positive expression levels of Seprase and as negative control human colon sections were used.

For paraffin embedding pancreas tissue 3 µm thick sections were deparaffinized with xylene and graded ethanol. Antigen retrieval was performed by heating the sections in 10 mM sodium citrate buffer, pH 6.0+0.05% Tween-20 at 120° C., cooled down for 10 min. Samples were quenched for 15 min in PBS+0.3% $H_2O_2$. Frozen tissue sections (breast and lung tissue) were sectioned at 5-8 µm in a cryostat. The sections were thawed for 10 min at room temperature, rehydrated for 5 min in PBS and quenched for 10 min in BLOXALL (Vectorlabs).

All sections were incubated with 10% normal goat serum at room temperature for 30 min to block non-specific reactions. This was followed by incubation with polyclonal rabbit anti-human Seprase antibody (Sigma) diluted to 0.5 µg/ml for 1 h at room temperature. After washing with PBS the sections were incubated for 30 min with the secondary antibody (Power-Vision HRP anti-rabbit). The localization of immunostaining was demonstrated by incubation with the Vector NovaRED system (Vector Laboratories). Counterstaining with Mayer's Haematoxylin and dehydration of the sections were done with a Multistainer ST5020 (Leica). Afterwards, slides were mounted with XTRA-Kitt Medite mounting medium.

Phage Display Selections Vs. rhuSeprase

A randomized knottin library comprising approximately $1 \times 10^{10}$ individual variants was applied for phage display selections vs. rhuSeprase. The library is based on the open chain trypsin inhibitor II from *Momordica cochinchinensis* (oMCoTi-II, (Avrutina, Schmoldt et al. 2005)). Three selection rounds were carried out using rhuSeprase immobilized on Maxisorp™ immuno tubes (Thermo Scientific) or via Streptavidin coated magnetic beads (Dynabeads 280 Streptavidin, Life Technologies).

Production of Miniprotein Variants

Biotinylated miniprotein variants were purchased from Pepscan. In these cases the miniproteins were generated by conventional solid-phase peptide synthesis followed by thermodynamic folding to the native cystine-knot structure. In all other cases miniproteins were produced recombinantly using a Thioredoxin-A (Trx) based fusion system in combination with *E. coli* Shuffle™ T7 Express strain (NEB) that allows disulfide bond formation in the cytoplasm of the bacterial host (Lobstein, Emrich et al. 2012). For semi-preparative or analytical recombinant synthesis, the miniprotein variant encoding genes were cloned into pET-32-LibEx vector via unique Bam HI and Apa I restriction sites to yield a tetrapartite fusion consisting of thioredoxin-A, a His-tag (H6), an S-tag and the miniprotein gene. For semi-preparative production of miniproteins expression was performed in 1 l shake flasks using standard lysogeny broth (LB) medium, whereas analytical scale production (e.g. for hit identification or analysis of MC-FA-010 alanine mutants) was carried out in 96 well plates using autoinduction medium (MagicMedia™, Life Technology). After expression, cells were harvested and lysed with lysozyme or by sonication in combination with a freeze/thaw cycle. In both cases cleared cell lysates were subjected to a heating step at 80° C. for 10 min to remove a large amount of host cell proteins. The resulting protein preparation was either directly used for ELISA binding analysis (e.g. for hit identification purposes) or further purified via Ni-chelate affinity chromatography using Ni-NTA spin columns (Qiagen, analytical scale) or 5 ml HisTrap HP columns (GE Healthcare, semi-preparative scale). For the generation of tag-free miniproteins, trx-miniprotein fusions were cleaved with thrombin (Sigma) by overnight incubation at 37° C. with 0.5 U Thrombin/mg fusion proteins. Miniproteins could then be isolated by HPLC using a TSKgel ODS-120T column (Tosoh Bioscience). The final miniprotein preparations, gained after freeze-drying of the respective HPLC fractions, were analyzed by mass spectrometry and analytical size exclusion chromatography using a BioSep-SEC-S2000 column (Phenomenex). Yields were calculated by weighing or OD (280 nm) measurements.

Western Blotting $1 \times 10^5$ cells were cultured on a culture-dish, washed once with cold 1×PBS and lysed in 500 µL 4×SDS lysis buffer (250 mM Tris-HCl, 34% Glycerol, 8.2% SDS, 5% β-mercaptoethanol). Cells were scrapped with a cell scraper and in order to remove cellular debris, lysates were centrifuged for few minutes at 14000×g at 4° C. Thereafter the lysates were sonicated. An aliquot of the lysate was boiled with 4×SDS-lysis buffer added with bromphenolblue and analyzed by SDS-PAGE and subsequent western blotting. Following antibodies were used for detection: as primary antibody: anti-Seprase (Abcam), anti-His (Abcam) or anti-β-Actin and as a secondary antibody anti-mouse-HRP (clone).

Hit Identification

After three rounds of phage display selection the resulting pools were sub-cloned in the pET-32-LibEx expression vector to allow for the identification of putative rhuSeprase binders independently from the phage background. To this end, the respective miniprotein gene pools were PCR amplified with specific oligonucleotides. The resulting PCR product was purified, cleaved with Bam HI and Apa I restriction enzymes and ligated with similarly digested expression vector. After transformation of E. coli Shuffle™ T7 Express individual clones were picked and Trx-fusion proteins were produced in a 96well format as described above. For analysis of binding an ELISA assay was performed. Therefore a MaxiSorp 96 well plate (Nunc/Thermo Fisher Scientific) was coated with target protein or BSA (each 100 µl of 5 µg/ml protein solution in 50 mM Na-Carbonat, pH 9.4). Binding to target protein corresponds to "signal" and binding to BSA corresponds to "noise". For normalization of single plates binding of MC-Myc-010 (Myc-binding cystine knot miniprotein) and Anti-cMyc antibody (clone 9E10) was analyzed in triplicates. Coating was performed over night at 4° C. Wells were washed 3 times with 300 µl phosphate buffered saline containing 0.1% Tween 20 (pH 7.4,PBS-T). Wells were then blocked for 2 h with Blocking Solution (Sigma Aldrich). After a washing step (3×PBS-T) Trx fusion protein containing lysates were diluted 1:5 in and incubated for 1 h at 4° C. with coated proteins. Washing and incubation step was repeated using anti-S-tag antibody (1:2000 in PBS, abcam). Before detection washing step was performed twice (3×PBS-T and 3×PBS). Detection was carried out using 3, 3',5,5'-Tetramethylbenzidine Liquid Substrate (TMB solution, Sigma-Aldrich) and increase of absorption at 450 nm (detected in Tecan M200 Pro ELISA reader). Expression of single clones was analyzed by 96-well E-PAGE electrophoresis (Life Technologies) and quantification of protein bands via ImageQuant TL software package (GE Healthcare). For ranking of proteins signal to noise ratios of ELISAs were calculated and correlated with expression values. Top 30 clones were then used for further analysis.

Binding Analysis Via ELISA

ELISAs were performed to assess and compare the binding properties and specificity of miniprotein variants. To this end, either recombinant proteins or whole cells have been used. For whole cell ELISA analysis $5 \times 10^5$ cells were seeded on each well of a 96-well flat bottom plate (Corning). Therefore, cells were incubated for 20 hours at 37° C. in 5% $CO_2$-humidified air atmosphere. Afterwards, the wells were blocked with 5% milk powder/PBS for 1 hour at RT. After removing the blocking buffer Trx-miniprotein solution was added to each well, and incubated with the cells for 1 hour at RT. Subsequently, the wells were washed 6 times extensively with PBS-T (PBS+0.1% Tween-20) and the amount of bound miniproteins was detected with horseradish peroxidase (HRP)-conjungated anti-S-tag antibody (Abcam). 3,3',5,5'-Tetramethylbenzidin (TMB) (Sigma) was used as chromogenic substrate. HRP enzyme reactions were stopped with 0.2 M HCl after approximately 20 min and the plate was measured in a Victor V3 plate reader (Perkin Elmer) at 450 nm. For competition studies 0.1 µM Trx-MC-FA-010 fusion protein was pre-mixed with different concentrations of solitary MC-FA-010 miniprotein (1-200 µM) before incubation with cells.

For protein based ELISA analysis 5 µg of the respective recombinant protein (rhuSeprase; streptavidin: Sigma; DPP-IV: R&D Systems, BSA: Eurobio) were immobilized per well of a MaxiSorp™ plate (Nunc) by overnight incubation in coating buffer at 4° C. After washing thrice with 300 µl PBS-T/well on a Hydrospeed plate washer (Tecan) the wells were blocked with 1×Casein solution (Sigma, diluted in PBS) for 2 h at RT. Subsequently, the wells were washed as indicated above. 100 µl of the respective Trx-miniprotein fusion diluted in PBS-T was then added and incubated for 1 h at 4° C. Simply heat-step purified protein was diluted 1:5, affinity purified proteins were applied in defined concentrations ranging from 0.39-50 nM. For competition ELISAs a fixed concentration of 3 nM Trx-miniprotein fusion was mixed with varying concentration (0.64-3167 nM) of solitary miniprotein before incubation. Binding of the Trx-fusion was detected after a PBS-T washing procedure using HRP coupled anti S-tag antibody as described above. Apparent Kd was calculated using Sigmaplot 10 and an one site saturation binding model for fitting of the data.

SPR Analysis

To obtain insights of the kinetic binding properties surface plasmon resonance (SPR) analysis was performed on a Biacore T100 device (GE Healthcare). Therefore, rhuSeprase was immobilized onto a CM5 chip via NHS/EDC mediated coupling as described by manufacturer at 10 µl/min for 420 sec. Binding of MC-FA-010 in varying concentrations (37; 111.1, 331.3, 1000 and 3000 nM) to immobilized rhuSeprase was measured over a time period of 90 seconds for association and dissociation. Kd values were calculated using the provided software.

Kinetics and affinity of monomeric and oligomeric MC-FA-010 and variants thereof to recombinant human Seprase (rhuSeprase) were determined using surface plasmon resonance spectroscopy (Biacore T-100, GE Healthcare). RhuSeprase (20 µg/ml in PBS, 5% mannitol, 5% trehalose) was immobilized on an amino reactive Series S Sensor Chip CM5 (GE Healthcare). For binding analysis of monomeric Microbodies rhuSeprase was loaded to a maximum of 7500 RU, for oligomeric Microbodies to a maximum of 700 RU. Monomeric Microbodies were measured using a multi cycle kinetic method in a concentration range of 3.125 to 1000 nM based on expected dissociation constant. Association step was measured over a time period of 60-90 seconds, dissociation over 420 seconds. Trimeric Mircobodies were measured using a single cycle kinetics method in a concentration range of 0.3125 to 5 nM (association for 90 seconds, dissociation 420 seconds). Binding kinetics and steady state analysis were calculated using a 1:1 binding model (Biacore T-100 Evaluation Software, GE Healthcare).

Alanine Scan Mutagenesis of MC-FA-010

In order to gain insights into the structure-activity relationship of the seprase binder MC-FA-010 an alanine scan mutagenesis was performed. Therefore, every single amino acid of the variable region was exchanged by alanine on the DNA level. The mutant genes were synthesized by Geneart as DNA Strings™ and directly cloned into pET-32-LibEx expression vector via unique Bam HI and Apa I restriction sites. Production of alanine variants was done in 96well microtiter plates using the Shuffle™ T7 Express *E. coli* strain as described above. After purification with Ni-NTA spin columns (Qiagen) the binding properties of the variants were analyzed via ELISA and compared to the MC-FA-010 wildtype miniprotein.

Affinity Maturation

Based on the obtained data from the alanine scan mutagenisis and the identified binding motif of MC-FA-010/-012 a second phage library was generated. In this library, the critical amino acid positions for seprase binding were kept constant (Y, W and the GRGP sequence) whereas all other positions of the binding loop were randomized using all possible amino acids except cysteine. This library was screened again against recombinant soluble human seprase, applying four different conditions that vary with respect to stringency (monovalent or polyvalent display, with or without competition with free MC-FA-012 miniprotein, different washing conditions). After three selection cycles all pools were cloned into the pET-32 expression vector. For each pool 96 clones were expressed and analyzed using the hit identification process described above. 26 of the top-ranked clones were selected, produced in higher amounts and analyzed in more detail.

Biodistribution and Tumor Targeting Analysis of Microbody® AlexaFluor-680 Conjugates Using In Vivo Near-infrared Optical Imaging For in vivo imaging assays female Fox n1 nu mice (6-8 weeks of age, Harlan, Envigo) were used. The experiments were performed according to national regulations and approved by the local animal experiments ethical committee. Subconfluent CHO-K1-huSeprase cells were harvested and resuspended in PBS to a density of $1\times10^7$ cells/ml. Prior to inoculation, cell viability was tested by 0.4% trypan blue exclusion assay (viable cells>90%). For subcutaneous injection $1\times10^6$ CHO-K1-huSeprase cells in 100 µl PBS were mixed with 100 µl Matrigel (Corning) and injected into the right side of the limb. When tumor volumes reached 600-800 mm$^3$, animals were randomly separated into several groups for different treatments (n=3 per each group). Then, 1.67 nmol AF680-(MC-FA-012)$_3$ or the control Microbody® AF680-(MC-FA-0116)$_3$ were injected intravenously. At different time points after the injection, mice were anaesthetized by inhalation of isoflurane. In vivo imaging was conducted using a Xenogen IVIS Spectrum imaging System (Perkin Elmer, USA). Maximal near infrared signals (NIRF) were quantified using Living Image 2.5 (Xenogen, Perkin Elmer) image analysis software. For ex vivo NIRF imaging, the mice were sacrificed, and the tumor and major organs of each mouse were excised, weighed and analyzed by Xenogen IVIS System.

Immunofluorescence Analysis

1 µM biotinylated MC-FA-012 and the control MC-FA-0116 were preincubated with Streptavidin-Cy3 (Rockland) (molar ratio 5:1) for 30 min at room temperature. Cryosections (6 µm) of tissues were fixed with acetone and blocked with 3% BSA/PBS to prevent non-specific binding. Then tissues were stained with anti-SMA antibody (Abcam) to detect activated fibroblasts and with the Microbody-Streptavidin mix for 30 min at 37° C. Sections were rinsed afterwards and incubated for 30 min with Alexa 488 conjugated secondary antibodies (Abcam) at 37° C. Finally, sections were washed again, incubated with Hoechst 33258 (Sigma-Aldrich) to detect nuclei, washed again twice and mounted in fluorescence mounting medium (Dako). Sections were then examined with an inverted fluorescence microscope (Zeiss AxioObserver.Z1).

Small Animal PET-Imaging and Organ Distribution $^{177}$Lu-Labeling of DOTA-(MC-FA-012)$_3$ 2.5 nmol MC-FA-012 trimer was dissolved in 50 µl 0.1 M sodium acetate buffer pH 5.0 and mixed with 1 µl of an aqueous solution of 20% ascorbic acid. 2.5 µl of $^{177}$LuCl$_3$ in 0.4 M sodium acetate buffer pH 5.0 (~25 MBq) were added. The mixture was heated for 15 min at 95° C. and diluted to a total volume of 2.5 ml using 0.9% saline. Radiolabeling was performed without any separation of labeled and unlabeled compound. The radiochemical yield was determined by analytic RP-HPLC. $^{177}$Lu-(MC-FA-012)$_3$ corresponds to $^{177}$Lu-labeled DOTA-(MC-FA-012)$_3$.

$^{68}$Ga-Labeling of DOTA-(MC-FA-012)$_3$ $^{68}$Ga was gained from a $^{68}$Ge/$^{68}$Ga generator as [$^{68}$Ga]GaCl$_3$ in 0.6 M HCl. 5 nmol MC-FA-012 trimer and 10 µl of an aqueous solution of 20% ascorbic acid were mixed with 550 µl of the $^{68}$Ga-eluate and neutralized with 160 µl 2.5 M sodium acetate buffer (pH 8) to a final pH of 3.5. The mixture was heated for 13 min at 95° C., purified using a solid phase extraction cartridge (Agilent Varian Bond Elut Plexa) and diluted in 0.9% saline. Radiolabeling was performed without any separation of labeled and unlabeled compound. The radiochemical yield was determined by analytic RP-HPLC. $^{68}$Ga-(MC-FA-012)$_3$ corresponds to $^{68}$Ga-labeled DOTA-(MC-FA-012)$_3$.

In Vivo Testing of Radiolabeled DOTA-(MC-FA-012)$_3$

For in vivo experiments, 8 week old BALB/c nu/nu mice (Charles River) were subcutaneously inoculated into the right trunk with $5\times10^6$ CT26-huSeprase cells, respectively. For imaging experiments (n=2), $5\times10^6$ CT26 wildtype cells were additionally injected into the left trunk as a control. When the size of the tumor reached approximately 1 cm$^3$, the radiolabeled compound was injected via the tail vein (~10 MBq for small-animal PET imaging; ~1 MBq for organ distribution).

Organ Distribution of $^{177}$Lu-(MC-FA-012)$_3$

For organ distribution, the animals (n=3 for each time point) were sacrificed after indicated time points (from 30 min to 24 h). The distributed radioactivity was measured in all dissected organs and in blood using a γ-counter. The values are expressed as percentage injected dose per gram (% ID/g).

Small-animal PET Imaging with $^{68}$Ga-(MC-FA-012)$_3$

PET imaging was performed using the small-animal PET scanner Inveon PET (Siemens). After a 15 min transmission scan the anaesthetized mice were injected with approximately 2.5 nmol $^{68}$Ga-(MC-FA-012)$_3$ (~10 MBq). Within the first 60 min a dynamic scan was performed, followed by a static scan from 120 to 140 min after injection. Images were reconstructed iteratively using the 3D-OSEM+MAP method (Siemens) and were converted to standardized uptake value (SUV) images. Quantitation was done using a ROI technique and expressed as SUVmean.

Diagnostic and Therapeutic Purposes $^{68}$Ga-Labeling of DOTA-(MC-FA-012)$_3$

68 Ga (half-life 68 min; energy of positrons max. 1.9 MeV [β+89%]) was gained from a $^{68}$Ge/$^{68}$Ga generator as [$^{68}$Ga]GaCl$_3$ in 0.6 M HCl. 2.5 nmol DOTA-(MC-FA-012)$_3$ and 10 µl of an aqueous solution of 20% ascorbic acid were added to 1 ml of the $^{68}$Ga-eluate (~0.8-1 GBq) and diluted with 280 µl 2.5 M sodium acetate buffer (pH 8) to a final pH of 3.5. The mixture was incubated at 95° C. for 15 min, purified using a solid phase extraction cartridge (Agilent Varian Bond Elut Plexa) and diluted in 0.9% saline. Radiolabeling was performed without any separation of labeled and unlabeled compound. The radiochemical yield was determined via analytical RP-HPLC.

$^{177}$Lu-Labeling of DOTA-(MC-FA-012)$_3$ $^{177}$Lu (half-life 6.71 d; energy of electrons max. 497 keV [β⁻79%]; energy of photons max. 113 keV [6%], 208 keV [11%]) was purchased from ITG GmbH Garching as [$^{177}$Lu]LuCl$_3$ in aqueous 0.04 M HCl solution. 15 nmol DOTA-(MC-FA-012)$_3$ were dissolved in 100 µl 0.4 M sodium acetate buffer pH 5.0 and mixed with 10 µl of an aqueous solution of 20% ascorbic acid. 70 µl of $^{177}$LuCl$_3$ in 0.4 M sodium acetate buffer pH 5.0 (~2.5 GBq) were added. The mixture was incubated at 95° C. for 15 min and diluted to a total volume of 5 ml using 0.9% saline. Radiolabeling was performed without any separation of labeled and unlabeled compound. The radiochemical yield was determined by analytic RP-HPLC and instant thin layer chromatography (ITLC-SG) with a solution of 0.5 M sodium citrate pH 5 with and without 10% methanol as solvent.

PET Imaging

Diagnostic imaging was performed using $^{68}$Ga-(MC-FA-012)$_3$, which was applied intravenously (2.5 nmol, 63-359 MBq). Variation of injected radiotracer activity was caused by the short half-life of $^{68}$Ga and variable elution efficiencies obtained during the lifetime of the $^{68}$Ge/$^{68}$Ga generator. The patients were investigated 1 and approx. 3 hours after administration of $^{68}$Ga-(MC-FA-012)$_3$ using the PET/CT scanner Siemens Biograph-mCT Flow. After performing a CT scan for attenuation correction, static emission scans, corrected for dead time, scatter and decay, were acquired. Images were reconstructed iteratively and were converted to standardized uptake value (SUV) images.

Medical imaging after administration of $^{177}$Lu-(MC-FA-012)$_3$ was performed using the gamma camera GE Millenium VG5 Hawkeye one day after intravenous injection of approx. 2.5 GBq.

Example 2

Engineering of the Human FAPα Binding oMCoTi-II Mutant MC-FA-010

FAPα binding cytine knot miniprotein MC-FA-010 was isolated from a highly diverse phage based oMCoTi-II library (containing 1×10$^{10}$ individual variants). Sequence analysis of an enriched clone after three selection rounds revealed a miniprotein sequence with 35 amino acid (aa) length (FIG. 1).

To analyze the structure function relationship of the identified miniprotein an alanine scan mutagenesis was performed (FIG. 2A+B). Concentration-dependent binding of MC-FA-010 variants to human Seprase was measured in a direct ELISA setup using recombinant target protein and EC50 values were calculated by means of a one-site-saturation binding model (Sigma plot 10). FIG. 2A shows a summary of all binding data. Binding of alanine mutants are shown as relative binding compared to parental sequence of MC-FA-010. Preserved/increased binding (respectively weak loss of binding) is shown in green colors, weak and moderate binding in orange and no binding (complete loss of binding) in red.

The alanine scan mutagenesis revealed a binding motif consisting out of two aromatic and four aliphatic amino acids (YXXWXXGRGP, FIG. 2B). High specificity of the given sequence is shown as a single alanine exchange completely abolishes binding of MC-FA-010 to human Seprase. One variant, MC-FA-012 (K2A), showed an even higher affinity (160%) to Seprase compared with the wild-type Microbody™ MC-FA-010. This variant was also included in further functionalization approaches.

Example 3

Target Binding of the Human FAPα Binding oMCoTi-II Mutant MC-FA-010 and Variants Thereof MC-FA-010 Shows Affinity to Human Seprase in Nanomolar Range Affinity of MC-FA-010 binding to recombinant human Seprase was measured using concentration-dependent ELISA. Plates were coated with the soluble fraction of human Seprase and MC-FA-010 was added as a fusion protein to thioredoxin (Trx-MC-FA-010) in a concentration range of 0.39 to 50 nM. Detection of bound miniprotein was achieved via anti S-Tag-HRP conjugated antibody (S-tag is provided by thioredoxin fusion expression system, FIG. 3A). EC50 values were calculated using the one-site-saturation binding model in Sigma plot 10. In addition binding of 3 nM Trx-MC-FA-010 was competed with soluble monovalent MC-FA-010 in a range of 0.64-3167 nM (FIG. 3B) showing a specific competition of the binding. Both, EC50 and IC50 value, show a binding affinity of MC-FA-010 to human Seprase in the nanomolar range.

Those experiments show a specific binding of MC-FA-010 to human Seprase in general. As a next step a more detailed analysis of binding kinetic was performed using surface plasmon resonance technology (SPR). Therefore, recombinant human Seprase was immobilized on a CM5 chip (GE Healthcare) with an amino reactive surface. Association and dissociation of soluble monovalent MC-FA-010 was measured in a concentration series (37, 111.1, 333.3, 1000 and 3000 nM) using a Biacore T100 system. Association and dissociation data was fitted and corresponding dissociation constant and kinetic values (Kon, Koff and Kd) was calculated using the provided software of the system (FIGS. 4A and B). The SPR analysis reveals a dissociation constant of approximately 560 nM and therefore confirms the previously measured affinity in nanomolar range as analyzed via ELISA.

MC-FA-010 Shows High Selectivity for Human Seprase

To analyze the selectivity of MC-FA-010 for human Seprase, binding to the closely related dipeptidyl peptidase IV (DPP IV, CD26) was studied. DPP IV is a 88 kDa membrane bound glycoprotein which also can be proteolytically cleaved to a soluble form lacking 38 aa at the amino terminus. FIG. 5A shows a structural overlay of Seprase depicted in green and DPP IV depicted in cyan or grey (Pymol). Seprase and DPP IV share 52% sequence identity and 71% similarity. Selectivity of MC-FA-010 for Seprase was analyzed via ELISA. Human Seprase respectively DPP IV was coated and binding of Trx-MC-FA-010 was measured in a concentration series of 0.1 to 100 nM.

As expected MC-FA-010 binds strongly and selectively to Seprase. Only a very weak signal could be detected for MC-FA-010 binding to DPP IV in the highest concentration measured (FIG. 5B). Thus, MC-FA-010 shows a high selectivity for Seprase.

MC-FA-010 Specifically Binds to Seprase-expressing Cells

To investigate binding of MC-FA-010 to human Seprase-overexpressing CHO-K1-cells (CHO-K1-Seprase), an immunofluorescence staining was conducted. Target-negative CHO-K1-MOCK cells and a negative control Microbody™, were used as controls to exclude unspecific binding of the Microbody™ to unrelated proteins on the cell surface. Before incubation with the cells MC-FA-010 and the control Microbody™ were biotinylated and preassembled on Cy3-conjugated streptavidin. In comparison to CHO-K1-MOCK, a specific binding of MC-FA-010-bio/SA-Cy3 was detected on CHO-K1-Seprase. As expected, the control Microbody™ does not bind to CHO-K1-Seprase cells (FIG. 6). This clearly demonstrates the specific interaction of MC-FA-010 to Seprase-expressing cells.

MC-FA-010 Specifically Binds to Seprase-expressing Tumors

To analyze binding of MC-FA-010 (tetramerized via Streptavidin-Cy3) to murine Seprase expressing tumor cells, BALB/c mice were injected subcutaneously with CT26 cells. Mice were sacrificed 14 days after tumor cell implantation and the tumor was isolated for paraffin sections. Afterwards, 3 µm sections were stained (FIG. 7). For visualization of the Seprase expressing CAFs (Cancer associated fibroblasts) sections were stained with anti-α-SMA antibody (green). The nuclei localization was stained with DAPI (blue). In red the specific binding of MC-FA-010 and the control Microbody™ MC-Myc-010 is detectable. Here we could show that MC-FA-010 binds on CAFs derived from murine tumor sections. As expected, the control Microbody™ does not bind to the CT26 tumor section. In summary it is possible to address Seprase-expressing tumors with the Seprase-specific Microbody™ MC-FA-010.

Oligomerization of MC-FA-010 Increases its Affinity

To study a possible avidity effect the binding activity of monovalent and tetravalent MC-FA-010 against human Seprase-overexpressing cells (CHO-K1-Seprase) was analyzed. Therefore, on the one hand monovalent Trx-MC-FA-010 fusion protein (consists of a Thioredoxin-His6-cassette) and on the other hand biotin-conjugated Microbody™ which was oligomerized using streptavidin-APC (MC-FA-010-bio/SA-APC) was used. Binding properties of the resulting MC-FA-010 constructs against human Seprase were determined by FACS and revealed a EC50 value of 177.6 nM of the monovalent MC-FA-010, while the tetravalent variant showed an even higher affinity with a EC50 of 2.367 nM (FIG. 8). Taken together oligomerization of MC-FA-010 leads to an avidity effect and increases the affinity of MC-FA-010 to Seprase.

Chemical Oligomerization of MC-FA-012

A DOTA conjugated trimerized version of the MC-FA-012 Microbody™ (DOTA-(MC-FA-012)$_3$) was purchased from Pepscan. The generation was based on an oxim ligation strategy. Therefore, a MC-FA-012 variant with an amino-terminal aminooxy group at the N-terminus was synthesized chemically. Besides, an anchor molecule was generated consisting of an amino-terminally attached DOTA moiety and three Lysine-Serine stretches separated by a GSGS linker sequence respectively. To form reactive aldehydes the terminal hydroxyl groups of the serine residues were oxidized with sodium-periodate. Finally, activated anchor and the aminooxy-MC-FA-012 variant were coupled in an oxim ligation reaction to form the DOTA-(MC-FA-012)$_3$ trimer (see FIG. 9 A).

The trimer was functionally analyzed in a FACS-based competition assay in comparison to the monomeric Microbody™ (see FIGS. 9 B and C). In this assay CHO-K1-huSeprase cells were consecutively stained with Trx-MC-FA-012 fusion protein and anti-H6-PE antibody. Parallel incubation with different concentrations of the trimer led to a significant inhibition with an IC50 value of 43.32 nM whereas only a slight competition could be seen with the monomer. Thus, the spatial orientation of the Microbodies™ on the trimeric scaffold enables efficient binding to the membrane bound seprase. The observed avidity effect indicates moreover that chemical oligomerization can be a productive way to increase the affinity of the ligand significantly and thereby facilitate enhanced binding and retention of the probe at the tumor site.

Beside the described DOTA conjugate DOTA-(MC-FA-012)$_3$ an AlexaFluor® 680 conjugated variant was purchased from Pepscan for in vivo imaging use. AlexaFluor680-(MC-FA-012)$_3$ (AF680-(MC-FA-012)$_3$) anchor molecule was generated analog to DOTA-(MC-FA-012)$_3$. Coupling of the AlexaFluor680 moiety was done as activated ester in solution to the N-terminal amid.

Kinetic Analysis of Monomeric MC-FA-010 and Monomeric and Trimeric MC-FA-012 Binding to Recombinant Human Seprase The binding kinetics of monomeric and trimeric Seprase-binding Microbodies was determined using surface plasmon resonance spectroscopy on a Biacore T-100 system. For the monomeric MC-FA-010 Microbody® a dissociation constant of 149 nM was measured. The MC-FA-012 variant with a single Lys2Ala exchange showed an affinity of 340 nM. Both trimeric variants DOTA-(MC-FA-012)$_3$ and AF680-(MC-FA-012)$_3$ showed a significantly higher affinity in sub-nanomolar range and slower offrate compared to the monomeric Microbodies. DOTA-(MC-FA-012)$_3$ has a dissociation constant of 12.4 µM (steady state analysis, 249 pM). AF680-(MC-FA-012)$_3$ has a dissociation constant of 61.5 pM (steady state analysis, 669 pM). Compared to MC-FA-012 the offrate of DOTA-(MC-FA-012)$_3$ is around 530, and of AF680-(MC-FA-012)$_3$ around 134 times slower. Due to the small size (~13000 Da) and slow offrate both trimeric constructs are predestined for in vivo imaging of tumors with a low overall background. Detailed kinetic data is summarized in table 3 and FIG. 11 (A-D).

Scaffold Swapping

In order to improve or to modulate the physicochemical properties of Microbody® binders and characteristics based on them (e.g. net charge, stability, oral availability) sequence branches responsible for binding can be grafted to other alternative scaffolds. In this study the binding sequence of MC-FA-012 mainly located in the first loop was transferred into two scaffolds based on Trypsin inhibitor EETI-II of *Ecballium elaterium* (ET-FA-012) and an optimized McoTI-II scaffold (*Momordica cochinchinensis*, MO-FA-012). Corresponding sequence information is listed in table 4. DNA coding regions of said proteins were cloned in the vector backbone of pET32b-LibEx enabling an expression as fusion to thioredoxin. Expression and purification was performed as described above (Example 1). For SPR analysis thioredoxin was separated through Thrombin cleavage and additional purification with IMAC and RP-HPLC. To confirm the correct synthesis expected mass was verified via mass spectroscopy. The functionality of the newly constructed Microbodies was analyzed using SPR. Both Microbodies showed specific binding to immobilized rhuSeprase with a slightly weaker dissociation constant compared to MC-FA-012 (table 3 and FIGS. 13 A and B). For ET-FA-012 a KD of 1.4 µM and for MO-FA-012 a KD of 1.34 µM was determined.

MC-FA-012 Specifically Binds to Seprase-expressing Triple Negative Breast Cancer (TNBC)

To analyze binding of MC-FA-012 to Seprase-expressing triple negative breast cancer, tumor sections were analyzed via immunofluorescence staining (FIG. 16). For visualization of cancer associated fibroblasts (CAFs) sections were stained with anti-α-SMA antibody (FIGS. 16 B and F). The nuclei were stained with DAPI (FIGS. 16 C and G) in parallel. Only the biotinylated MC-FA-012 Microbody® (tetramerized via Streptavidin-Cy3) (FIG. 16 A) but not the equally processed MC-FA-0116 variant (FIG. 16 E) shows a specific binding to the TNBC sections. The MC-FA-012/SA tetramer signal co-localizes to a high extend with SMA indicating the specific targeting of Seprase on CAFs (FIG. 16 D).

Example 4

Tumor Targeting in Seprase Expressing CHO-Xenograft with IRDye Conjungated MC-FA-012

To analyze biodistribution and tumor targeting properties of the MC-FA-012 Microbody™ a xenograft was established in immunodeficient mice Foxn1(nu) using the CHO-K1-huSeprase and CHO-K1-MOCK cell lines. The huSeprase ligand (MC-FA-012) and a control Microbody™ (MC-CM-010) were conjugated to IRDye800CW using NHS chemistry and injected i.v. into tumor bearing mice. After 0.5 and 2 h mice were euthanized. Organs were taken out and IR signal was measured ex vivo on a Xenogen IVIS optical in vivo imaging system (FIG. 10). In comparison to the negative control Microbody® the Seprase specific Microbody® MC-FA-012-IRDye800CW targeted the human Seprase-overexpressing tissue during a circulation period of 0.5 h. After 2 h MC-FA-012-IRDye800CW detached from the tumor with the result of no detectable tumor targeting. Thus the critical time period in tumor targeting with MC-FA-012 appears to occur during the first minutes after injection. Moreover a weaker binding of MC-FA-012-IRDye800CW on MOCK-tissue could also be observed. It cannot be excluded, that MOCK-tissue expresses murine Seprase, too. In summary, tumor targeting by the Seprase specific MC-FA-012-IRDye800CW Microbody® could be shown during the first few minutes after injection. On the basis of these data further in vivo evaluations should be conducted.

Biodistribution and Tumor Targeting Analysis

To analyze the pharmacokinetic and tumor targeting properties of the AF680-(MC-FA-012)$_3$ trimer biodistribution in female Fox n1 nu mice was monitored at six time points after injection (1, 2, 4, 6, 24 and 96 h). AF680-(MC-FA-0116)$_3$ and untreated mice served as controls. After each time point biodistibution was measured in vivo and ex vivo using a Xenogen Imaging system (FIG. 14 A+B). Throughout the analyzed time frame up to 24 h after injection a specific and significant tumor uptake of AF680-(MC-FA-012)$_3$ could be observed (FIG. 14, arrows and FIG. 15). In contrast the MC-FA-0116 control trimer did not accumulate in the tumor to a detectable extend (FIG. 14, and FIG. 15). Overall, the background signals for the binder and for the non-binding control were in the same range. While the signals in lung, heart, spleen and liver was generally low, strong kidney signals could be measured for both constructs after 1 hour which decreased however significantly after 2 hours.

Example 5

Further Characterization of the Binding Loop and Initial Attempts for Affinity Maturation In order to analyse the interaction between the MC-FA-012 Microbody® and seprase in greater detail and to identify more affine binders a focused library was generated on the basis of the alanine scan data and screened against soluble seprase. Therefore, four different selection conditions with varying stringency were applied. After three selection rounds all 4 pools were sub-cloned into an expression vector. 96 clones per pool were expressed and analysed with respect to expression rate as well as to target and unspecific binding properties. The s/n (signal to noise) value was calculated by division of the ELISA signal versus huSeprase and BSA and indicates for target specific binding. In addition to this s/n value a relative expression value (Ex) was calculated from SDS-PAGE data. Both values were taken into account for ranking of the clones. Ranking 1 and 2 values which differ with respect to weighting factors of the s/n value were calculated. The top-ranked clones of each pool (Pool 1: clones 1-4, Pool 2: 1-7, Pool 3: 1-4, Pool 4: 1-5 according to Ranking 2 values) or all clones with a ranking 2 value above 5 are shown in Tables 1 and 2 below.

TABLE 1

Top-ranked clones of each pool

>1
GACPYRNWMTGRGPLCRRDSDCPGRCICRGNGYCG

>2
GACMYMNWTPGRGPDCRRDSDCPGRCICRGNGYCG

>3
GACPYASWADGRGPHCRRDSDCPGRCICRGNGYCG

>4
GACVYQHWQPGRGPSCRRDSDCPGRCICRGNGYCG

>5
GACPYSRWAVGRGPSCRRDSDCPGRCICRGNGYCG

>6
GACPYTRWQPGRGPSCRRDSDCPGRCICRGNGYCG

>7
GACPYSNWAVGRGPSCRRDSDCPGRCICRGNGYCG

>8
GACPYSRWAVGRGPDCRRDSDCPGRCICRGNGYCG

>9
GACPYSNWAVGRGPSCRRDSDCPGRCICRGNGYCG

>10
GACPYTNWRPGRGPACRRDSDCPGRCICRGNGYCG

>11
GACPYSNWAVGRGPACRRDSDCPGRCICRGNGYCG

>12
GACAYSSWSAGRGPMCRRDSDCPGRCICRGNGYCG

>13
GACPYVNWAAGRGPVCRRDSDCPGRCICRGNGYCG

>14
GACPYAVWASGRGPSCRRDSDCPGRCICRGNGYCG

>15
GACEYSAWLAGRGPECRRDSDCPGRCICRGNGYCG

>16
GACVYWQWIAGRGPVCRRDSDCPGRCICRGNGYCG

>17
GACWYDPWWLGRGPVCRRDSDCPGRCICRGNGYCG

>18
GACMYDTWAQGRGPNCRRDSDCPGRCICRGNGYCG

TABLE 1-continued

Top-ranked clones of each pool

>19
GACLYEVWPLGRGPQCRRDSDCPGRCICRGNGYCG

>20
GACAYSNWQPGRGPHCRRDSDCPGRCICRGNGYCG

TABLE 2

Clones with a ranking 2 value above 5

>1
GACPYRNWMTGRGPLCRRDSDCPGRCICRGNGYCG

>2
GACMYMNWTPGRGPDCRRDSDCPGRCICRGNGYCG

>3
GACPYASWADGRGPHCRRDSDCPGRCICRGNGYCG

>4
GACVYQHWQPGRGPSCRRDSDCPGRCICRGNGYCG

>5
GACPYSRWAVGRGPSCRRDSDCPGRCICRGNGYCG

>6
GACPYTRWQPGRGPSCRRDSDCPGRCICRGNGYCG

>7
GACPYSNWAVGRGPSCRRDSDCPGRCICRGNGYCG

>8
GACPYSRWAVGRGPDCRRDSDCPGRCICRGNGYCG

>9
GACPYSNWAVGRGPSCRRDSDCPGRCICRGNGYCG

>10
GACPYTNWRPGRGPACRRDSDCPGRCICRGNGYCG

>11
GACPYSNWAVGRGPACRRDSDCPGRCICRGNGYCG

>12
GACPYSRWAVGRGPDCRRDSDCPGRCICRGNGYCG

>13
GACPYANWAVGRGPNCRRDSDCPGRCICRGNGYCG

>14
GACPYTYWHPGRGPGCRRDSDCPGRCICRGNGYCG

>15
GACPYSNWRPGRGPECRRDSDCPGRCICRGNGYCG

>16
GACPYANWMVGRGPSCRRDSDCPGRCICRGNGYCG

>17
GACPYTRWAVGRGPDCRRDSDCPGRCICRGNGYCG

>18
GACPYTRWAVGRGPDCRRDSDCPGRCICRGNGYCG

>19
GACPYARWAAGRGPACRRDSDCPGRCICRGNGYCG

>20
GACPYSTWQVGRGPSCRRDSDCPGRCICRGNGYCG

>21
GACPYTRWTVGRGPSCRRDSDCPGRCICRGNGYCG

TABLE 2-continued

Clones with a ranking 2 value above 5

>22
GACPYSRWAVGRGPDCRRDSDCPGRCICRGNGYCG

>23
GACPYTNWQPGRGPACRRDSDCPGRCICRGNGYCG

>24
GACPYTNWHPGRGPACRRDSDCPGRCICRGNGYCG

>25
GACPYTNWQPGRGPACRRDSDCPGRCICRGNGYCG

>26
GACPYTRWAVGRGPDCRRDSDCPGRCICRGNGYCG

>27
GACPYARWVVGRGPSCRRDSDCPGRCICRGNGYCG

>28
GACAYANWQVGRGPSCRRDSDCPGRCICRGNGYCG

>29
GACPYTRWAVGRGPDCRRDSDCPGRCICRGNGYCG

>30
GACPYARWVLGRGPDCRRDSDCPGRCICRGNGYCG

>31
GACPYTNWHPGRGPDCRRDSDCPGRCICRGNGYCG

>32
GACPYANWAVGRGPNCRRDSDCPGRCICRGNGYCG

>33
GACPYTYWHAGRGPSCRRDSDCPGRCICRGNGYCG

>34
GACPYSTWAVGRGPACRRDSDCPGRCICRGNGYCG

>35
GACPYTNWQPGRGPACRRDSDCPGRCICRGNGYCG

>36
GACPYTRWAVGRGPDCRRDSDCPGRCICRGNGYCG

>37
GACPYRNWAVGRGPSCRRDSDCPGRCICRGNGYCG

>38
GACPYATWQPGRGPSCRRDSDCPGRCICRGNGYCG

>39
GACPYTNWHPGRGPACRRDSDCPGRCICRGNGYCG

>40
GACPYTNWQPGRGPACRRDSDCPGRCICRGNGYCG

>41
GACPYARWNVGRGPSCRRDSDCPGRCICRGNGYCG

>42
GACPYTNWHPGRGPDCRRDSDCPGRCICRGNGYCG

>43
GACPYANWTIGRGPACRRDSDCPGRCICRGNGYCG

>44
GACPYARWHVGRGPSCRRDSDCPGRCICRGNGYCG

>45
GACAYSNWAVGRGPSCRRDSDCPGRCICRGNGYCG

>46
GACPYSTWAVGRGPDCRRDSDCPGRCICRGNGYCG

>47
GACPYTNWAVGRGPSCRRDSDCPGRCICRGNGYCG

TABLE 2-continued

Clones with a ranking 2 value above 5

>48
GACPYANWAVGRGPHCRRDSDCPGRCICRGNGYCG

>49
GACPYRNWQPGRGPTCRRDSDCPGRCICRGNGYCG

>50
GACPYSNWTVGRGPECRRDSDCPGRCICRGNGYCG

>51
GACPYHTWAVGRGPGCRRDSDCPGRCICRGNGYCG

>52
GACPYRNWSPGRGPHCRRDSDCPGRCICRGNGYCG

>53
GACPYTFWRVGRGPACRRDSDCPGRCICRGNGYCG

>54
GACPYSNWTVGRGPACRRDSDCPGRCICRGNGYCG

>55
GACPYSRWAVGRGPDCRRDSDCPGRCICRGNGYCG

>56
GACVYWQWIAGRGPVCRRDSDCPGRCICRGNGYCG

>57
GACWYDPWWLGRGPVCRRDSDCPGRCICRGNGYCG

>58
GACMYDTWAQGRGPNCRRDSDCPGRCICRGNGYCG

>59
GACLYEVWPLGRGPQCRRDSDCPGRCICRGNGYCG

>60
GACAYSNWQPGRGPHCRRDSDCPGRCICRGNGYCG

>61
GACEYHVWMGGRGPHCRRDSDCPGRCICRGNGYCG

A detailed characterization of the top-ranked clones especially concerning the kinetic parameters ($K_d$, $K_{on}$, $K_{off}$) in comparison to the parental MC-FA-012 variant is on-going.

Binding Analysis of MC-FA-012 Variants with Altered Binding Sequence

Seven selected clones of above mentioned ranking (Table 1 and 2, Example 5) had been further analyzed using SPR spectroscopy. The variants showed a dissociation constant in the same range (147-487 nM) as MC-FA-010 or MC-FA-012 (149-340 nM) with comparable offrate. Detailed kinetic data and sequence informations are summarized in table 3 and 4 and FIG. 12 (A-G). All seven variants showed binding to rhuSeprase confirming the identified binding motif CXYXXWXXGRGPXC.

Example 6

Biodistribution and Tumor Targeting Using $^{68}$Ga-(MC-FA-012)$_3$ and $^{177}$Lu-(MC-FA-012)$_3$ Organ distribution of $^{177}$Lu-(MC-FA-012)$_3$ Organ distribution of $^{177}$Lu-(MC-FA-012)$_3$ in CT26-huSeprase tumors bearing mice was monitored over 24 h. At six time points (0.5, 1, 2, 4, 6 and 24 h) mice were sacrificed and radioactivity in dissected organs had been measured. The measured dose is summarized in FIG. 17 and table 5 as percent of injected dose per gram [% ID/g]. The analyzed trimer showed specific tumor targeting with a high retention of radioactivity in the kidneys. However, the signal in kidney (286.8 to 213.4% ID/g) and tumor (9.9-5.9% ID/g) decreased over measured time period but could still be measured after 24 h.

Small Animal PET Imaging Using $^{68}$Ga-(MC-FA-012)$_3$

Biodistribution and tumor targeting of $^{68}$Ga-(MC-FA-012)$_3$ was measured during a time period of 140 minutes via PET scan. In both analyzed mice 68Ga-(MC-FA-012)$_3$ showed a specific tumor targeting (FIGS. 18-20), high tumor-to-background ratios already within the first 20 min and a high signal in the kidneys. This data confirms the results of the organ distribution study made with $^{177}$Lu-(MC-FA-012)$_3$.

Example 7

Diagnostic and Therapeutic Use of Microbody® Trimers

For diagnostic purpose 2.5 nmol $^{68}$Ga-(MC-FA-012)$_3$ was injected i.v. Up to date five patients with advanced pancreatic cancer had been examined. Detailed information on applied dose is summarized in table 6. $^{68}$Ga-(MC-FA-012)$_3$ showed high enrichment in primary tumors and metastasis (FIGS. 21-26 and table 11-16) and as already seen in small animal in vivo studies a high kidney uptake. Overall a low background in normal tissue could be observed. Possible nephroprotection e.g. in therapeutic application could be achieved by Arginine/Lysine, Gelofusine or fragmented albumin (FRALB) infusion or additional application of negative Microbody® MC-FA-0116 or the trimeric variant (MC-FA-0116)$_3$.

For therapeutic purpose 10-15 nmol $^{177}$Lu-(MC-FA-012)$_3$ was injected i.v. (table 7). Two patients had been recently treated. The patients showed no acute nephrotoxicity. The treatment is still on going.

Example 8

Immunohistochemical Analysis of Seprase Expression in Different Tumor Entities

To provide insights in Seprase expression in different tumor entities an immunohistochemical analysis had been performed.

Pancreas Carcinoma

Seprase expression in normal pancreas tissue is limited to langerhans islets, ducts and vessels. On pancreas carcinoma Seprase expression is additionally detected on tumor cells and fibroblasts (Table 8 and FIG. 27). On 17/17 pancreas carcinoma samples 10-85% tumor cells weak to strong cytoplasmic/membranous staining is detected. On 12/17 tissues 5% normal cells (islets of Langerhans and ducts) weak to strong cytoplasmic/membranous staining is detected. On 10/17 tissues 60-75% vessels weak to medium membranous staining is detected. On 11/17 tissues 2-50% fibrous tissue (fibroblasts) weak to strong cytoplasmic/membranous staining is detected. Taken together data of the present study suggest Seprase to be overexpressed in fibroblasts of human pancreatic tumor stroma compared to normal tissue (fibroblast staining in only one case, staining on langerhans islets, ducts and vessels).

Triple Negative Breast Cancer (TNBC)

On 39/39 TNBCs samples many weak till strong membranous and cytoplasmic stained fibroblasts (~54%) were detected within fibrous tissue (sometimes with stronger signals around tumor cells). In one case signals on necrosis/pre-necrotic cells were found. On 3/3 normal human breast samples some medium stained fibroblasts (~3%) were detected within fibrous tissue (Table 9 and FIG. 28). Staining on normal tissue can be due to adjacent localization to pathological tissue. Taken together data of the present study suggest Seprase to be overexpressed in fibroblasts of human TNBC tumor stroma compared to normal tissue (weak expression).

Lung Carcinoma

On 29/31 lung carcinomas many weak till strong membranous and cytoplasmic stained fibroblasts (~55%) were detected within fibrous tissue. In five cases signals on necrosis/pre-necrotic cells were found. On 2/3 normal human lung samples some weak till strong stained fibroblasts (~17%) were detected within fibrous tissue (Table 10 and FIG. 29). Staining on normal tissue can be due to adjacent localization to pathological tissue. Taken together data of the present study suggest Seprase to be overexpressed in fibroblasts of human lung tumor stroma compared to normal tissue (weak expression).

Seprase seems to be an overexpressed target in pancreas cancer, TNBC and lung carcinoma. Therefore, the use of the identified Seprase ligand as diagnostic and therapeutic agent is not limited to the described clinical application.

TABLE 3

Affinity determination of monomeric and trimeric Seprase binding Microbodies

| Analyte | ka (1/Ms) | kd (1/s) | KD (M) | Chi$^2$ (RU$^2$) | KD (M, steady state) | Chi$^2$ (RU$^2$) | FIG. |
|---|---|---|---|---|---|---|---|
| MC-FA-010 | 1.53E+06 | 0.2006 | 1.49E−07 | 0.131 | 1.06E−07 | 0.21 | 11A |
| MC-FA-012 | 4.08E+05 | 0.1385 | 3.40E−07 | 0.041 | 2.46E−07 | 0.0416 | 11B |
| *DOTA-(MC-FA-012)$_3$* | *2.11E+07* | *2,61E-04* | *1.24E−11* | *0.446* | *2.49E−10* | *14.6* | *11C* |
| *AF680-(MC-FA-012)$_3$* | *1.68E+07* | *0,001031* | *6.15E−11* | *0.874* | *6.69E−10* | *9.11* | *11D* |
| FA8-D06 | 3.46E+05 | 0.05303 | 1.53E−07 | 1.2 | 1.13E−07 | 1.42 | 12A |
| FA7-A05 | 2.46E+05 | 0.05035 | 2.05E−07 | 1.09 | 1.02E−07 | 1.11 | 12B |
| FA8-C09 | 9.92E+06 | 2.935 | 2.96E−07 | 0.328 | 2.43E−07 | 9.5 | 12C |
| FA8-D03 | 9.39E+05 | 0.1381 | 1.47E−07 | 0.824 | 1.51E−07 | 0.137 | 12D |
| FA8-D05 | 4.21E+06 | 0.8121 | 1.93E−07 | 0.441 | 1.77E−07 | 0.822 | 12E |
| FA8-F04 | 6.24E+05 | 0.2003 | 3.21E−07 | 0.218 | 3.32E−07 | 0.21 | 12F |
| FA8-G12 | 6.51E+05 | 0.3171 | 4.87E−07 | 0.146 | 4.70E−07 | 0.0436 | 12G |
| ET-FA-012 | 6.08E+05 | 0.8528 | 1.40E−06 | 0.271 | 4.54E−06 | 0.488 | 13A |
| MO-FA-012 | 3.82E+05 | 0.5128 | 1.34E−06 | 1.43 | 1.16E−06 | 0.561 | 13B |

Offrate highlighted in bold letters, trimeric constructs are highlighted in italic letters

TABLE 4

Sequence listing

| Microbody ® | Amino acid Sequence |
|---|---|
| ET-FA-012 | GSGACPYSNWTPGRGPDCSQDSDCLAGCVCGPNGFCG |
| MO-FA-012 | GSGACPYSNWTPGRGPDCSSDSDCPGACICLENGFCG |
| FA7-A05 | GSGACPYSRWMPGRGPSCRRDSDCPGRCICRGNGYCG |
| FA8-C09 | GSGACPYTNWRPGRGPACRRDSDCPGRCICRGNGYCG |
| FA8-D03 | GSGACPYTRWAVGRGPDCRRDSDCPGRCICRGNGYCG |
| FA8-D05 | GSGACPYTRWQPGRGPSCRRDSDCPGRCICRGNGYCG |
| FA8-D06 | GSGACPYSRWAVGRGPDCRRDSDCPGRCICRGNGYCG |
| FA8-F04 | GSGACPYSNWAVGRGPSCRRDSDCPGRCICRGNGYCG |
| FA8-G12 | GSGACPYTNWHPGRGPACRRDSDCPGRCICRGNGYCG |

TABLE 5

Organ distribution of $^{177}$Lu-(MC-FA-012)$_3$
Mean % ID/g (n = 3)

| | 30 min | 1 h | 2 h | 4 h | 6 h | 24 h |
|---|---|---|---|---|---|---|
| Blood | 1.3512 | 0.3597 | 0.1353 | 0.042 | 0.0374 | 0.0429 |
| Heart | 0.6152 | 0.1869 | 0.1284 | 0.1015 | 0.0876 | 0.0641 |
| Lungs | 1.7729 | 0.6705 | 0.6067 | 0.4514 | 0.6476 | 0.189 |
| Liver | 0.6684 | 0.3983 | 0.4402 | 0.4101 | 0.431 | 0.3631 |
| Spleen | 0.9253 | 0.5493 | 0.6561 | 0.5931 | 0.6287 | 0.4561 |
| Kidneys | 286.7812 | 222.3177 | 272.3888 | 245.1877 | 259.4467 | 213.4107 |
| Intestine | 0.7435 | 0.5079 | 1.0902 | 0.2913 | 0.9309 | 0.3347 |
| Brain | 0.6895 | 0.2284 | 0.5818 | 0.3159 | 0.2159 | 0.2151 |
| Muscle | 0.0589 | 0.0423 | 0.0317 | 0.0241 | 0.1259 | 0.0253 |
| Tumor | 9.8546 | 6.7929 | 8.1504 | 7.7667 | 7.8057 | 5.8505 |
| Injection site | 4.2434 | 15.2418 | 2.8704 | 2.6095 | 1.5742 | 0.9827 |

TABLE 6

$^{68}$Ga-labeling of DOTA-(MC-FA-012)$_3$ for diagnostic purposes
$^{68}$Ga-(MC-FA-012)$_3$

| Patient | Date | MBq (administered) | nmol | $t_R$ (HPLC) | Surgery |
|---|---|---|---|---|---|
| 1 | 29.10.15 | 359 | 2.5 | 2.22 | No |
| 2 | 02.11.15 | 351 | 2.5 | 2.22 | Pancreatectomy (Whipple, part.) |
| 3 | 24.11.15 | 63 | 2.5 | 2.24 | No |
| 4 | 14.01.16 | 166 | 2.5 | 2.20 | Pancreatectomy/ splenectomy (part.) |
| 5 | 02.02.16 | 355 | 2.5 | 2.21 | No |

TABLE 7

$^{177}$Lu-labeling of DOTA-(MC-FA-012)$_3$ for therapeutic purposes
$^{177}$Lu-(MC-FA-012)$_3$

| Patient | Date | GBq (product) | nmol | $t_R$ (HPLC) |
|---|---|---|---|---|
| 3 | 20.01.16 | 2.318 | 15 | 2.04 |
| 5 | 04.02.16 | 2.530 | 10 | 2.06 |

TABLE 8

IHC study of Seprase expression in pancreatic cancer

| Tissue | Tissue ID | 1° Antibody | % pos. tumor cells 0 | +1 | +2 | +3 | Subcellular pattern | Normal epithelial cells | % pos. | Fibrous tissue |
|---|---|---|---|---|---|---|---|---|---|---|
| Pancreas | BT002857A_1F_1PEB | Anti-Seprase | X | X | X | X | X | ++ | 5 | − |
| Pancreas | BT002849A_1F_1PEB | Anti-Seprase | X | X | X | X | X | ++ | 5 | − |
| Pancreas | BT002850A_1F_1PEB | Anti-Seprase | X | X | X | X | X | ++ | 5 | − |
| Pancreas | BT002852A_1F_1PEB | Anti-Seprase | X | X | X | X | X | + | 55 | + |
| Pancreas | BT002852A_1F_1PEB | Anti-Seprase | X | X | X | X | X | + | 55 | + |
| Pancreas | BT002853A_1F_1PEB | Anti-Seprase | X | X | X | X | X | ++ | 5 | − |
| Pancreas | BT002854A_1F_1PEB | Anti-Seprase | X | X | X | X | X | ++ | 5 | − |
| Pancreas | BT002856A_1F_1PEB | Anti-Seprase | X | X | X | X | X | + | 45 | − |
| Pancreas | BT002858A_1F_1PEB | Anti-Seprase | X | X | X | X | X | + | 60 | − |
| Pancreas | BT002859A_1F_1PEB | Anti-Seprase | X | X | X | X | X | + | 60 | − |
| Pancreas | BT002873A_1F_1PEB | Anti-Seprase | X | X | X | X | X | + | 45 | − |
| Pancreas | BT002874A_1F_1PEB | Anti-Seprase | X | X | X | X | X | + | 35 | − |
| Pancreas | BT002875A_1F_1PEB | Anti-Seprase | X | X | X | X | X | + | 30 | − |
| Pancreas | BT002876A_1F_1PEB | Anti-Seprase | X | X | X | X | X | + | 20 | − |
| Pancreas | BT002877A_1F_1PEB | Anti-Seprase | X | X | X | X | X | + | 30 | − |
| Pancreas | Pancreas 4 | Anti-Seprase | X | X | X | X | X | + | 30 | − |
| Pancreas | Pancreas 2 | Anti-Seprase | X | X | X | X | X | ++ | 10 | − |
| Colon | Colon 2 | Anti-Seprase | X | X | X | X | X | + | 20 | − |
| Pancreas_CA | BT002813A_1F_1PEB | Anti-Seprase | 30 | 70 | 0 | 0 | c/m | + | 5 | ++ |
| Pancreas_CA | BT002829A_1F_1PEB | Anti-Seprase | 50 | 40 | 10 | 0 | c/m | X | X | + |
| Pancreas_CA | BT002830A_1F_1PEB | Anti-Seprase | 20 | 60 | 20 | 0 | c/m | ++ | 5 | ++ |
| Pancreas_CA | BT002831A_1F_1PEB | Anti-Seprase | 20 | 20 | 50 | 10 | c/m | + | 5 | ++ |
| Pancreas_CA | BT002845A_1F_1PEB | Anti-Seprase | 30 | 50 | 20 | 0 | c/m | + | 5 | ++ |
| Pancreas_CA | BT002846A_1F_1PEB | Anti-Seprase | 20 | 70 | 10 | 0 | c/m | − | 0 | − |
| Pancreas_CA | BT002847A_1F_1PEB | Anti-Seprase | 30 | 70 | 0 | 0 | c/m | + | 5 | − |
| Pancreas_CA | BT002848A_1F_1PEB | Anti-Seprase | 90 | 8 | 2 | 0 | c | − | 0 | − |
| Pancreas_CA | BT002860A_1F_1PEB | Anti-Seprase | 15 | 70 | 15 | 0 | c/m | − | 0 | +++ |
| Pancreas_CA | BT002861A_1F_1PEB | Anti-Seprase | 30 | 50 | 20 | 0 | c/m | X | X | ++ |
| Pancreas_CA | BT002868A_1F_1PEB | Anti-Seprase | 90 | 8 | 2 | 0 | c/m | + | 5 | + |
| Pancreas_CA | BT002869A_1F_1PEB | Anti-Seprase | 20 | 20 | 60 | 0 | c/m | ++ | 5 | + |
| Pancreas_CA | BT002870A_1F_1PEB | Anti-Seprase | 35 | 25 | 40 | 0 | c/m | ++ | 5 | − |
| Pancreas_CA | BT002871A_1F_1PEB | Anti-Seprase | 20 | 55 | 25 | 0 | c/m | ++ | 5 | + |
| Pancreas_CA | BT002872A_1F_1PEB | Anti-Seprase | 25 | 45 | 30 | 0 | c/m | ++ | 5 | + |
| Pancreas_CA | 15B02208 | Anti-Seprase | 30 | 30 | 20 | 20 | c/m | ++ | 5 | − |
| Pancreas_CA | 12B15338.1 | Anti-Seprase | 90 | 1 | 0 | 9 | c/m | ++ | 5 | − |
| Pancreas_CA | 12B15338.2 | Anti-Seprase | 90 | 3 | 0 | 8 | c/m | ++ | 5 | − |
| CHO-K1-huSeprase | 15_503 | Anti-Seprase | 15 | 40 | 30 | 15 | m | − | 0 | − |
| CHO-K1-huSeprase | 15_503 | Anti-Seprase | 15 | 30 | 35 | 20 | m | − | 0 | − |
| CHO-K1-huSeprase | 15_503 | Anti-Seprase | 15 | 35 | 35 | 15 | m | − | 0 | − |

| Tissue | % pos. | Vessels | % pos. | Necrosis | % necrotic area | Comment |
|---|---|---|---|---|---|---|
| Pancreas | 0 | + | 75 | X | X | +/++/+++ c langerhans islets, +/++ m vessels and ducts |
| Pancreas | 0 | + | 65 | − | 85 | +/++/+++ c (prenecrotic) langerhans islets, +/++ m vessels and ducts |
| Pancreas | 0 | + | 70 | − | 75 | +/++/+++ c (prenecrotic) langerhans islets, +/++ m vessels and ducts |
| Pancreas | 60 | ++ | 80 | X | X | +/++/+++ c langerhans islets, +/++/+++ c/m fibroblasts, +/++/+++ m vessels and ducts |
| Pancreas | 60 | ++ | 80 | X | X | +/++/+++ c langerhans islets, +/++/+++ c/m fibroblasts, +/++/+++ m vessels and ducts |
| Pancreas | 0 | + | 80 | X | X | +/++/+++ c langerhans islets, +/++ m vessels and ducts; BG secretion |
| Pancreas | 0 | + | 75 | X | X | +/++/+++ c langerhans islets, +/++ m vessels and ducts; BG secretion |
| Pancreas | 0 | + | 60 | X | X | +/++/+++ c langerhans islets, +/++ m vessels and ducts |
| Pancreas | 0 | ++ | 75 | X | X | +/++/+++ c langerhans islets, +/++/+++ m vessels and ducts |
| Pancreas | 0 | + | 65 | X | X | +/++ c langerhans islets, +/++ m vessels and ducts |
| Pancreas | 0 | ++ | 75 | X | X | +/++/+++ c langerhans islets, +/++/+++ m vessels and ducts |
| Pancreas | 0 | + | 70 | X | X | +/++/+++ c langerhans islets, +/++ m vessels and ducts |
| Pancreas | 0 | ++ | 75 | X | X | +/++/+++ c langerhans islets, +/++ m vessels and ducts |
| Pancreas | 0 | + | 70 | X | X | +/++/+++ c langerhans islets, +/++ m vessels and ducts |
| Pancreas | 0 | + | 70 | X | X | +/++/+++ c langerhans islets, +/++ m vessels and ducts |
| Pancreas | 0 | ++ | 65 | X | X | +/++/+++ c langerhans islets, +/++ m vessels and ducts |
| Pancreas | 0 | ++ | 65 | X | X | +/++/+++ c langerhans islets, +/++ m vessels and ducts |
| Colon | 0 | − | 0 | X | X | BG mucosa |
| Pancreas_CA | 10 | + | 65 | X | X | +/++/+++ c/m langerhans islets, +/++/+++ c/m fibroblasts, +/++ m vessels and ducts |
| Pancreas_CA | 5 | + | 60 | X | X | +/++ c/m fibroblasts, + m vessels, +/++ c/m mucosa (intestine); BG muscle |

TABLE 8-continued

IHC study of Seprase expression in pancreatic cancer

| | | | | | | |
|---|---|---|---|---|---|---|
| Pancreas_CA | 20 | ++ | 75 | X | X | +/++/+++ c/m langerhans islets, +/++/+++ fibroblasts, +/++/+++ vessels and ducts; BG secretion |
| Pancreas_CA | 2 | + | 65 | X | X | +/++/+++ c/m langerhans islets, +/++/+++ fibroblasts, +/++ vessels and ducts |
| Pancreas_CA | 30 | ++ | 75 | X | X | +/++/+++ fibroblasts, +/++ vessels and ducts |
| Pancreas_CA | 0 | − | 0 | − | 5 | −/+/++ c/m mucosa (intestine) |
| Pancreas_CA | 0 | + | 65 | − | 5 | +/++/+++ c/m langerhans islets, +/++/+++ fibroblasts, +/++ vessels and ducts; BG secretion |
| Pancreas_CA | 0 | − | 0 | − | 35 | X |
| Pancreas_CA | 50 | ++ | 75 | − | 15 | +/++/+++ c/m fibroblasts, +/++ m vessels, +/++/+++ m prenecrotic cells |
| Pancreas_CA | 45 | + | 65 | X | X | +/++/+++ c/m fibroblasts, +/++ m vessels |
| Pancreas_CA | 2 | − | 0 | − | 25 | +/++ c/m langerhans islets, +/++ fibroblasts |
| Pancreas_CA | 20 | − | 0 | X | X | +/++/+++ c langerhans islets, +/++/+++ c/m fibroblasts |
| Pancreas_CA | 0 | − | 0 | X | X | +/++/+++ c langerhans islets |
| Pancreas_CA | 15 | − | 0 | X | X | +/++/+++ c langerhans islets, +/++ c/m fibroblasts |
| Pancreas_CA | 5 | + | 65 | X | X | +/++/+++ c/m langerhans islets, + fibroblasts, + /++ vessels |
| Pancreas_CA | 0 | + | 75 | X | X | +/++/+++ c/m langerhans islets, +/++ vessels and ducts; BG muscle |
| Pancreas_CA | 0 | − | 0 | X | X | +/++/+++ c/m langerhans islets |
| Pancreas_CA | 0 | − | 0 | X | X | +/++/+++ c/m langerhans islets |
| CHO-K1-huSeprase | 0 | − | 0 | ++ | 50 | BG necrosis; small stained dots |
| CHO-K1-huSeprase | 0 | − | 0 | ++ | 50 | BG necrosis; small stained dots |
| CHO-K1-huSeprase | 0 | − | 0 | ++ | 50 | BG necrosis; small stained dots |

TABLE 9

IHC study of Seprase expression In triple negative breast cancer.

| Tumor/normal | Tissue | Tissue ID | antibody | Fibrous tissue | % pos. | Necrosis | % pos. | comment |
|---|---|---|---|---|---|---|---|---|
| Tumor | Breast | IN000422A_T_121FFEB | anti-Seprase | ++ | 70 | − | 0 | +/++ m/c fibroblasts |
| Tumor | Breast | IN000423A_T_122FEB | anti-Seprase | ++ | 75 | − | 10 | +/+++/+++ m/c fibroblasts |
| Tumor | Breast | IN000424A_T_123FEB | anti-Seprase | + | 80 | − | 20 | +/++ m/c fibroblasts |
| Tumor | Breast | IN000425A_T_124FEB | anti-Seprase | ++ | 40 | − | 0 | +/++/m/c fibroblasts |
| Tumor | Breast | IN000426A_T_125FEB | anti-Seprase | ++ | 30 | − | 10 | +/++ m/c fibroblasts, tissue partly disrupted and not analyzable |
| Tumor | Breast | IN000428A_T_127FEB | anti-Seprase | ++ | 70 | − | 5 | +/+++/+++ m/c fibroblasts |
| Tumor | Breast | IN000430A_T_129FEB | anti-Seprase | ++ | 35 | − | 0 | +/++ m/c fibroblasts |
| Tumor | Breast | IN000431A_T_130FEB | anti-Seprase | ++ | 40 | − | 0 | +/++ m/c fibroblasts |
| Tumor | Breast | IN000432A_T_131FEB | anti-Seprase | ++ | 60 | − | 0 | +/+++/+++ m/c fibroblasts |
| Tumor | Breast | IN000389A_T_88FFB | anti-Seprase | ++ | 90 | +++ | 10 | ++ m/c fibroblasts, ++/+++ necrosis, stained dots within necrosis |
| Tumor | Breast | IN00407A_T_106FFB | anti-Seprase | ++ | 60 | − | 5 | +/++ m/c fibroblasts |
| Tumor | Breast | IN000383A_T_82FFB | anti-Seprase | ++ | 80 | − | 10 | +/++ m/c fibroblasts |
| Tumor | Breast | IN000384A_T_83FFB | anti-Seprase | ++ | 90 | − | 0 | +/++ m/c fibroblasts, tissue partly missing and not analyzable |
| Tumor | Breast | IN000385A_T_84FFB | anti-Seprase | ++ | 65 | − | 0 | +/++ m/c fibroblasts, tissue partly disrupted and not analyzable |
| Tumor | Breast | IN000386A_T_85FFB | anti-Seprase | + | 30 | − | 20 | +/+++ m/c fibroblasts, tissue partly disrupted and not analyzable |
| Tumor | Breast | IN000387A_T_86FFB | anti-Seprase | ++ | 45 | − | 0 | +/++ m/c fibroblasts, tissue partly missing and not analyzable |
| Tumor | Breast | IN000388A_T_87FFB | anti-Seprase | + | 10 | − | 0 | + m/c fibroblasts |
| Tumor | Breast | IN000389A_T_88FFB | anti-Seprase | ++ | 90 | +++ | 10 | ++ m/c fibroblasts, ++/+++ necrosis, stained dots within necrosis |
| Tumor | Breast | IN000390A_T_89FFB | anti-Seprase | ++ | 85 | − | 0 | +/++ m/c fibroblasts |
| Tumor | Breast | IN000391A_T_90FFB | anti-Seprase | + | 40 | − | 0 | + m/c fibroblasts, ++/+++ fibroblasts around tumor cells, tissue partly not analyzable |
| Tumor | Breast | IN000392A_T_91FFB | anti-Seprase | ++ | 45 | − | 0 | +/++ m/c fibroblasts |
| Tumor | Breast | IN000393A_T_92FFB | anti-Seprase | + | 90 | − | 5 | +/++ m/c fibroblasts, tissue partly missing and not analyzable |
| Tumor | Breast | IN000394A_T_93FFB | anti-Seprase | ++ | 50 | − | 0 | +/++ m/c fibroblasts, tissue partly disrupted and not analyzable |
| Tumor | Breast | IN000399A_T_98FFB | anti-Seprase | ++ | 95 | − | 1 | +/++ m/c fibroblasts, ++/+++ fibroblasts around tumor cells, tissue partly disrupted and not analyzable |
| Tumor | Breast | IN000401A_T_100FFB | anti-Seprase | ++ | 35 | − | 0 | +/++ m/c fibroblasts |
| Tumor | Breast | IN000403A_T_102FFB | anti-Seprase | + | 90 | − | 0 | +/++ m/c fibroblasts, tissue partly disrupted and not analyzable |
| Tumor | Breast | IN000404A_T_103FFB | anti-Seprase | + | 1 | − | 0 | Rarely + m/c fibroblasts, tissue partly disrupted and not analyzable |
| Tumor | Breast | IN000405A_T_104FFB | anti-Seprase | +++ | 90 | − | 25 | +/++ m/c fibroblasts |
| Tumor | Breast | IN000406A_T_105FFB | anti-Seprase | + | 40 | − | 70 | +/++ m/c fibroblasts |
| Tumor | Breast | IN000407A_T_106FFB | anti-Seprase | ++ | 60 | − | 5 | +/++ m/c fibroblasts |
| Tumor | Breast | IN000408A_T_107FFB | anti-Seprase | ++ | 50 | − | 10 | +/++ m/c fibroblasts |
| Tumor | Breast | IN000409A_T_108FFB | anti-Seprase | + | 30 | − | 0 | +/++ m/c fibroblasts |
| Tumor | Breast | IN000410A_T_109FFB | anti-Seprase | ++ | 90 | − | 5 | +/++ m/c fibroblasts |
| Tumor | Breast | IN000411A_T_110FFB | anti-Seprase | ++ | 20 | − | 0 | +/++ m/c fibroblasts |
| Tumor | Breast | IN000412A_T_111FFB | anti-Seprase | ++ | 35 | − | 0 | +/++ m/c fibroblasts, tissue partly disrupted or missing and not analyzable |
| Tumor | Breast | IN000413A_T_112FFB | anti-Seprase | + | 20 | − | 10 | + m/c fibroblasts |
| Tumor | Breast | IN000414A_T_113FFB | anti-Seprase | ++ | 35 | − | 0 | +/+++/+++ m/c fibroblasts |
| Tumor | Breast | IN000415A_T_114FFB | anti-Seprase | ++ | 50 | − | 0 | +/++ m/c fibroblasts |
| Tumor | Breast | IN000416A_T_115FFB | anti-Seprase | ++ | 80 | − | 15 | +/++ m/c fibroblasts |
| Tumor | Breast | IN000420A_T_119FFB | anti-Seprase | ++ | 30 | − | 0 | +/++ m/c fibroblasts |
| Tumor | Breast | IN000421A_T_120FFB | anti-Seprase | ++ | 40 | − | 0 | +/++ m/c fibroblasts, tissue partly disrupted and not analyzable |
| Tumor | Breast | IN000389A_T_88FFB | 2° Ab only | − | 0 | X | X | 2° AB only control |
| Tumor | Breast | IN000407A_T_106FFB | 2° Ab only | − | 0 | X | X | 2° AB only control |
| Normal | Breast | 3947 | anti-Seprase | ++ | 1 | − | X | ++ fibroblasts, unspecific signals on secretion |

TABLE 9-continued

IHC study of Seprase expression In triple negative breast cancer.

| Tumor/normal | Tissue | Tissue ID | antibody | Fibrous tissue | % pos. | Necrosis | % pos. | comment |
|---|---|---|---|---|---|---|---|---|
| Normal | Breast | 3008 | anti-Seprase | ++ | 1 | X | X | ++ fibroblasts, unspecific signal and secretion |
| Normal | Breast | 2587 | anti-Seprase | ++ | 10 | X | X | ++ fibroblasts, unspecific signal |
| Normal | Breast | IN00804A_N_7FFB | anti-Seprase | ++ | 1 | X | X | ++ fibroblasts, unspecific signals on secretion |
| Normal | Breast | IN00805_N_8FFB | anti-Seprase | ++ | 0 | X | X | ++ fibroblasts |
| Normal | Breast | 3008 | 2° Ab only | − | 0 | X | X | 2° AB only control |
| Normal | Breast | 2587 | 2° Ab only | − | 0 | X | X | 2° AB only control |

TABLE 10

IHC study of Seprase expression in lung cancer.

| Tumor/normal | Tissue | Tissue ID | antibody | Fibrous tissue | % pos. | Necrosis | % pos. | comment |
|---|---|---|---|---|---|---|---|---|
| Tumor | Lung | 810 | anti-Seprase | +++ | 30 | − | 5 | ++/+++ m/c fibroblasts around tumor cells |
| Tumor | Lung | 816 | anti-Seprase | ++ | 75 | − | 0 | +/+++ m/c fibroblasts, tissue partly disrupted and not analyzable |
| Tumor | Lung | 820 | anti-Seprase | ++ | 90 | − | 0 | +/+++ m/c fibroblasts |
| Tumor | Lung | 828 | anti-Seprase | + | 60 | − | 0 | +/+++ m/c fibroblasts |
| Tumor | Lung | 1021 | anti-Seprase | ++ | 90 | − | 0 | +/+++ m/c fibroblasts, tissue partly disrupted and not analyzable |
| Tumor | Lung | 1023 | anti-Seprase | ++ | 45 | − | 30 | +/+++ m/c fibroblasts, tissue partly folded and not analyzable |
| Tumor | Lung | 1025 | anti-Seprase | + | 20 | − | 0 | +/+++ m/c fibroblasts, tissue partly disrupted and not analyzable |
| Tumor | Lung | 1027 | anti-Seprase | ++ | 75 | − | 50 | +/+++ m/c fibroblasts |
| Tumor | Lung | 1031 | anti-Seprase | ++ | 80 | − | 40 | +/++/+++ m/c fibroblasts |
| Tumor | Lung | 1041 | anti-Seprase | ++ | 90 | − | 0 | +/+++ m/c fibroblasts, tissue partly disrupted and not analyzable |
| Tumor | Lung | 1047 | anti-Seprase | + | 60 | − | 0 | +/+++ m/c fibroblasts, tissue partly disrupted and not analyzable |
| Tumor | Lung | 1049 | anti-Seprase | ++ | 90 | − | 0 | +/+++ m/c fibroblasts, tissue partly disrupted and not analyzable |
| Tumor | Lung | 1051 | anti-Seprase | ++ | 75 | − | 0 | ++/+++ m/c fibroblasts, tissue partly disrupted and not analyzable |
| Tumor | Lung | 1061 | anti-Seprase | + | 10 | − | 0 | +/+++ m/c fibroblasts |
| Tumor | Lung | 1082 | anti-Seprase | ++ | 60 | − | 45 | +/+++ m/c fibroblasts |
| Tumor | Lung | 1296 | anti-Seprase | ++ | 95 | − | 0 | +/+++ m/c fibroblasts |
| Tumor | Lung | 1299 | anti-Seprase | + | 5 | − | 5 | +/+++ m/c fibroblasts |
| Tumor | Lung | 1301 | anti-Seprase | ++ | 5 | − | 0 | +/+++ m/c fibroblasts |
| Tumor | Lung | 1304 | anti-Seprase | + | 20 | − | 35 | +/+++ m/c fibroblasts |
| Tumor | Lung | 1307 | anti-Seprase | ++ | 95 | − | 0 | +/+++ m/c fibroblasts |
| Tumor | Lung | 1308 | anti-Seprase | ++ | 40 | − | 5 | +/+++ m/c fibroblasts |
| Tumor | Lung | 1309 | anti-Seprase | ++ | 35 | − | 5 | +/+++ m/c fibroblasts, tissue partly disrupted and not analyzable |
| Tumor | Lung | 1310 | anti-Seprase | + | 95 | − | 25 | +/+++ m/c fibroblasts |
| Tumor | Lung | 1314 | anti-Seprase | ++ | 85 | − | 0 | +/+++ m/c fibroblasts |
| Tumor | Lung | 2164 | anti-Seprase | ++ | 80 | +++ | 15 | +/+++ m/c fibroblasts, ++/+++ necrosis, stained cells within necrosis |
| Tumor | Lung | 2167 | anti-Seprase | ++ | 70 | +++ | 10 | +/+++ m/c fibroblasts, ++/+++ necrosis, stained cells within necrosis |
| Tumor | Lung | 2168 | anti-Seprase | ++ | 65 | +++ | 5 | +/+++ m/c fibroblasts, ++/+++ necrosis, stained cells within necrosis, tissue partly disrupted and not analyzable |
| Tumor | Lung | 2172 | anti-Seprase | + | 10 | +++ | 5 | +/+++ m/c fibroblasts, ++/+++ necrosis, stained cells within necrosis |
| Tumor | Lung | 2174 | anti-Seprase | ++ | 65 | +++ | 20 | +/+++ m/c fibroblasts, ++/+++ necrosis, stained cells within necrosis |
| Tumor | Lung | 2164 | 2° Ab only | − | 0 | X | X | 2° AB control |
| Tumor | Lung | 1307 | 2° Ab only | − | 0 | X | X | 2° AB control |
| Normal | Lung | 569 | Anti-Seprase | − | 0 | X | X | No staining detectable |
| Normal | Lung | 575 | Anti-Seprase | ++ | 40 | X | X | +/++/+++ m/c fibroblasts, tissue partly disrupted and not analyzable |
| Normal | Lung | 581 | Anti-Seprase | + | 2 | X | X | + m/c fibroblasts |
| Normal | Lung | 575 | 2° Ab only | − | 0 | X | X | 2° AB control |

TABLE 11

Quantification of PET-data: Organ distribution of $^{68}$Ga-(MC-FA-012)$_3$ 1 and 3 hours after administration (SUV max/SUV mean) in patient 1 (rt = right, lft = left).

|  | 1 h | | 3 h | |
|---|---|---|---|---|
| Organs | SUV max | SUV mean | SUV max | SUV mean |
| Brain | 0.36 | 0.06 | 0.37 | 0.19 |
| Pancreas tail (tumor) | 7.61 | 4.54 | 10.37 | 5.04 |
| Pancreas head (tumor) | 8.85 | 4.77 | 9.78 | 5.1 |
| Lungs | 0.78 | 0.41 | 0.81 | 0.45 |
| Liver | 6.29 | 4.51 | 8.41 | 4.18 |
| Spleen | 3.04 | 2.18 | 2.97 | 1.17 |
| Intestine ROI1 | 1.58 | 0.76 | 1.55 | 0.57 |
| Intestine ROI2 | 1.95 | 1.12 | 1.96 | 0.55 |
| Kidneys rt | 69.95 | 43.87 | 128.76 | 74.5 |
| Kidneys lft | 73.35 | 47.86 | 118 | 76.3 |
| Aorta (Background) | 3.04 | 2.09 | 2.46 | 1.26 |
| Pulm. mestast. rt | 2.04 | 1.36 | 1.54 | 0.97 |
| Pulm. mestast. rt cranial | 1.39 | 0.95 | 1.19 | 0.77 |
| Pulm. mestast. rt (2) | 2.13 | 0.75 | 1.09 | 0.41 |
| Pulm. mestast. rt basal | 1.36 | 1.07 | 1.27 | 0.75 |

TABLE 12

Quantification of PET-data: Organ distribution of $^{68}$Ga-(MC-FA-012)$_3$ 1 and 3 hours after administration (SUV max/SUV mean) in patient 2 (rt = right, lft = left).

|  | 1 h | | 3 h | |
|---|---|---|---|---|
| Organs | SUV max | SUV mean | SUV max | SUV mean |
| Brain | 0.51 | 0.08 | 0.46 | 0.21 |
| Pancreas | 2.76 | 2.67 | 5.07 | 2.47 |
| Lungs | 0.58 | 0.43 | 0.51 | 0.26 |
| Liver | 2.29 | 1.56 | 1.97 | 1.08 |
| Spleen | 2.19 | 1.51 | 1.56 | 0.81 |
| Intestine ROI1 | 2.13 | 1.42 | 1.5 | 0.4 |
| Intestine ROI2 | 1.13 | 0.73 | 1.5 | 0.6 |
| Intestine ROI3 | 1.71 | 0.9 | — | — |
| Kidneys rt | 88.69 | 55 | 122.19 | 78.1 |
| Kidneys lft | 90.25 | 56.99 | 115.36 | 72.37 |
| Aorta (Background) | 2.65 | 1.86 | 1.37 | 0.8 |
| Liver metast. | 8.93 | 5.09 | 8.23 | 4.37 |
| Liver metast. medial | 4.6 | 2.53 | — | — |
| Liver metast. rt lateral | 3.71 | 2.44 | 4.23 | 2.27 |
| Liver metast. cranial | 8.66 | 4.94 | — | — |
| Pulm. metast. rt | 1.77 | 1.14 | 1.7 | 1 |
|  | 2.11 | 1.23 | — | — |
| Pulm. metast. lft | 1.51 | 0.79 | 1.47 | 0.86 |

TABLE 13

Quantification of PET-data: Organ distribution of $^{68}$Ga-(MC-FA-012)$_3$ 1 and 3 hours after administration (SUV max/SUV mean) in patient 3 (rt = right, lft = left).

|  | 1 h | | 2 h | |
|---|---|---|---|---|
| Organs | SUV max | SUV mean | SUV max | SUV mean |
| Brain rt | 0.59 | 0.32 | 0.54 | 0.28 |
| Brain lft | 0.28 | 0.14 | 0.58 | 0.36 |
| Pancreas | 2.32 | 1.04 | 0.76 | 0.31 |
| Lungs rt | 1.63 | 0.78 | 1.6 | 0.72 |
| Lungs lft | 1.83 | 0.92 | 1.44 | 0.86 |
| Liver | 1.87 | 1.07 | 2.27 | 1.22 |
| Spleen | 2.29 | 1.55 | 3.13 | 1.21 |
| Intestine | 2.32 | 1.16 | 0.76 | 0.31 |
| Kidneys rt | 77.1 | 46.67 | 102.47 | 63.11 |
| Kidneys lft | 78.34 | 46.13 | 106.37 | 59.7 |
| Aorta (Background) | 1.99 | 1.4 | 2.27 | 0.93 |
| Saliv. glands rt | 1.4 | 0.7 | 1.46 | 0.58 |
| Saliv. glands lft | 1.4 | 0.7 | 1.17 | 0.59 |
| Liver metast. rt (1) | 9.65 | 5.26 | 9.39 | 5.11 |
| Lymph node metast. | 11.91 | 6.26 | 16.34 | 8.21 |
| Liver metast. rt (2) | 8.53 | 5.28 | 9.59 | 5.58 |
| Liver metast. central | 8.51 | 4.79 | 9.7 | 5.35 |
| Liver metast. lft | 9.27 | 5.26 | 10.97 | 5.77 |

TABLE 14

Quantification of PET-data: Organ distribution of $^{68}$Ga-(MC-FA-012)$_3$ 1 and 3 hours after administration (SUV max/SUV mean) in patient 4 (rt = right, lft = left).

|  | 1 h | | 2.5 h | |
|---|---|---|---|---|
| Organs | SUV max | SUV mean | SUV max | SUV mean |
| Brain rt | 0.17 | 0.1 | 0.2 | 0.11 |
| Brain lft | 0.26 | 0.14 | 0.72 | 0.41 |
| Pancreas | — | — | — | — |
| Lungs | 2.14 | 1.04 | 2.24 | 1.21 |
| Liver | 3.95 | 2.38 | 5.41 | 2.48 |
| Spleen | 2.35 | 0.44 | 1.99 | 0.42 |
| Intestine | 1.21 | 0.56 | 3.45 | 0.73 |
| Kidneys rt | 47.87 | 26.16 | 70.49 | 40.9 |
| Kidneys lft | 50.86 | 34.71 | 76.42 | 46.22 |
| Aorta (Background) | 4.21 | 3.48 | 2.43 | 1.52 |
| Saliv. glands rt | 1.69 | 0.88 | 1.38 | 0.78 |
| Saliv. glands lft | 1.58 | 1.02 | 1.55 | 0.74 |
| Peritonitis carcinomatosa | 4.66 | 2.51 | 6.93 | 3.74 |
| Pulm. metast. (1) | 3.58 | 2.01 | 2.83 | 1.65 |
| Pulm. metast. (2) | 2.75 | 1.66 | 2.42 | 1.47 |
| Pulm. metast. (3) | 4.08 | 2.37 | 3.39 | 2.09 |

TABLE 15

Quantification of PET-data: Organ distribution of $^{68}$Ga-(MC-FA-012)$_3$ 1 and 3 hours after administration (SUV max/SUV mean) in patient 5 (rt = right, lft = left).

|  | 1 h | | 3 h | |
|---|---|---|---|---|
| Organs | SUV max | SUV mean | SUV max | SUV mean |
| Brain rt | 0.18 | 0.1 | 0.2 | 0.09 |
| Brain lft | 0.1 | 0.06 | 0.26 | 0.12 |
| Parotis rt | 1.08 | 0.72 | 1.01 | 0.44 |
| Parotis lft | 1.21 | 0.96 | 1.05 | 0.64 |
| Kidneys rt | 111.38 | 70.54 | 159.98 | 101.18 |
| Kidneys lft | 106.01 | 63.23 | 138.8 | 88 |
| Gluteal muscle rt | 0.93 | 0.53 | 0.98 | 0.34 |
| Gluteal muscle lft | 0.9 | 0.54 | 0.89 | 0.28 |
| Liver | 1.66 | 1.05 | 2.32 | 0.67 |
| Pancreas tail (tumor) | 4.56 | 2.43 | 3.82 | 1.91 |
| Pancreas head | 2.43 | 1.76 | 1.63 | 0.97 |
| Lungs rt | 0.64 | 0.38 | 0.52 | 0.22 |
| Lungs lft | 1.11 | 0.56 | 1.36 | 0.76 |
| Aorta (Background) | 1.76 | 1.15 | 1.22 | 0.54 |
| Intestine | 1.47 | 0.95 | 1.62 | 0.45 |

TABLE 15-continued

Quantification of PET-data: Organ distribution of $^{68}$Ga-(MC-FA-012)$_3$ 1 and 3 hours after administration (SUV max/SUV mean) in patient 5 (rt = right, lft = left).

|  | 1 h | | 3 h | |
| --- | --- | --- | --- | --- |
| Organs | SUV max | SUV mean | SUV max | SUV mean |
| Liver metast. (main) | 9.27 | 4.84 | 7.82 | 4 |
| Liver metast. caud. med | 4.85 | 3.04 | 5.59 | 3.42 |
| Liver metast. caud. lat | 4.47 | 2.58 | 4.67 | 2.48 |

REFERENCES

Avrutina, O., H. U. Schmoldt, D. Gabrijelcic-Geiger, D. Le Nguyen, C. P. Sommerhoff, U. Diederichsen and H. Kolmar (2005). "Trypsin inhibition by macrocyclic and open-chain variants of the squash inhibitor MCoTI-II." *Biol Chem* 386(12): 1301-1306.

Cheng, J. D., R. L. Dunbrack, Jr., M. Valianou, A. Rogatko, R. K. Alpaugh and L. M. Weiner (2002). "Promotion of tumor growth by murine fibroblast activation protein, a serine protease, in an animal model." *Cancer Res* 62(16): 4767-4772.

Eager, R. M., C. C. Cunningham, N. Senzer, D. A. Richards, R. N. Raju, B. Jones, M. Uprichard and J. Nemunaitis (2009). "Phase II trial of talabostat and docetaxel in advanced non-small cell lung cancer." *Clin Oncol (R Coll Radiol)* 21(6): 464-472.

Eager, R. M., C. C. Cunningham, N. N. Senzer, J. Stephenson, Jr., S. P. Anthony, S. J. O'Day, G. Frenette, A. C. Pavlick, B. Jones, M. Uprichard and J. Nemunaitis (2009). "Phase II assessment of talabostat and cisplatin in second-line stage IV melanoma." *BMC Cancer* 9: 263.

Goldstein, L. A., G. Ghersi, M. L. Pineiro-Sanchez, M. Salamone, Y. Yeh, D. Flessate and W. T. Chen (1997). "Molecular cloning of seprase: a serine integral membrane protease from human melanoma." *Biochim Biophys Acta* 1361(1): 11-19.

Goodman, J. D., T. L. Rozypal and T. Kelly (2003). "Seprase, a membrane-bound protease, alleviates the serum growth requirement of human breast cancer cells." *Clin Exp Metastasis* 20(5): 459-470.

Hofheinz, R. D., S. E. al-Batran, F. Hartmann, G. Hartung, D. Jager, C. Renner, P. Tanswell, U. Kunz, A. Amelsberg, H. Kuthan and G. Stehle (2003). "Stromal antigen targeting by a humanised monoclonal antibody: an early phase II trial of sibrotuzumab in patients with metastatic colorectal cancer." *Onkologie* 26(1): 44-48.

Huang, Y., S. Wang and T. Kelly (2004). "Seprase promotes rapid tumor growth and increased microvessel density in a mouse model of human breast cancer." *Cancer Res* 64(8): 2712-2716.

Kimura, R. H., Z. Cheng, S. S. Gambhir and J. R. Cochran (2009). "Engineered knottin peptides: a new class of agents for imaging integrin expression in living subjects." *Cancer Res* 69(6): 2435-2442.

Kimura, R. H., D. S. Jones, L. Jiang, Z. Miao, Z. Cheng and J. R. Cochran (2011). "Functional mutation of multiple solvent-exposed loops in the Ecballium elaterium trypsin inhibitor-II cystine knot miniprotein." *PLoS One* 6(2): e16112.

Kimura, R. H., A. M. Levin, F. V. Cochran and J. R. Cochran (2009). "Engineered cystine knot peptides that bind alphavbeta3, alphavbeta5, and alpha5beta1 integrins with low-nanomolar affinity." *Proteins* 77(2): 359-369.

Kimura, R. H., Z. Miao, Z. Cheng, S. S. Gambhir and J. R. Cochran (2010). "A dual-labeled knottin peptide for PET and near-infrared fluorescence imaging of integrin expression in living subjects." *Bioconjug Chem* 21(3): 436-444.

Kolmar, H. (2009). "Biological diversity and therapeutic potential of natural and engineered cystine knot miniproteins." *Curr Opin Pharmacol* 9(5): 608-614.

Kolmar, H. (2011). "Natural and engineered cystine knot miniproteins for diagnostic and therapeutic applications." *Curr Pharm Des* 17(38): 4329-4336.

Kraman, M., P. J. Bambrough, J. N. Arnold, E. W. Roberts, L. Magiera, J. O. Jones, A. Gopinathan, D. A. Tuveson and D. T. Fearon (2010). "Suppression of antitumor immunity by stromal cells expressing fibroblast activation protein-alpha." *Science* 330(6005): 827-830.

Lee, J., M. Fassnacht, S. Nair, D. Boczkowski and E. Gilboa (2005), "Tumor immunotherapy targeting fibroblast activation protein, a product expressed in tumor-associated fibroblasts." *Cancer Res* 65(23): 11156-11163.

Liao, D., Y. Luo, D. Markowitz, R. Xiang and R. A. Reisfeld (2009). "Cancer associated fibroblasts promote tumor growth and metastasis by modulating the tumor immune microenvironment in a 4T1 murine breast cancer model." *PLoS One* 4(11): e7965.

Liu, S., H. Liu, G. Ren, R. H. Kimura, J. R. Cochran and Z. Cheng (2011). "PET Imaging of Integrin Positive Tumors Using F Labeled Knottin Peptides." *Theranostics* 1: 403-412.

Lobstein, J., C. A. Emrich, C. Jeans, M. Faulkner, P. Riggs and M. Berkmen (2012). "SHuffle, a novel *Escherichia coli* protein expression strain capable of correctly folding disulfide bonded proteins in its cytoplasm." *Microb Cell Fact* 11: 56.

Loeffler, M., J. A. Kruger, A. G. Niethammer and R. A. Reisfeld (2006). "Targeting tumor-associated fibroblasts improves cancer chemotherapy by increasing intratumoral drug uptake." *J Clin invest* 116(7): 1955-1962.

Moore, S. J. and J. R. Cochran (2012). "Engineering knottins as novel binding agents." *Methods Enzymol* 503: 223-251.

Narra, K., S. R. Mullins, H. O. Lee, B. Strzemkowski-Brun, K. Magalong, V. J. Christiansen, P. A. McKee, B. Egleston, S. J. Cohen, L. M. Weiner, N. J. Meropol and J. D. Cheng (2007). "Phase II trial of single agent Val-boroPro (Talabostat) inhibiting Fibroblast Activation Protein in patients with metastatic colorectal cancer." *Cancer Biol Ther* 6(11): 1691-1699.

Ostermann, E., P. Garin-Chesa, K. H. Heider, M. Kalat, H. Lamche, C. Puri, D. Kerjaschki, W. J. Rettig and G. R. Adolf (2008). "Effective immunoconjugate therapy in cancer models targeting a serine protease of tumor fibroblasts." *Clin Cancer Res* 14(14): 4584-4592.

Pineiro-Sanchez, M. L., L. A. Goldstein, J. Dodt, L. Howard, Y. Yeh, H. Tran, W. S. Argraves and W. T. Chen (1997). "Identification of the 170-kDa melanoma membrane-bound gelatinase (seprase) as a serine integral membrane protease." *J Biol Chem* 272(12): 7595-7601.

Ramirez-Montagut, T., N. E. Blachere, E. V. Sviderskaya, D. C. Bennett, W. J. Rettig, P. Garin-Chesa and A. N. Houghton (2004). "FAPalpha, a surface peptidase expressed during wound healing, is a tumor suppressor." *Oncogene* 23(32): 5435-5446.

Rui Liu, H. L., Liang Lin, Jinpu Yu, Xiubao Ren (2012). "Fibroblast activation protein: A potential therapeutic target in cancer." *Cancer biology & therapy* 13(3): 123-129.

Santos, A. M., J. Jung, N. Aziz, J. L. Kissil and E. Pure (2009). "Targeting fibroblast activation protein inhibits tumor stromagenesis and growth in mice." *J Clin Invest* 119(12): 3613-3625.

Scott, A. M., G. Wiseman, S. Welt, A. Adjei, F. T. Lee, W. Hopkins, C. R. Divgi, L. H. Hanson, P. Mitchell, D. N. Gansen, S. M. Larson, J. N. Ingle, E. W. Hoffman, P. Tanswell, G. Ritter, L. S. Cohen, P. Bette, L. Arvay, A. Amelsberg, D. Vlock, W. J. Rettig and L. J. Old (2003). "A Phase I dose-escalation study of sibrotuzumab in patients with advanced or metastatic fibroblast activation protein-positive cancer." *Clin Cancer Res* 9(5): 1639-1647.

Stern, L. A., B. A. Case and B. J. Hackel (2013). "Alternative Non-Antibody Protein Scaffolds for Molecular Imaging of Cancer." *Curr Opin Chem Eng* 2(4).

Weidle, U. H., J. Auer, U. Brinkmann, G. Georges and G. Tiefenthaler (2013). "The emerging role of new protein scaffold-based agents for treatment of cancer." *Cancer Genomics Proteomics* 10(4): 155-168.

Welt, S., C. R. Divgi, A. M. Scott, P. Garin-Chesa, R. D. Finn, M. Graham, E. A. Carswell, A. Cohen, S. M. Larson, L. J. Old and et al. (1994). "Antibody targeting in metastatic colon cancer: a phase I study of monoclonal antibody F19 against a cell-surface protein of reactive tumor stromal fibroblasts." *J Clin Oncol* 12(6): 1193-1203.

Wen, Y., C. T. Wang, T. T. Ma, Z. Y. Li, L. N. Zhou, B. Mu, F. Leng, H. S. Shi, Y. O. Li and Y. Q. Wei (2010). "Immunotherapy targeting fibroblast activation protein inhibits tumor growth and increases survival in a murine colon cancer model." *Cancer Sci* 101(11): 2325-2332.

Wesley, U. V., A. P. Albino, S. Tiwari and A. N. Houghton (1999). "A role for dipeptidyl peptidase IV in suppressing the malignant phenotype of melanocytic cells." *J Exp Med* 190(3): 311-322.

The invention claimed is:

1. A Seprase binding peptide which comprises the amino acid sequence Gly Arg Gly Pro (SEQ ID NO: 5), wherein
   (a) the Seprase binding peptide forms and/or is part of a cystine knot structure containing at least three disulphide bridges formed from pairs of cysteine molecules, and
   (b) the amino acid sequence Gly Arg Gly Pro (SEQ ID NO: 5) is part of the cystine knot structure wherein the amino acid sequence is located between the first cysteine and the second cysteine of the cystine knot structure.

2. The Seprase binding peptide of claim 1, which comprises the amino acid sequence:

```
                                           (SEQ ID NO: 6)
  Tyr Xaa1 Xaa2 Trp Xaa3 Xaa4 Gly Arg Gly Pro
``` wherein
Xaa1 is any amino acid,
Xaa2 is any amino acid,
Xaa3 is any amino acid,
Xaa4 is any amino acid.

3. The Seprase binding peptide of claim 1, which comprises the amino acid sequence:

```
                                           (SEQ ID NO: 7)
  Tyr Xaa1 Asn Trp Thr Pro Gly Arg Gly Pro
``` wherein
Xaa1 is any amino acid.

4. The Seprase binding peptide of claim 1, which comprises the amino acid sequence:

```
                                           (SEQ ID NO: 8)
  Tyr Ser Asn Trp Thr Pro Gly Arg Gly Pro.
```

5. The Seprase binding peptide of claim 1, which comprises the amino acid sequence:

```
(Xaa)n1 Cys (Xaa)n2 Gly Arg Gly Pro (Xaa)n3 Cys (Xaa)n4 Cys (Xaa)n5 Cys (Xaa)n6 Cys (Xaa)n7 Cys (Xaa)n8
``` wherein the Cys residues form a cystine knot structure,

Xaa is independently from each other any amino acid and n1, n2, n3, n4, n5, n6, n7, and n8 are the respective numbers of amino acids, wherein the nature of the amino acids Xaa and/or the number of amino acids n1, n2, n3, n4, n5, n6, n7 and n8 are such that a cystine knot structure can form between the Cys residues, wherein n1 is 0 to 4, n2 is 3 to 10, n3 is 0 to 4, n4 is 3 to 7, n5 is 2 to 6, n6 is 1 to 3, n7 is 3 to 7, and n8 is 0 to 4.

6. The Seprase binding peptide of claim 1, which comprises the amino acid sequence:

```
                                           (SEQ ID NO: 17)
  Cys Xaa1 Tyr Xaa2 Xaa3 Trp Xaa4 Xaa5 Gly Arg Gly

Pro Xaa6 Cys Arg Arg Asp Ser Asp Cys Pro Gly Xaa7

Cys Ile Cys Arg Gly Asn Gly Tyr Cys
``` wherein

Xaa1 is any amino acid,

Xaa2 is any amino acid,

Xaa3 is any amino acid,

Xaa4 is any amino acid,

Xaa5 is any amino acid,

Xaa6 is any amino acid,

Xaa7 is any amino acid.

7. The Seprase binding peptide of claim 1, which comprises the amino acid sequence:

(SEQ ID NO: 18)
Cys Pro Tyr Xaa1 Asn Trp Thr Pro Gly Arg Gly Pro

Xaa2 Cys Arg Arg Asp Ser Asp Cys Pro Gly Xaa3

Cys Ile Cys Arg Gly Asn Gly Tyr Cys wherein
Xaa1 is any amino acid,
Xaa2 is any amino acid,
Xaa3 is any amino acid.

8. The Seprase binding peptide of claim 1, which comprises the amino acid sequence:

(SEQ ID NO: 19)
Cys Pro Tyr Ser Asn Trp Thr Pro Gly Arg Gly Pro

Asp Cys Arg Arg Asp Ser Asp Cys Pro Gly Arg Cys

Ile Cys Arg Gly Asn Gly Tyr Cys.

9. The Seprase binding peptide of claim 1, which comprises the amino acid sequence:

(SEQ ID NO: 12)
Xaa1 Xaa2 Cys Xaa3 Tyr Xaa4 Xaa5 Trp Xaa6 Xaa7 Gly

Arg Gly Pro Xaa8 Cys Arg Arg Asp Ser Asp Cys Pro

Gly Xaa9 Cys Ile Cys Arg Gly Asn Gly Tyr Cys Gly wherein
Xaa1 is any amino acid,
Xaa2 is any amino acid,
Xaa3 is any amino acid,
Xaa4 is any amino acid,
Xaa5 is any amino acid,
Xaa6 is any amino acid,
Xaa7 is any amino acid,
Xaa8 is any amino acid,
Xaa9 is any amino acid.

10. The Seprase binding peptide of claim 1, which comprises the amino acid sequence:

(SEQ ID NO: 21)
Xaa1 Xaa2 Cys Pro Tyr Xaa3 Asn Trp Thr Pro Gly Arg

Gly Pro Xaa4 Cys Arg Arg Asp Ser Asp Cys Pro Gly

Xaa5 Cys Ile Cys Arg Gly Asn Gly Tyr Cys Gly wherein
Xaa1 is any amino acid,
Xaa2 is any amino acid,
Xaa3 is any amino acid,
Xaa4 is any amino acid,
Xaa5 is any amino acid.

11. The Seprase binding peptide claim 1, which comprises the amino acid sequence:

(SEQ ID NO: 22)
Gly Lys Cys Pro Tyr Ser Asn Trp Thr Pro Gly Arg

Gly Pro Asp Cys Arg Arg Asp Ser Asp Cys Pro Gly

Arg Cys Ile Cys Arg Gly Asn Gly Tyr Cys Gly.

12. A Seprase binding peptide comprising the amino acid sequence:

(SEQ ID NO: 23)
Gly Ala Cys Pro Tyr Ser Asn Trp Thr Pro Gly Arg

Gly Pro Asp Cys Arg Arg Asp Ser Asp Cys Pro Gly

Arg Cys Ile Cys Arg Gly Asn Gly Tyr Cys Gly.

13. The Seprase binding peptide of claim 1, wherein the cystine knot structure is based on the open chain trypsin inhibitor II from Momordica cochinchinensis (MCoTI-II).

14. A Seprase binding peptide comprising the amino acid sequence Gly Arg Gly Pro (SEQ ID NO: 5) and at least one fusion partner.

15. The Seprase binding peptide of claim 14, wherein the fusion partner comprises a heterologous amino acid sequence.

16. A Seprase binding agent comprising the amino acid sequence Gly Arg Gly Pro (SEQ ID NO: 5) covalently and/or non-covalently associated with at least one further moiety.

* * * * *